US007129331B2

(12) United States Patent
Pestka

(10) Patent No.: US 7,129,331 B2
(45) Date of Patent: Oct. 31, 2006

(54) PHOSPHORYLATED POLYPEPTIDES AND USES RELATED THERETO

(75) Inventor: Sidney Pestka, North Caldwell, NJ (US)

(73) Assignee: Pestka Biomedical Laboratories, Inc., Piscataway, NJ (US)

( * ) Notice: Subject to any disclaimer, the term of this patent is extended or adjusted under 35 U.S.C. 154(b) by 220 days.

(21) Appl. No.: 09/872,349

(22) Filed: May 31, 2001

(65) Prior Publication Data

US 2002/0132980 A1 Sep. 19, 2002

Related U.S. Application Data

(60) Provisional application No. 60/255,296, filed on Dec. 13, 2000, provisional application No. 60/208,240, filed on May 31, 2000.

(51) Int. Cl.
*A61K 38/00* (2006.01)

(52) U.S. Cl. ................................ 530/387.3; 530/387.1

(58) Field of Classification Search ............. 530/387.1, 530/387.3; 424/130.1
See application file for complete search history.

(56) References Cited

U.S. PATENT DOCUMENTS 4,923,802 A 5/1990 Gallis
5,986,061 A * 11/1999 Pestka

FOREIGN PATENT DOCUMENTS

EP 0 372 707 A2 6/1990

OTHER PUBLICATIONS

Lin et al Protein Expression and Purification 15:83-91, 1999.*
Lin et al Anticancer Res 18:3971-3978, 1998.*
Harris et al Biochemistry 36:1581-97, 1997.*
Rudikoff et al PNAS 79:1979, 1982.*
Illustrated Dictionary of Immunology ed., Cruse, 1997, p. 106.*
Andersen, Hans C. Rattle: A "Velocity" Version of the Shake Algorithm for Molecular Dynamics Calculations. *J. Comput. Chem.* 52, 24-34 (1983).
Brooks, Bernard R. et al. CHARMM: A Program for Macromolecular Energy, Minimization, and Dynamics Calculations. *J. Comput. Chem.* 4, 187-217 (1983).
Burbaum, Jonathan J. et al. Understanding Structural Relationships in Proteins of Unsolved Three-Dimensional Structure. *Proteins* 7, 99-111 (1990).
Eisenfeld, Jerome et al. Constrained optimization and protein structure determination. *Am. J. Physiol.* 261, C376-386 (1991).
Froimowitz, Mark. The Development of Computer Simulations of the Geometries and Thermodynamics of Biological Molecules. *BioTechniques* 8, 640-652 (1990).
Kini, R. Manjunatha & Evans, Herbert J. Molecular Modeling of Proteins: A Strategy for Energy Minimization by Molecular Mechanics in the AMBER Force Field. *J. Biomol. Structure & Dynamics* 9, 475-488 (1991).

Lybrand, Terry P. Molecular Simulation and Drug Design. *J. Pharm. Belg.* 46, 49-54 (1991).
Pedersen, L. Conformational Properties of Molecules by ab Initio Quantum Mechanical Energy Minimization. *Envi. Health Perspec.* 61, 185-190 (1985).
Ryckaert, Jean-Paul et al. Numerical Integration of the Cartesian Equations of Motion of a System with Constraints: Molecular Dynamics of n-Alkanes. *J. Comput. Phys.* 23, 327-341 (1977).
van Gunsteren, W. F. & Berendsen, H. J. C. Algorithms for macromolecular dynamics and constraint dynamics. *Mol. Phys.* 34, 1311-1327 (1977).
Weiner, Paul K. & Kollman, Peter A. AMBER: Assisted Model Building with Energy Refinement. A General Program for Modeling Molecules and Their Interactions. *J. Comput. Chem.* 2, 287-303 (1981).
Lin et al., 1996, "Construction of Phosphorylatable Monoclonal Antibody to a Tumor-associated Antigen," Cancer Res. 56:4250-4254.
Lin et al., 1998, "Construction of phosphorylatable chimeric monoclonal antibody CC49," Int. J. of Oncology 13:115-120.
Pestka et al., 1999, "Introduction of Protein Kinase Recognition Sites into Proteins: A Review of Their Preparation, Advantages, and Applications," Protein Exp. and Purif. 17:203-214.
Pestka et al., 2000, "Use of Phosphorylation Site Tags in Proteins," Meth. in Enzym. 327:594-613.
Mohanraj et al., 1996, "Expression and Radiolabeling of Recombinant Proteins Containing a Phosphorylation Motif," Prot. Exp. & Purif. 8:175-182.
Fryxell et al., 1995, "Genetic Construction of a Phosphorylation Site in Ricin A Chain: Specific Radiolabeling of Recombinant Proteins for Localization and Degradation Studies," Biochem. & Biophys. Comm. 210(2):253-259.
Wu et al., 1994, "Identifying substrate Motifs of Protein Kinases by a Random Library Approach," Biochem. 33:14825-14833.
Kemp et al., 1977, "Role of Multiple Basic Residues I Determining the Substrate Specificity of Cyclic AMP-dependent Protein Kinase," J. Biol. Chem. 252(14):4888-4894.

* cited by examiner

*Primary Examiner*—Sheela J. Huff
(74) *Attorney, Agent, or Firm*—Fish & Neave IP Group Ropes & Gray LLP

(57) ABSTRACT

Methods to generate modified polypeptides, modified antibodies, stably phosphorylated modified polypeptides, stably phosphorylated modified antibodies, polynucleotide sequences encoding the polypeptides, and uses thereof are provided. A computer-aided molecular modeling method is also provided to generate modified phosphorylatable polypeptides, particularly monoclonal antibodies (MAbs) for use in the diagnosis and treatment of cancers and other diseases. The corresponding MAbs contain heterologous recognition sites for polypeptide kinases and can be labeled by an identifiable label, such as radio-isotope $^{32}P$. The phosphate group(s) attached to the phosphorylated polypeptide is unusually stable due to engineered intramolecular interactions between the phosphate group and its neighbouring groups. Polynucleotide sequences which encode a monoclonal antibody containing sequences encoding a putative phosphorylation site, and methods for analyzing the biochemical properties of a polypeptide by using molecular modeling tools, are also disclosed.

8 Claims, 48 Drawing Sheets

K2 FRAGMENT:
```
     XmaI                                                MODIFIED XmaI
5' CCGGGC AGA AGG GCA AGT CTG CAT AGA AGG GCA AGT ATG AAG GCA 3'
3'     CG TCT TCC CGT TCA GAC GTA TCT TCC GCT TCA TAC TTC CGTGGCC 5'
          Arg Arg Ala Ser Leu His Arg Arg Ala Ser Met Lys Ala
```

Fig. 3

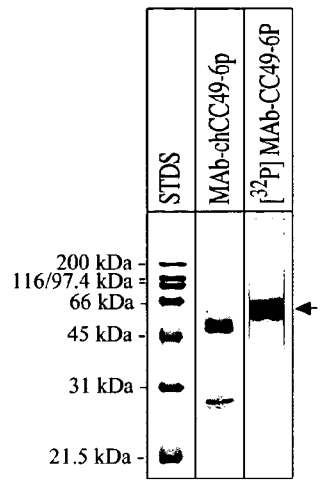
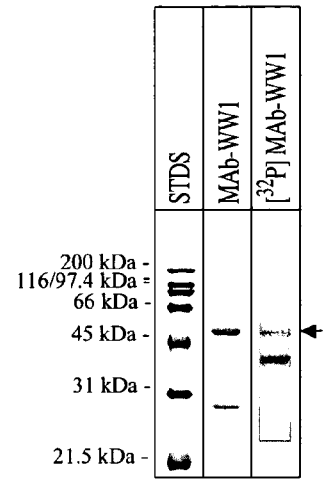
Fig. 27A        Fig. 27B
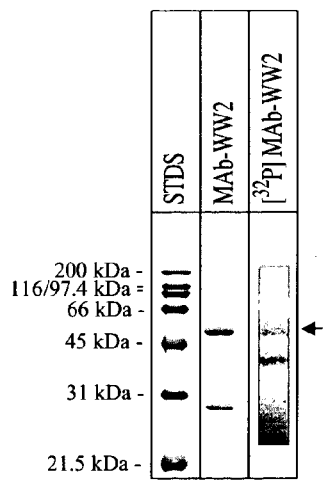
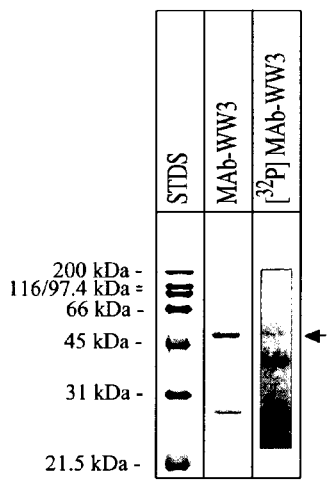
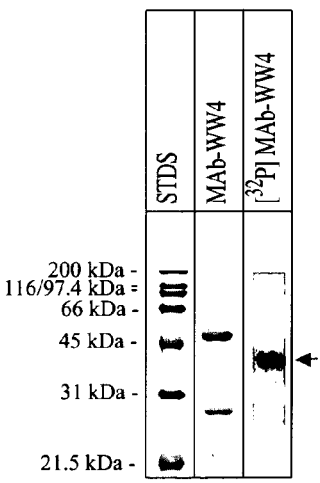
Fig. 27C        Fig. 27D        Fig. 27E

|  | UPPER | CORE | LOWER |
|---|---|---|---|
| MAb-chCC49: | EPKSCDKTHT | CPPCP | APELLGGP |
| MAb231: | EPRGPTIKP | CPPCKCP | APNLLGGP |
| MAb61.1.3: | VPRDCG | CKPCICT | VPEV |
Fig. 38A
MAb-chCC49 x MAb231
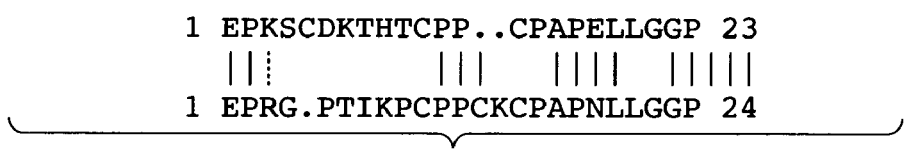
Fig. 38B
MAb-chCC49 x MAb61.1.3
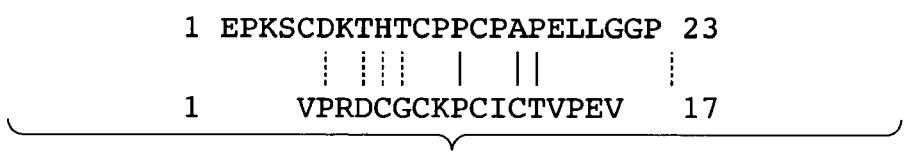
Fig. 38C
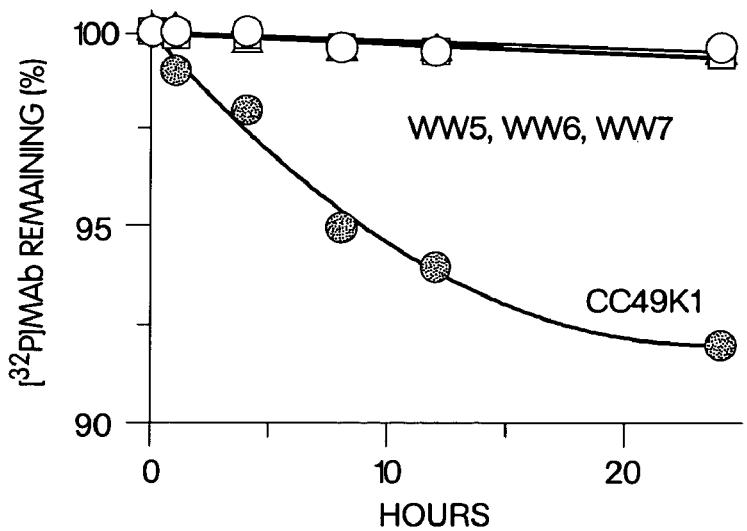
Fig. 39

SEQUENCE LISTING

<160> NUMBER OF SEQ ID NOS: 46

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:
      phosphorylated peptide

<400> SEQUENCE: 1

Arg Arg Ala Ser
 1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:
      phosphorylated peptide

<400> SEQUENCE: 2

```
Arg Arg Ala Ser Val
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence:
      phosphorylated peptide

<400> SEQUENCE: 3

Arg Thr Lys Arg Ser Gly Ser Val
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:
      phosphorylated peptide

<400> SEQUENCE: 4

Arg Lys Arg Ser Arg Lys Glu
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:
      phosphorylated peptide

<400> SEQUENCE: 5

Leu Arg Arg Ala His Leu Gly
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:
      phosphorylated peptide

<400> SEQUENCE: 6

Ser Glu Glu Glu Glu Glu
 1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:
      phosphorylated peptide

<400> SEQUENCE: 7

Arg Arg Arg Glu Glu Glu Thr Glu Glu Glu
 1               5                  10

<210> SEQ ID NO 8
<211> LENGTH: 10
<212> TYPE: PRT
<213> ORGANISM: Artificial Sequence
```

```
<220> FEATURE:
<223> OTHER INFORMATION: Description of Artificial Sequence:
      phosphorylated peptide

<400> SEQUENCE: 8

Arg Arg Arg Glu Glu Glu Ser Glu Glu Glu
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:
      phosphorylated peptide

<400> SEQUENCE: 9

Arg Arg Arg Asp Asp Asp Ser Asp Asp Asp
 1               5                  10

<210> SEQ ID NO 10
<211> LENGTH: 10
<212> TYPE: PRT
<213> ORGANISM: Artificial Sequence
<220> FEATURE:
<221> NAME/KEY: SITE
<222> LOCATION: (7)
<223> OTHER INFORMATION: Xaa=Ser or Thr
<223> OTHER INFORMATION: Description of Artificial Sequence:
      phosphorylated peptide

<400> SEQUENCE: 10

Ala Ala Ala Ala Ala Ala Xaa Glu Glu Glu
 1               5                  10

<210> SEQ ID NO 11
<211> LENGTH: 10
<212> TYPE: PRT
<213> ORGANISM: Artificial Sequence
<220> FEATURE:
<221> NAME/KEY: SITE
<222> LOCATION: (7)
<223> OTHER INFORMATION: Xaa=Ser or Thr
<223> OTHER INFORMATION: Description of Artificial Sequence:
      phosphorylated peptide

<400> SEQUENCE: 11

Ala Ala Ala Glu Glu Glu Xaa Glu Glu Glu
 1               5                  10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:
      phosphorylated peptide

<400> SEQUENCE: 12

Arg Arg Leu Ser Ser Leu Arg Ala
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:
      phosphorylated peptide
```

<400> SEQUENCE: 13

Thr Glu Thr Ser Gln Val Ala Pro Ala
 1               5

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 14
gtgaccgctg taccaacctc tgtcc                                            25

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 15
ccctcgagtc acttgcccgg ggacagggag agg                                   33

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 16
gcagcctcca ccaggcgccc atcggtc                                          27

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 17
gggcatgtgt gacgtctgtc acaagatttg                                       30

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 18
cctggggctt cgcgaaggat ttcctgcaag g                                     31

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 19

```
gtgtcagttg gccggagggt tactttgagc                                    30
```

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 20

```
cggtgggcat gagtgacgtc tgtcacaaga tttg                               34
```

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 21

```
cggtgggcat gagtgacgtc tgtcacaaga tttg                               34
```

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 22

```
cccctcgagc caccatggag tggtcctggg tc                                 32
```

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 23

```
cccaagcttt ttggcgctgg agacggtgac cag                                33
```

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 24

```
cctctagacc accatggata gccaggccca g                                  31
```

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 25

```
gccgcggccc gtggatcctt cagttccagc tt                                 32
```

<210> SEQ ID NO 26

-continued

```
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 26
gtgaccgctg taccaacctc tgtcc                                         25

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 27
ccctcgagtc acttgcccgg ggacagggag agg                                33

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 28
gcagcctcca ccaggcgccc atcggtc                                       27

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 29
gggcatgtgt gacgtctgtc acaagatttg                                    30

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 30
cctggggctt cgcgaaggat ttcctgcaag g                                  31

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 31
gtgtcagttg gccggagggt tactttgagc                                    30

<210> SEQ ID NO 32
<211> LENGTH: 45
<212> TYPE: DNA
<213> ORGANISM: Artificial Sequence
```

-continued

<220> FEATURE:
<223> OTHER INFORMATION: Description of Artificial Sequence: K2 fragment

<400> SEQUENCE: 32
ccgggcagaa gggcaagtct gcatagaagg gcaagtatga aggca                45

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: K2 fragment

<400> SEQUENCE: 33
ccggtgcctt catacttcgc cttctatgga ctcatgctcc tctgc                45

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: K2 fragment

<400> SEQUENCE: 34

Arg Arg Ala Ser Leu His Arg Arg Ala Ser Met Lys Ala
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: MAb-chCC49
      upper

<400> SEQUENCE: 35

Glu Pro Lys Ser Cys Asp Lys Thr His Thr
 1               5                  10

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: MAb-chCC49
      core

<400> SEQUENCE: 36

Cys Pro Pro Cys Pro
 1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: MAb-chCC49
      lower

<400> SEQUENCE: 37

Ala Pro Glu Leu Leu Gly Gly Pro
 1               5

<210> SEQ ID NO 38
<211> LENGTH: 9
<212> TYPE: PRT
<213> ORGANISM: Artificial Sequence

```
<220> FEATURE:
<223> OTHER INFORMATION: Description of Artificial Sequence: MAb231
      upper

<400> SEQUENCE: 38

Glu Pro Arg Gly Pro Thr Ile Lys Pro
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: MAb231 core

<400> SEQUENCE: 39

Cys Pro Pro Cys Lys Cys Pro
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: MAb231
      lower

<400> SEQUENCE: 40

Ala Pro Asn Leu Leu Gly Gly Pro
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: MAb61.1.3
      upper

<400> SEQUENCE: 41

Val Pro Arg Asp Cys Gly
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: MAb61.1.3
      core

<400> SEQUENCE: 42

Cys Lys Pro Cys Ile Cys Thr
1               5

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: MAb61.1.3
      lower

<400> SEQUENCE: 43

Val Pro Glu Val
1
```

```
<210> SEQ ID NO 44
<211> LENGTH: 23
<212> TYPE: PRT
<213> ORGANISM: Artificial Sequence
<220> FEATURE:
<223> OTHER INFORMATION: Description of Artificial Sequence: MAb-chCC49

<400> SEQUENCE: 44

Glu Pro Lys Ser Cys Asp Lys Thr His Thr Cys Pro Pro Cys Pro Ala
 1               5                  10                  15

Pro Glu Leu Leu Gly Gly Pro
            20

<210> SEQ ID NO 45
<211> LENGTH: 24
<212> TYPE: PRT
<213> ORGANISM: Artificial Sequence
<220> FEATURE:
<223> OTHER INFORMATION: Description of Artificial Sequence: MAb231

<400> SEQUENCE: 45

Glu Pro Arg Gly Pro Thr Ile Lys Pro Cys Pro Pro Cys Lys Cys Pro
 1               5                  10                  15

Ala Pro Asn Leu Leu Gly Gly Pro
            20

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: MAb61.1.3

<400> SEQUENCE: 46

Val Pro Arg Asp Cys Gly Cys Lys Pro Cys Ile Cys Thr Val Pro Glu
 1               5                  10                  15

Val
```

PHOSPHORYLATED POLYPEPTIDES AND USES RELATED THERETO

CROSS-REFERENCE TO RELATED APPLICATIONS

This application is based, at least in part, on Provisional Application No. 60/208,240, filed May 31, 2000, and Provisional Application No. 60/255,296, filed Dec. 13, 2000, the respective disclosures of which are incorporated by reference herein.

BACKGROUND OF THE INVENTION

This invention relates to improved methods for generating phosphorylatable polypeptides, polypeptides generated using those methods, DNA sequences encoding those polypeptides, and their use in diagnosis and treatment of cancer and other diseases.

Labeled polypeptides are used in a variety of applications. For instance, labeled monoclonal antibodies (MAbs) have been widely used in radio-immunotherapy, diagnostic imaging and staging of tumors.

Labeled monoclonal antibodies (MAbs) have great applicability for the diagnosis and treatment of cancer for several reasons. First, most tumor populations express tumor antigens in a heterogeneous pattern. Some of the cells in the population will not be expressing the target tumor antigen and therefore will not be recognized by the monoclonal antibody. With the use of MAbs to deliver drugs or toxins to tumor cells, the cells which lack the tumor antigen remain untouched. In contrast, radio labeled MAbs provide the advantage of destroying cells within a radius of a few cell diameters around the tumor cell to which the MAb binds. It has been shown that an $^{131}$I-labeled MAb can deliver a therapeutic dose of radiation to antigen negative cells. Second, in the case of carcinomas, the tumor antigens are stable on the cell surface and are not internalized. For a drug or toxin to be effective, it is necessary to have it enter the cell. In contrast, radio labeled MAbs kill the tumor cells after binding to the surface and do not require entry into the cell. Therefore, this technique has applicability to great variety of cancers. Furthermore, the use of interferons and other cytokines can be used to enhance the expression of tumor associated antigens on cells providing a better target for monoclonal antibodies and minimize or even eliminate tumor cells previously not expressing the tumor antigen.

In radio-immunotherapy, $^{131}$I has been commonly used for cancer therapy. However since iodine labeling is not site specific, it results in a heterogeneous population of labeled MAbs with various affinities for antigen and significant inactivation of the Mab. Iodine-labeled polypeptides can also undergo dehalogenation, which can eliminate $^{131}$I from tumors before it starts to function. Another disadvantage of iodine labeling is that iodine can concentrate in the thyroid, salivary glands and stomach, which can pose health problems for patients and health care personnel.

Compared to $^{131}$I, $^{32}$P has been considered to be a better option for radio-immunotherapy. Being a pure β-emitter, it has high energy (Emax 1700 keV, compared to $^{131}$I, 182 keV) which is strong enough for cancer therapy. However the utilization of this radioisotope was greatly limited due to the difficulties in $^{32}$P labeling of MAbs. A $^{32}$P labeled peptide can also be chemically coupled to the polypeptide via lysine residues. However, the peptide-Ab conjugation is not site specific, which, like iodine labeling, can also compromise the Ag binding ability of the MAb.

This $^{32}$P labeling problem was not satisfactorily solved until the development of a simple and rapid labeling procedure and the construction of a phosphorylatable fusion polypeptide by the introduction of a peptide kinase recognition site into the polypeptide. See, for example, U.S. Pat. No. 5,986,061, the disclosure of which is incorporated by reference herein in its entirety. This is a simple, efficient way to label polypeptides using radio-nucleotides, and is applicable to virtually any polypeptide. Many polypeptide kinase recognition sites can be introduced into polypeptides and serve as useful tags for a variety of purposes. The introduction of polypeptide kinase recognition sites into polypeptides can be achieved without modifying the essential structure or function of the polypeptides. Because polypeptides modified by these procedures retain their activity after phosphorylation, they can be used in many applications.

Phosphorylatable MAbs (MAb-chB72.3-P, MAb-chCC49K1, MAb-chCC49CKI, MAb-chCC49CKII and MAb-chCC49Tyr) can be created by inserting the predicted consensus sequences for phosphorylation by the cAMP-dependent polypeptide kinase and other polypeptide kinases, such as casein kinase I, casein kinase II and the Src tyrosine kinase, at the carboxyl terminus of the heavy chain constant region of MAb-chB72.3-P or MAb-chCC49. These MAbs are purified and phosphorylated by the appropriate polypeptide kinase with [γ-$^{32}$P]ATP to high specific activity. These [$^{32}$P]MAbs bind to cells expressing TAG-72 antigens with high specificity. In all these cases, the phosphate is stable in vitro in various sera so that less than 8% of the phosphate is hydrolyzed in 24 hours.

However, it has been found that the attached $^{32}$P in the above phosphorylatable antibodies is not sufficiently stable in buffer or serum to be useful for in vivo applications in animals and humans. Several methods have been suggested to improve the stabilities of the phosphorylatable MAbs. Since RRX(S/T) is a PKA recognition site, changing the amino acid residue X or the amino acid residues downstream of this site changes the stability of the phosphorylatable MAbs. It has also been found that using threonine, instead of serine, in the PKA recognition site increases the stability of the phosphorylatable Mabs, although this would compromise the efficiency of the phosphorylation dramatically. Alternatively, the stability of the phosphorylatable MAbs might also be changed if other phosphorylation enzymes are used. There is no assurance that these approaches would be satisfactory.

The choice of putative phosphorylation sites can at times be tricky since many point mutations, insertions or deletions may dramatically change the conformation of the entire molecule or at least render the polypeptide less functional. In addition, those sites might be potentially unaccessible to the intended kinases due to steric hinderance. In the past, these problems were dealt with using such inefficient and time-consuming methods as trial-and-error.

Accordingly, what is needed is a reasonably accurate yet highly efficient means to carry out this process, not only for labeling phosphorylatable monoclonal antibodies, but also as a general method for generating any phosphorylatable polypeptides.

SUMMARY OF THE INVENTION

The instant invention provides improved methods, such as computer-aided molecular modeling, to locate phosphorylation sites in polypeptide of interest (i.e. MAb such as MAb-chCC49). An advantage of these methods is that a myriad of potential phosphorylation sites in the target polypeptide can be quickly surveyed and the optimum choices identified by predicting potential intramolecular stabilizing interactions. Hydrogen bonding between the attached phosphate groups and their neighboring groups provides a simple method to locate regions where surrounding residues protect the phosphate from hydrolysis. Therefore, stability of the attached phosphate groups can be reliably predicted within a short period of time, thus representing a vast improvement over the time-consuming and rather inefficient trial-and-error approach.

In a broad sense, the invention contemplates computer-aided molecular modeling to generate phosphorylatable polypeptides, e.g. to radio-label polypeptides, especially monoclonal antibodies (MAbs), and polynucleotide molecules encoding the radio-labellable polypeptides.

In one aspect, the invention provides improved methods to generate radio-labeled polypeptides. In one embodiment, the instant invention provides methods to generate, inter alia, MAbs and Ag binding polypeptides which can be stably phosphorylated to high radio-specific activity with retention of biological activity (affinity for their intended antigens); MAbs modified with various isotopes of phosphorus (e.g., $^{32}P$, $^{33}P$), or with sulfur (e.g., $^{35}S$, $^{38}S$); and MAbs labelled with phosphorus or analogs. In accordance with the invention, the MAbs and modified polypeptides may have single or multiple radioactive labels.

The invention also provides a method to generate polypeptides other than MAbs, which are modified by the addition of phosphorylation sites which allow for and are labeled to higher radio-specific activities than the corresponding unmodified polypeptide with a single phosphorylation site. By the "addition" of phosphorylation sites, there is also intended in accordance with the invention, to include polypeptides in which a phosphorylation site heretofore unavailable or inaccessible, has been modified to make the phosphorylation site available.

The invention further provides a method to generate polypeptides, especially MAbs and Ag binding polypeptides, phosphorylated by appropriate kinases on amino acid residues other than on the serine residue, like on threonine and/or tyrosine residues, and the DNA sequences which code for one or more putative phosphorylation sites, which sequences code for these polypeptides.

The invention additionally provides a method to generate polypeptides, such as interferons, cytokines, growth factors, receptor binding proteins and peptides with phosphorylation sites to bind to receptors or other cellular targets.

In accordance with the invention, it is sufficient that a portion of the phosphorylation recognition sequence, as opposed to the entire sequence, be added when the natural polypeptide sequence contains the remaining (or other complementary) amino acids of said recognition sequence (e.g., Arg-Arg-Ala-Ser, (SEQUENCE ID NO. 1)). In such embodiment of the invention, from 1 through 4 amino acids of the sequence (in the case of Arg-Arg-Ala-Ser-Val, (SEQUENCE ID NO. 2)) can be supplied to the polypeptide, thereby constituting the Ser-containing recognition sequence. This illustrates the versatility of the invention for positioning the nucleotide sequence which encodes the amino acid recognition sequence containing a putative phosphorylation site.

Further, the availability of the 3-dimentional structure of a template molecule for computer-aided modeling can precisely predict the consequences of altering natural amino acid sequences in generating putative phosphorylation sites in the test polypeptide, the consequences of introducing phosphate groups, and the possibility of forming stabilizing intramolecular interactions loacted by identifying regions where the phosphate is protected by neighboring residues (i.e. hydrogen-bonding serves as a surrogate marker for the facile location of such regions). This will significantly speed up the trial-and-error engineering process, thus achieving more accurate and predictable results.

The phosphorylated MAbs generated using the methods provided by the instant invention are unexpectedly stable. In one preferred embodiment of the invention, monoclonal antibodies are generated to posess optimized phosphorylation sites, so that phosphate groups attached to those sites are unusually resistant to hydrolysis, either in vitro or in vivo. In a preferred embodiment, at least 80%, more preferably 95%, and most preferably 99% of the phosphate groups remain attached after at least 5 days, more preferably 10 days, and most preferably 18 days in sera or buffer. In a most preferred embodiment, 95% of the phosphate groups remain attached after 18 days in bufffer.

In addition, it was unexpectedly found that those stable monoclonal antibodies had much more improved plasma clearance and biodistribution properties when compared with other phosphorylated MAbs generated by conventional methods. In a preferred embodiment, only 70% (as compared to 90% of control phosphorylated Mabs) of phosphorylated Mabs were cleared from blood in a plasma clearance assay. In another preferred embodiment, phosphorylated Mabs were accumulated in significantly higher amounts in tumor than those in all of the other organs.

The kinase recognition sequence may be positioned at either termini or other positions of the DNA coding sequence, irrespective of the specific phosphorylated amino acid.

The invention also provides labellable and labeled polypeptides, such as hormones and modified streptavidin. The modified streptavidin can be bound to individual biotinylated antibodies, each streptavidin being modified by single or multiple phosphorylated groups, which results in greatly enhanced radiation and therefore diagnostic and therapeutic potential.

The invention also provides phosphorylatable polypeptides which contain at least one phosphorylation recognition site for protein kinase(s), and which, upon phosphorylation at the said site by kinase(s), contain a particularly stable phosphate group by virtue of its ability to form intramolecular stabilizing interactions with neighboring groups (i.e. amino acids side chains). The intramolecular stabilizing interaction can be charge, hydrophobic and/or other covalent interactions that prevent hydroxy groups from attacking or reaching the phosphate residues. Evaluation of regions of hydrogen bonding serves as a way to locate such regions where phosphates are protected from hydrolysis.

The invention also provides phosphorylated polypeptides which contains at least one phosphate group attached to engineered phosphorylation recognition site(s) for protein kinase(s), and which phosphate group is particularly stable by virtue of its ability to form intramolecular stabilizing interactions with neighboring groups (i.e. amino acids side chains). The intramolecular stabilizing interaction can be charge, hydrophobic, and/or other non-covalent interactions that prevent hydroxy groups from attacking or reaching the phosphate residues. Evaluation of regions of hydrogen bonding serves as a way to locate such regions where phosphates are protected from hydrolysis.

The invention also encompasses recombinant DNA sequences which encode functional polypeptides having one or more putative phosphorylation sites; expression vectors for expressing the functional polypeptide; transformed host cells; methods of expressing the modified polypeptides; and the modified polypeptides.

The invention also provides such MAbs and polypeptides made by recombinant DNA techniques, including MAbs radio-labeled with phosphorus or with sulfur, and recombinant DNA-produced radio-labeled polypeptides and polypeptides.

The invention further provides DNA sequences encoding a functional MAb which possesses one or more labelling sites and is sufficiently duplicative of the unmodified MAb to possess substantially similar affinity for its intended Ag.

Further, there is provided a recombinant-DNA containing a coding sequence for a putative recognition site for a kinase; the recombinant expression vector; the host organisms transformed with the expression vector that includes the DNA sequence; and an expressed modified polypeptide. A method involving site-specific mutagenesis for constructing the appropriate expression vector, a host transformed with the vector and expressing the modified polypeptides, in particular the modified human interferons, is also provided.

The invention provides in one of its several embodiments DNA sequences which encode one or more putative phosphorylation sites, which sequences encode functional MAbs each of which possesses at least one putative phosphorylation site and each of which possesses at least substantially similar affinity for its intended Ag; expression vectors for expression of the functional modified MAb under the control of a suitable promoter such as the lambda $P_L$ promoter or others described hereinafter; and the biologically active phosphorylated MAb.

The invention also provides a kit comprising at least one phosphorylatable polypeptide with at least one engineered phosphorylation site, or polynucleotide sequence encoding the said phosphorylatable polypeptide; at least one protein kinase, or polynucleotide sequence encoding the protein kinase, capable of phosphorylating the polypeptide at the engineered phosphorylation site; and at least one kind of nucleic acid or its derivative that is capable of being used as a substrate by the protein kinase to label the phosphorylatable polypeptide.

Thus, in accordance with the invention, a nucleotide sequence is constructed that codes for the necessary number and specific amino acids required for creating the putative phosphorylation site.

The invention also provides phosphorylatable or phosphorylated polypeptides, either as separate products or as one of the components of certain kits.

The invention also provides a method to analyse biochemical properties of molecules by using molecular modeling tools.

An "internal sequence" of a polypeptide, as used herein, generally denotes that there is at least one amino acid N-terminal corresponding to the first amino acid of said internal polypeptide sequence, and that there is at least one amino acid C-terminal corresponding to the last amino acid of said internal polypeptide sequence.

By "biological activity" is generally meant the intrinsic biochemical and/or biological activities of any given polypeptide, including, but not limited to, such properties as the catalytic activity of enzymes, the ability to bind certain molecules (i.e. other polypeptides, polynucleic acids, metal ions, steroid hormones, lipids, polysaccharides, etc), and ability to activate or inhibit the function of other molecules.

By "engineered" is generally meant that a moleucle is purposefully changed according to certain predetermined criteria, usually by way of site-directed mutagenesis of the polynucleotide sequence encoding the target amino acid sequence, using conventional molecular biology techniques such as PCR and/or subcloning.

The foregoing is not intended to have identified all of the aspects or embodiments of the invention nor in any way to limit the invention. The accompanying drawings and examples, which are incorporated and constitute part of the specification, illustrate various embodiments of the invention, and together with the specification and claims, serve to explain the principles of the invention.

BRIEF DESCRIPTION OF THE DRAWINGS

FIG. 3 depicts the nucleotide (SEQ ID NOs 71–72) and amino acid (SEQ ID NO 73) sequences of the synthetic fragment K2. The two phosphorylation sites recognized by the cAMP-dependent protein kinase is underlined. The cloning site, XmaI, is shown in italics.

FIG. 38 is a comparison of primary sequences of MAb-chCC49, MAb231 and MAb61.1.3 in the hinge region. A: Primary sequences of MAb-chCC49, (SEQ ID NO. 74), MAb231 (SEQ ID NO. 75) and MAb61.1.3 (SEQ ID NO. 76) in the hinge region are aligned. B: Bestfit of primary sequence of MAb-chCC49 (SEQ ID NO. 74) to that of MAb231 (SEQ ID NO. 75) in the hinge region. C: Bestfit of primary sequence MAb-chCC49 (SEQ ID NO. 74) to that of MAb61.1.3 (SEQ ID NO. 76) in the hinge region.

FIG. 39 is a comparison of stabilities of [$^{32}$P]MAb-WW5, [$^{32}$P]MAb-WW6, [$^{32}$P]MAb-WW7 and [$^{32}$P]MAb-chCC49K1 in mouse serum. The percentage of 32P remaining on [$_{32}$P]MAb-WW5, -WW6, -WW7 and [$^{32}$P]MAb-chCC49K1 in mouse serum over a 24-hour period at 37° C. is shown. In the figure, blue symbols represent [$^{32}$P]MAb-WW5; green symbols represent [$^{32}$P]MAb-WW6; pink symbols represent [$^{32}$P]MAb-WW7; black line represents [$^{32}$P]MAb-chCC49K1.

DETAILED DESCRIPTION OF THE INVENTION

Figure 1:
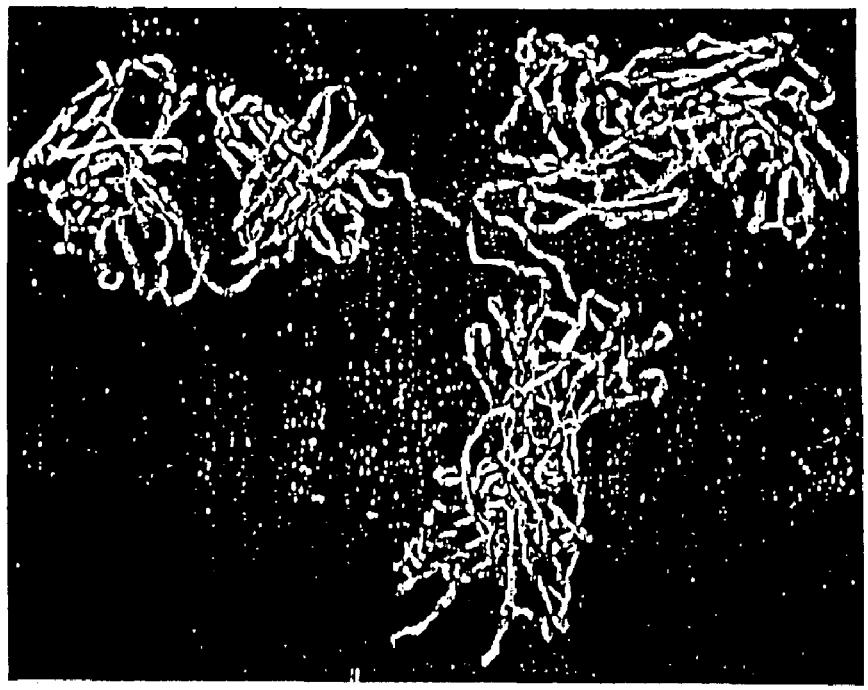
FIG. 1 depicts a model of the MAb-chCC49 antibody. The light chains are shown in yellow, and the heavy chains in green. The violet regions represent the sites where the polypeptide kinase recognition site can be introduced. Altogether, nine sites on the heavy chains and three potential sites on the light chains are shown.

Polypeptides which are normally not phosphorylatable can be modified to render them phosphorylatable (see U.S. Pat. No. 5,986,061, the dislcosure of which is incorporated herein in its entirety). The methodology to achieve this result (especially without loss of the biological activity of the polypeptide of interest) has provided the potential to modify other polypeptides, such as monoclonal antibodies, and render them phosphorylatable. However, selection of ideal putative phosphorylation sites can be tricky, largely due to uncertainties such as unpredictability of the effects of mutagenesis on overall polypeptide structure. Therefore, the improvement described in the instant invention not only helps to alleviate this problem but also has the unexpected advantage of predicting intramolecular interactions between the added phosphate group and its neighbouring groups so that the overall stability of the phosphate group can be predicted. The stability of the attached phosphate group is a critically important parameter for many utilities of the phosphorylatable polypeptide.

One aspect of the present invention concerns three-dimensional molecular models of template polypeptides, and their use for computer-aided modeling of polypeptides of interest. An integral step to this approach to designing phosphorylation sites involves the construction of computer graphics models of the polypeptides of interest and their mutants, which can be used to determine the consequences of introducing those mutations on the overall conformation (and thus, biological activities) of those polypeptides; the effects of phosphate groups on neighbouring groups; and the stability of the attached phosphate groups based on their potential to form intramolecular interactions with neighbouring groups. For instance, for a putative phosphorylation site to be effective, it will generally be desirable that it is exposed on the surface of the polypeptide rather than buried deep within other structures so that there is no steric hindrance and polypeptide kinases can easily have access to the phosphorylation site. Additionally, other factors, including electrostatic interactions, hydrogen bonding, hydrophobic interactions, and desolvation effects, all influence the stability of the attached phosphate group, which is a critical parameter for many utilities of the instant invention. Therefore, all of these factors should be taken into account in attempts to design the ideal putative phosphorylation sites.

As described in the following examples, a computer-generated molecular model of the subject polypeptide can be created. In preferred embodiments, at least the C'''-carbon positions of the MAbs are mapped to a particular coordinate pattern, such as the coordinates for MAb231 shown in FIG. 2, by homology modeling. Typically, such a protocol involves primarily the prediction of side-chain conformations in the modeled polypeptide, while assuming a main-chain trace taken from a tertiary structure such as provided in FIGS. 1 and 2. Computer programs for performing energy minimization routines are commonly used to generate molecular models. For example, both the CHARMM (Brooks et al. (1983) *J Comput Chem* 4:187–217) and AMBER (Weiner et al (1981) *J. Comput. Chem.* 106:765) algorithms handle all of the molecular system setup, force field calculation, and analysis (see also, Eisenfield et al. (1991) *Am J Physiol* 261:C376–386; Lybrand (1991) *J Pharm Belg* 46:49–54; Froimowitz (1990) *Biotechniques* 8:640–644; Burbam et al. (1990) *Polypeptides* 7:99–111; Pedersen (1985) *Environ Health Perspect* 61:185–190; and Kini et al. (1991) *J Biomol Struct Dyn* 9:475–488). The disclosure of these references are incorporated herein in their entireties.

At the heart of these programs is a set of subroutines that, given the position of every atom in the model, calculate the total potential energy of the system and the force on each atom. These programs may utilize a starting set of atomic coordinates, such as the model coordinates provided in FIG. 1 or 2, the parameters for the various terms of the potential energy function, and a description of the molecular topology (the covalent structure). Common features of such molecular modeling methods include: provisions for handling hydrogen bonds and other constraint forces; the use of periodic boundary conditions; and provisions for occasionally adjusting positions, velocities, or other parameters in order to maintain or change temperature, pressure, volume, forces of constraint, or other externally controlled conditions.

Most conventional energy minimization methods use the input data described above and the fact that the potential energy function is an explicit, differentiable function of Cartesian coordinates, to calculate the potential energy and its gradient (which gives the force on each atom) for any set of atomic positions. This information can be used to generate a new set of coordinates in an effort to reduce the total potential energy and, by repeating this process over and over, to optimize the molecular structure under a given set of external conditions. These energy minimization methods are routinely applied to molecules similar to the subject polypeptides as well as nucleic acids, polymers and zeolites.

In general, energy minimization methods can be carried out for a given temperature, $T_i$, which may be different than the docking simulation temperature, $T_o$. Upon energy minimization of the molecule at $T_i$, coordinates and velocities of all the atoms in the system are computed. Additionally, the normal modes of the system are calculated. It will be appreciated by those skilled in the art that each normal mode is a collective, periodic motion, with all parts of the system moving in phase with each other, and that the motion of the molecule is the superposition of all normal modes. For a given temperature, the mean square amplitude of motion in a particular mode is inversely proportional to the effective force constant for that mode, so that the motion of the molecule will often be dominated by the low frequency vibrations.

After the molecular model has been energy minimized at $T_i$, the system is "heated" or "cooled" to the simulation temperature, $T_o$, by carrying out an equilibration run where the velocities of the atoms are scaled in a step-wise manner until the desired temperature $T_o$ is reached. The system is further equilibrated for a specified period of time until certain properties of the system, such as average kinetic energy, remain constant. The coordinates and velocities of each atom are then obtained from the equilibrated system.

Further energy minimization routines can also be carried out. For example, a second class of methods involves calculating approximate solutions to the constrained EOM for the polypeptide. These methods use an iterative approach to solve for the Lagrange multipliers and, typically, only need a few iterations if the corrections required are small. The most popular method of this type, SHAKE (Ryckaert et al. (1977) *J Comput Phys* 23:327; and Van Gunsteren et al. (1977) *Mol Phys* 34:1311) is easy to implement and scales as O(N) as the number of constraints increases. Therefore, the method is applicable to macromolecules such as the polypeptides of the present invention. An alternative method, RATTLE (Anderson (1983) *J Comput Phys* 52:24) is based on the velocity version of the Verlet algorithm. Like SHAKE, RATTLE is an iterative algorithm and can be used to energy minimize the model of the subject polypeptide. These references are incorporated herein in their entireties.

From the above observation, the same-principles are applicable to construct any amino acid sequences other than the particular amino acid recognition sequence illustrated above.

In the situations where the phosphorylation site is other than serine (as illustrated above), the DNA sequence codes for part or all of the appropriate amino acid sequence containing the putative recognition site containing threonine, tyrosine, etc. Thus, where in any particular 40 polypeptide one or more amino acids (at any position of the amino acid sequence) are the same as that of an amino acid recognition sequence for a kinase, it is sufficient to add (or modify) those complementary amino acids of the amino acid recognition sequence to complete that sequence. This is accomplished by constructing a DNA sequence which codes for the desired amino acid sequence. There may indeed be situations where such addition (or modification) is a more desirable procedure as where it is important to retain the integrity of the polypeptide molecule to be modified (for instance, to minimize risks of affecting a particular activity, e.g., biological), or for simplicity of the genetic manipulations, or because either or both termini or other positions are more accessible.

In accordance with the invention, phosphorylation of the phosphorylatable site of the polypeptide can be performed by any suitable phosphorylation means. Phosphorylation and dephosphorylation of polypeptides catalyzed by polypeptide kinases and polypeptide phosphatases is known to affect a vast array of polypeptides. A large number of polypeptide kinases have been described and are available to one skilled in the art for use in the invention. Such polypeptide kinases may be divided into two major groups: those that catalyze the phosphorylation of serine and/or threonine residues in polypeptides and peptides and those that catalyze the phosphorylation of tyrosine residues. These two major categories can be subdivided into additional groups. For example, the serine/threonine polypeptide kinases can be subdivided into cyclic AMP (cAMP)-dependent polypeptide kinases, cyclic GMP (cGMP)-dependent kinases, and cyclic nucleotide-independent polypeptide kinases. The recognition sites for many of the polypeptide kinases have been deduced.

In short synthetic peptides cAMP-dependent polypeptide kinase recognize the sequence Arg-Arg-Xxx-Ser-Xxx, where Xxx represents an amino acid. As noted above, the cAMP-dependent polypeptide kinase recognizes the amino acid sequence Arg-Arg-Xxx-Ser-xxx, but also can recognize some other specific sequences such as Arg-Thr-Lys-Arg-Ser- Gly-Ser-Val, (SEQUENCE ID NO. 3). Many other polypeptide serine/threonine kinases have been reported such as glycogen synthase kinase, phosphorylase kinase, casein kinases I and II, pyruvate dehydrogenase kinase, polypeptide kinase C, and myosin light chain kinase.

Polypeptide kinases which phosphorylate and exhibit specificity for tyrosine (rather than for serine, threonine, or hydroxyproline) in peptide substrates are the polypeptide tyrosine kinases (PTK). Such PTKs are described in the literature. The PTKs are another class of kinases available for use in the invention.

Another available class of kinases are the cyclic GMP-dependent (cGMP-dependent) polypeptide kinases. The cGMP-dependent polypeptide kinases exhibit substrate specificity similar to, but not identical to the specificity exhibited by cAMP-dependent polypeptide kinases. The peptide Arg-Lys-Arg-Ser-Arg-Lys-Glu, (SEQUENCE ID NO. 4) is phosphorylated at serine by the cGMP-dependent polypeptide kinase better than by the cAMP-dependent polypeptide kinase. It has also been shown that the cAMP-dependent polypeptide kinase can phosphorylate hydroxyproline in the synthetic peptide Leu-Arg-Arg-Ala-Hyp-Leu-Gly, (SEQUENCE ID NO. 5).

Casein kinases, widely distributed among eukaryotic organisms and preferentially utilizing acidic polypeptides such as casein as substrates, have been classified into two groups, casein kinases I and II. Casein kinase II phosphorylated the synthetic peptide Ser-Glu-Glu-Glu-Glu-Glu, (SEQUENCE ID NO. 6). Evaluation of results with synthetic peptides and natural polypeptide substrates reveals that a relatively short sequence of amino acids surrounding the phosphate acceptor site provides the basis for the specificity of casein kinase II. Accordingly, the acidic residues at positions 3 and 5 to the carboxyl-terminal side of the serine seem to be the most important. Serine is preferentially phosphorylated compared to threonine. In another study, the peptide Arg-Arg-Arg-Glu-Glu-Glu-Thr-Glu-Glu-Glu, (SEQUENCE ID NO. 7) is found to be a specific substrate for casein kinase II; however, Arg-Arg-Arg-Glu-Glu-Glu-Ser-Glu-Glu-Glu, (SEQUENCE ID NO. 8) is a better substrate; and Arg-Arg-Arg-Asp-Asp-Asp-Ser-Asp-Asp-Asp, is a better substrate than Arg-Arg-Arg-Glu-Glu-Glu-Ser-Glu-Glu-Glu, (SEQUENCE ID NO. 9). Thus, aspartate is preferred over glutamate. Acidic residues on the COOH-terrninal side of the serine (threonine) are as far as known today absolutely required; acidic residues on the amino-terminal side of the serine (threonine) enhance phosphorylation, but are not absolutely required: thus, Ala-Ala-Ala-Ala-Ala-Ala-Ser(Thr)-Glu-Glu-Glu, (SEQUENCE ID NO. 10) served as a substrate for casein kinase II, but is less effective than Ala-Ala-Ala-Glu-Glu-Glu-Ser(Thr)-Glu-Glu-Glu, (SEQUENCE ID NO. 11) (the designation Ser(Thr) means serine or threonine). Casein kinases I and II phosphorylate many of the same substrates although casein kinase I does not phosphorylate any of the decamer peptide substrates noted here. It is concluded from studies with a variety of synthetic peptides that the sequence Ser-Xxx-Xxx-Glu (and by inference Ser-Xxx-Xxx-Asp) may represent one class of sequences that fulfill the minimal requirements for recognition by casein kinase II although some other peptides and sequences may also suffice.

As noted above, other kinases are described. The mitogen-activated S6 kinase phosphorylates the synthetic peptide Arg-Arg-Leu-Ser-Ser-Leu-Arg-Ala, (SEQUENCE ID NO. 12) as does a protease-activated kinase from liver. The rhodopsin kinase catalyzes the phosphorylation of the peptide Thr-Glu-Thr-Ser-Gln-Val-Ala-Pro-Ala, (SEQUENCE ID NO. 13). Other polypeptide serine/threonine kinases are described and their sites of phosphorylation elucidated.

Thus, one skilled in the art has quite an adequate selection of available kinases for use in the invention, which have relatively high specificity with respect to the recognition process, but some flexibility to the specific sequence of the amino acid recognition site. Such kinases provide means for phosphorylation of putative phosphorylation sites in the desired polypeptides.

The selection of the position of the molecule best suited for the modification depends on the particular polypeptide (and its configuration). Where multiple putative phosphorylation sites (and phosphorylatable sites) are to be included in the modified polypeptide, one would consider the potential availability of either or both ends and other positions of the molecule for providing the amino acid recognition sequence. Thus, in accordance with the invention, phosphorylation recognition sequences can be introduced at any point in a naturally occurring polypeptide sequence providing such introduced sequences do not adversely affect biological activity where such activity is desired.

Once the recognition site for a particular polypeptide kinase is identified, the invention provides a method for making by recombinant-DNA techniques the DNA sequence which encodes the recognition site for that kinase within, fused or linked to the DNA sequence encoding the functional polypeptide which is to contain the corresponding putative labelling site. Due to the intrinsic advantage of the instant invention, molecular modeling can be used to quickly scan through a number of potential sites so that only those sites, with or without the attached phosphate group, that will not adversely affect the three-dimentional structure and/or biological activity of the target polypeptide will be selected for further consideration.

The invention contemplates and includes any polypeptide which is radio-labellable by the methods of this invention and which possesses at least one of the properties of the corresponding unlabeled (or unlabellable) polypeptide. In accordance with the invention, the non-phosphorylated (or non-phosphorylatable) polypeptide is modified to introduce into the amino acid sequence the putative phosphorylatable site; this is performed after having modified the DNA sequence encoding the amino acid sequence of the polypeptide with the DNA sequence (part or all) which codes for the putative phosphorylated site. In the case of MAb, the invention embraces all MAbs, including such structurally modified MAb species which have been reported in the literature (such as humanized MAbs, hybrid antibodies, chimeric antibodies, and modified MAb Fab or Fc fragments) as discussed above, and other modified MAbs which will be developed in the future.

In a preferred embodiment of the instant invention, recognition sites for the cAMP-dependent polypeptide kinase is introduced into the MAb-chCC49 by site-directed mutation of the coding sequence to make variants of MAb-chCC49 to be able to contain highly stable phosphate groups. To design those MAbs without changing their immunoreactivity or biological properties, molecular modeling is used to locate appropriate regions for introduction of the cAMP-dependent phosphorylation site with desirable properties. With the use of molecular modeling, we chose positions on the heavy chain to mutate. Vectors expressing the mutants are constructed and transfected into mouse myeloma NS0 cells that expressed a high level of the resultant MAb-WW5, -WW6 and -WW7. Those variants contain the cAMP-dependent phosphorylation site at the hinge region of the heavy chain, and can be phosphorylated by the catalytic subunit of cAMP-dependent polypeptide kinase with [$\gamma$-$^{32}$P]ATP to high specific activity and retains the phosphate stably. Compared to MAb-chCC49K1 (Lin et al., *Int. J. oncology*, 13, 115–120, 1998), another phosphorylatable variant of MAb-chCC49, the phosphate attached to MAb-WW5, -WW6 and -WW7 show much improved stability: about a ten-fold increase in resistance to hydrolysis. They also exhibit the same binding specificity to the TAG-72 antigen on MCF-7 4C10 breast cancer cells observed with MAb-chCC49K1. The improved stability of the attached phosphate provides a MAb with potential to be used in diagnosis and therapy of adenocarcinomas.

Radio labeled monoclonal antibodies (MAbs) against tumor-associated antigens (TAA) are used clinically for the early detection and staging of the disease as well as for therapy. Chimeric MAb-chCC49 is one of these MAbs which reacts with the TAA expressed on the surface of a wide range of human adenocarcinomas. It consists of the variable region from mouse MAb-CC49 (GenBank Accession No: M95575) and the constant region from the human IgG1 heavy chain (GenBank Accession No: J00228) and the human chain (GenBank Accession No: J00241).

Since molecular modeling is a powerful tool to build 3-D models of polypeptides, an alternative way to obtain structural information about MAb-chCC49 is to build a 3-D model by using the crystal structures of the known MAbs as a template. This report provides a summary of the development of a 3-D model of MAb-chCC49 and its variants, and the use of the 3-D model to design a phosphorylatable MAb-chCC49 mutant where the phosphate exhibits increased resistance to hydrolysis. The phosphorylatable MAb-chCC49 designated MAb-WW5 can be phosphorylated easily and the attached phosphate is resistant to hydrolysis, making it a suitable candidate for use in vivo as well as in animal models and in patients.

Accordingly, to develop a more effective radio labeled MAb, a recognition site for the cAMP-dependent polypeptide kinase is introduced into the MAb-chCC49 by site-directed mutation of the coding sequence with the goal of developing stable and effective radio labeled MAbs for in vivo utilization.

To make variants of MAb-chCC49 without changing their immunoreactivity or biological properties, it was useful to know the structures of these mutant antibodies. However, due to the intrinsic mobility and segmental flexibility of antibodies, it is extremely difficult to obtain the crystal structure of an intact antibody. The original crystal structures of two myeloma polypeptides, Dob and Mcg are solved by deletion of the hinge region. Conformationally constrained, the structures show a compact T shape. In addition, the structure of the MAb Kol is determined. Although, it has the complete hinge region, the Fc portion of the MAb is too distorted to be oriented with respect to the Fab component. So far crystal structures of only two MAbs have been solved. One is MAb23 1, a mouse IgG2a MAb against canine lymphoma cells. The other is MAb61.1.3, a murine IgG1 MAb against phenobarbital. The crystal structures of both of these MAbs resolve the structure of the Fab, hinge, and Fc regions and their spatial orientation. In addition, both show an overall asymmetry, which might manifest a considerable degree of intrinsic mobility and segmental flexibility of the antibodies. Other structural features of the two MAbs are quite different.

The following examples illustrate two preferred embodiments of the instant invention.

EXAMPLE 1

Example 1 is intended to show the generation of WW-series of phosphorylated monoclonal antibodies that are much more stable than other phosphorylated monoclonal antibodies.

I. Materials and Methods

A. Enzymes, Reagents and Chemicals

1. Enzymes

All restriction endonucleases, the Klenow fragment of DNA polymerase I were purchased from New England Biolabs, Gibco/BRL Life Technologies, or Boehringer-Mannheim Biochemicals. The catalytic subunit of the cAMP-dependent protein kinase from bovine heart (Cat. No. P-2645) was purchased from Sigma Chemical Co.

2. Reagents

Goat anti-human IgG (Fc specific) antibody (Cat. No. I-2136) was purchased from Sigma Chemical Co. Mouse serum (Cat. No. 015-000-120) was purchased from Jackson ImmunoResearch Laboratories, Inc. The Geneclean kit (Cat. No. 3106) was purchased from Bio101. PFHM-II protein-free hybridoma medium was purchased from Gibco/BRL (Cat. No. 12040-077). Iscove's Modified Dulbecco's Medium was purchased from Gibco BRL (Cat. No. 1057861).

3. Chemicals

Sodium Pyruvate (Cat. No. 11360-013), L-Glutamine (Cat. No. 25030-016) and Nonessential amino acids (Cat. No. 11140-019) were purchased from Gibco/BRL. Insulin (Cat. No. I-5500) and methotrexate (Cat. No. A-6770) were purchased from Sigma Chemical Co. Uridine (Cat. No. U288-1) was purchased from Aldrich Chemical Company. Radionucleotide [$\gamma$-$^{32}$P]ATP, 6000 Ci/mmol, was purchased from DuPont/NEN. All other analytical grade chemicals were purchased from Fisher or United States Biochemical Co.

B. Cell Lines and Bacterial Strains

1. Cell Lines

The designations in parenthesis after each of the cell names represent the American Type Culture Collection (ATCC) number where applicable.

a. NS0 cells: A mouse myeloma cell line. The cells are grown in Dulbecco's Modified Eagle Medium (DMEM), 10% Fetal Bovine Serum (FBS) and 2 mg/ml L-glutamine.

b. WISH cells (CCL-25): Description taken from the ATCC catalog: "This line was originally thought to be derived from normal amnion, but was subsequently found, based on isoenzyme analysis, HeLa marker chromosomes, and DNA fingerprinting, to have been established via HeLa cell contamination. The cells are positive for keratin by immunoperoxidase staining." The cells are grown in DMEM with 10% FBS. WISH cells are susceptible to VSV, poliovirus type 1, 2, and adenovirus type 2.

c. FS7 cells: Human foreskin cells with a finite life of about twenty passages. The cells are grown in DMEM with 10% FBS.

d. HeLa S3 cells (CCL-2.2): A human cervical epithelial adenocarcinoma cell line. The cells are grown in DMEM with 5% FBS. HeLa S3 cells are susceptible to VSV, poliovirus type 1, 2 and 3, adenovirus type 5, and interferon.

e. HEp-2 cells (CCL-23): Description taken from the ATCC catalog: "This line was originally thought to be derived from an epidermoid carcinoma of the larynx, but was subsequently found, based on isoenzyme analysis, HeLa marker chromosomes, and DNA fingerprinting, to have been established via HeLa cell contamination. The cells are positive for keratin by immunoperoxidase staining." The cells are grown in DMEM with 10% FBS. HEp-2 cells are susceptible to VSV, poliovirus type 1, and adenovirus type 3.

f. MDBK cells (CCL-22): A bovine kidney epithelial cell line. The cells are grown in DMEM with 10% FBS. MDBK cells are susceptible to VSV, and several other bovine viruses.

g. Vero cells (CCL-81): A monkey kidney epithelial cell line. The cells are grown in DMEM with 10% FBS. Vero cells are susceptible to VSV, poliovirus type 1, 2 and 3, simian adenoviruses.

h. Daudi cells (CCL-213): A human peripheral blood cell line. The cells are grown in RPMI with 10% FBS. The cells express Fc receptors on the surface.

i. MCF-7 4C10 cells (HTB-22): A subclone of the human breast epithelial adenocarcinoma cell line MCF-7. The cells are grown in DMEM, 10% FBS, 0.05 mg/ml insulin, 0.5× nonessential amino acids and 0.05 mg/ml sodium pyruvate. The cells express TAG-72 tumor antigen on the surface.

2. Bacterial Stains

DH5αF': It has genotype of F' φ80dlacZΔM15 Δ(lacXYA-argF)U169 deoR recA1 endA1 hsdR 17 ($r_K^-, m_K^+$) supE44 λ⁻thi-1 gyrA96 relA1. DH5αF' was used as a host for the M13mp cloning vectors and also for the growth of the plasmids.

C. Homology Modeling of MAb-chCC49

Software and Hardware

In the present study we used the SYBYL molecular modeling package (version 6.5; Tripos Association, St. Louis, Mo., 1999) for structural analysis and geometry refinement. Most of the homology and mutant modeling was performed with the LOOK 3.5 program (Molecular Application Group, Palo Alto, Calif.). For the geometry optimization we used Kollman united charges, molecular mechanics force field and the MAXIMIN2 minimizer of SYBYL. All these visualization analyses and simulations were performed on Silicon Graphics Octane workstations.

2. Template

The crystal structure of the intact MAb231, the coordinates of which were generously provided by Dr. Alexander McPherson and Dr. Lisa J. Harris, was used as template to model MAb-chCC49. These coordinates are now available from the Protein Data Bank (PDB) as ID 1IGT. Because the crystal structure of MAb231 was the only one available for an intact antibody at the time we started this project, we used MAb231 as the template for modeling in this study. In addition, after the crystal structure of MAb61.1.3 was reported, we noted that the length and sequence of the hinge region of MAb231 was more similar to the hinge region of MAb-chCC49 than that of MAb61.1.3, so we used the hinge region of MAb231 to model MAb-chCC49. The resulting model of MAb-chCC49 was then used as template to model the MAb-chCC49 mutants.

3. Overall Procedure

Figure 2:
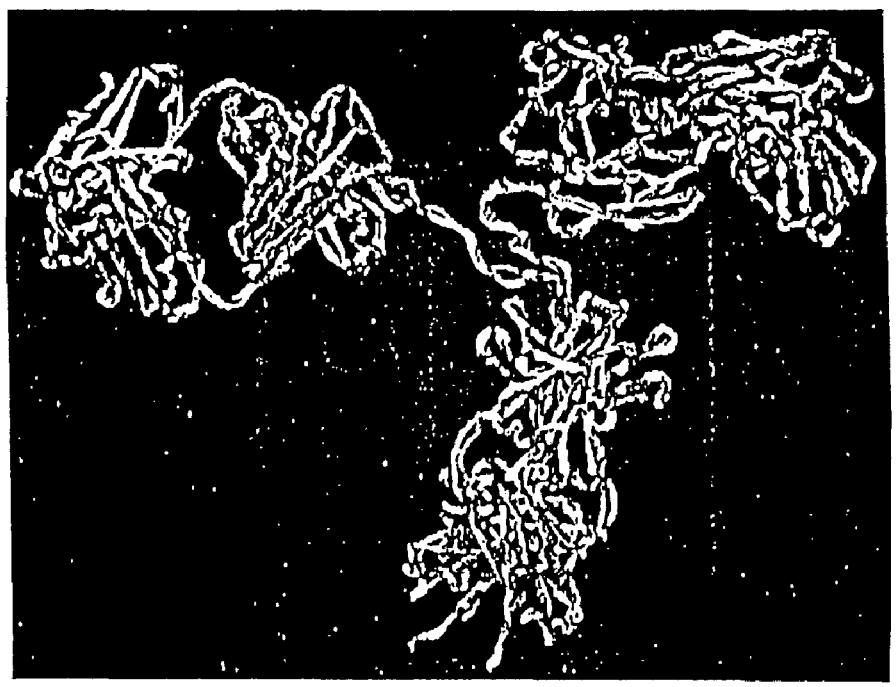
FIG. 2 depcits a comparison of the modeled MAb-chCC49 and MAb231 antidobies. The light chains of MAb-chCC49 are shown in yellow, the heavy chains in green. MAb231 is shown in white.

The model of MAb-chCC49 was built with the homology modeling module of the LOOK3.5 program. After the coordinates of IgG2a MAb231 were obtained, the structure of MAb231 was used as template to develop a molecular model of MAb-chCC49. First, the four chains of MAb231 were separated individually and designated as L1, L2, H1, and H2 (L for light chain and H for heavy chain). The coordinates of each chain were extracted and saved separately. The strategy we used to build a model of MAb-chCC49 was to do homology modeling on each chain of MAb-chCC49, separately. We first displayed the 3-D structure of chain L1 of MAb231, then the sequence of the light chain of MAb-chCC49 was introduced into the program and the automatic alignment mode was set up to align the sequence of the MAb-chCC49 light chain with that of the sequence of MAb231 light chain (FIG. 1). The model was built with the program module SEGMOD under the automated method with full refinement. The coordinates of chain L1 of MAb-chCC49 were thereafter generated and saved as a PDB file. The models and coordinates of chains L2, H1, and H2 of MAb-chCC49 were generated by the same procedure as described above.

4. Geometry Refinement and Energy Minimization.

Further geometry refinement and optimization was done with SYBYL molecular modeling software. The 3-D structure of chain L1 of MAb-chCC49, the coordinates of which were generated as described above, was displayed. We added the essential hydrogen atoms (hydrogen atoms attached to nitrogen, oxygen, and/or sulfur atoms that could potentially be involved in hydrogen binding with surrounding atoms/residues). In the first step, we scanned the side chain to minimize conformational strains, if any, within side chain groups and surrounding residues. Proline is the only residue that contains a ring in its backbone and it adopts a phi angle close to 70°. Therefore, we used the "fix-proline" command in SYBYL to maintain proline geometry. We also scanned the orientations of the amide groups of Asn and Gln to favor potential hydrogen bonding with surrounding residues. Finally, the Kollman united charges were loaded on chain L1 so that the electrostatic contribution in the energy calculation could be included. The 3-D structures of chain L2, H1, H2 were geometrically refined and optimized by the same procedure as used for chain L1. Then the refined models of chains L1, L2, H1, and H2 of MAb-chCC49 were merged into a single molecule. Afterwards, the side chains, as well as the amide groups of Asn and Gln, were fixed to relax the strain in the composite molecule.

Since MAb-chCC49 is a large protein, the energy minimization step was broken into two parts. Before energy minimization of the whole molecule, we carried out minimization of the side chains first. We fixed the backbone by making it an aggregate set. Then energy minimization of the side chains was achieved with the Kollman united force field option for 100 iterations. In the next step, the aggregate was deleted, and energy minimization of the whole molecule was done by the Powell method in the SYBYL program.

D. Construction of Phosphorylatable Chimeric Monoclonal Antibodies of MAb-cbCC49-6P, MAb-WW1, MAb-WW2, MAb-WW3, MAb-WW4, MAb-WW5, MAb-WW6 and MAb-WW7

1. Homology Modeling of MAb-chCC49K1, MAb-CC49CKI, MAb-CC49CKII, MAb-CC49Tyr, MAb-chCC49-6P, MAb-WW1, MAb-WW2, MAb-WW3, MAb-WW4, MAb-WW5, MAb-WW6, MAb-WW7 and MAb-WW8

This procedure was similar to modeling of MAb-chCC49 as discussed earlier in Section C. Both chains of MAb-chCC49K1, MAb-CC49CKI, MAb-CC49CKII, MAb-CC49Tyr, MAb-chCC49-6P, MAb-WW1, -WW2, -WW3, -WW4, -WW5, -WW6, -WW7 and -WW8 were modeled using the corresponding chain of MAb-chCC49 as template. Geometry refinement and energy minimization of the modeled modified MAbs were carried out in the same way as we did to obtain the refined model of MAb-chCC49.

2. Systematic Search and Modeling of Phosphorylated MAb-chCC49K1, MAb-CC49CKI, MAb-CC49CKII, MAb-CC49Tyr, MAb-chCC49-6P, MAb-WW1, MAb-WW2, MAb-WW3, MAb-WW4, MAb-WW5, MAb-WW6, MAb-WW7 and MAb-WW8

After the model of each modified MAb was obtained, a phosphate group was generated and attached to the hydroxyl group of serine or threonine in the PKA recognition site with the 'builder' module of the SYBYL modeling package. For MAb-chCC49K1, the phosphate groups were attached to Ser449 and Ser455; for MAb-chCC49-6P, to Ser449, Ser455, Ser464, Ser470, Ser479 and Ser485; for MAb-CC49CKI, to Ser450 and Ser457; for MAb-CC49CKII, to Ser436; for MAb-CC49Tyr, to Tyr455; for MAb-WW1, to Ser123; for MAb-WW2, to Thr224; for MAb-WW3, to Ser21; for MAb-WW4, to Thr20; for MAb-WW5, to Ser224; for MAb-WW6, to Ser224; for MAb-WW7, to Ser224; for MAb-WW8, to Ser224. To obtain the optimal position and to generate favorable interaction with surrounding residues of the phosphate moiety, we performed a systematic conformational search along Cα-Cβ and Cβ-Cγ of Ser/Thr of the PKA recognition site. For each allowed conformation of the Ser or Thr side chain, we analyzed for optimal hydrogen bonding geometry with the surrounding residues. Then among these conformations, we chose the one in which the entire molecule has the lowest inherent energy to do further refinement. First we defined a subset of amino acid residues falling within a 7 Å sphere around the residues RRXS/T of each protein kinase recognition site. Then the minimization subset for these four amino acid residues (RRXS/T) was done for 100 iterations by the Powell method.

3. Construction of MAb-chCC49-6P, MAb-WW1, MAb-WW2, MAb-WW3, MAb-WW4, MAb-WW5, MAb-WW6, MAb-WW7 and MAb-WW8 a. Construction of MAb-chCC49-6P

The plasmid pdHL7-CC49K1 made previously was used to make plasmid pdHL7-CC49-6P. The MAb-chCC49K1 contains two phosphorylation sites on each heavy chain. To construct a heavy chain with a cassette of six phosphorylation sites, the synthetic fragment K2 was synthesized (FIG. 3). This fragment contained two phosphorylation sites as did fragment K1, but contained overhangs that were compatible with XmaI sites at each end. The XmaI site on the right was modified by replacing the terminal C to A. Thus, when the right end was ligated to an overhang with an XmaI site, the religated product could not be cleaved with endonuclease XmaI. This double-stranded fragment was ligated into the XmaI site of the plasmid pdHL7-CC49K1. Clones containing the insert were screened by digesting the resultant plasmids with XhoI. Clones with XhoI fragments that appeared to contain two K2 fragments were chosen for further screening by PCR. The resultant plasmid pdHL7-CC49-6P contained two intact K2 fragments and the original K1 fragment to generate a sequence encoding six phosphorylation sites on each heavy chain.

The vector pdHL7-CC49K1 for expression of the phosphorylatable monoclonal antibody (MAb-chCC49K1) with two cAMP-dependent protein kinase recognition sites on each heavy chain was modified as follows to construct site-specific mutations to introduce phosphorylation sites in various positions of MAb-CC49. To construct the expression vector for MAb-chCC49 without the phosphokinase recognition site, an intermediate vector pdHL7-BH was made so that one of two XhoI restriction sites in pdHL7-CC49K1 could be removed. To construct pdHL7-BH, the vector pdHL7-CC49K1 was digested with BamHI and HindIII restriction endonucleases. The resultant 6854 bp fragment was isolated by agarose gel electrophoresis, then purified, blunt-ended, and self-ligated to generate intermediate vector pdHL7-BH. To construct pdHL7-CC49, a 358 bp fragment was amplified from pdHL7-CC49K1 by PCR with the 5' and 3' primers GTGACCGCTGTACCAACCTCTGTCC, (SEQUENCE ID NO. 14) and CCCTCGAGTCACTTGC-CCGGGGACAGGGAGAGG, (SEQUENCE ID NO. 15) respectively. This PCR fragment was then digested with BsrGI and XhoI restriction endonucleases, and purified. The vector pdHL7-BH was digested with the same restriction endonucleases and a 6463 bp fragment was released, purified and ligated to the digested and purified 358 bp PCR fragment. The resultant plasmid pdHL7-CC49BH was then digested with XmaI and EcoRI restriction endonucleases, and yielded two bands. The smaller band, which was 2726 bp, was isolated and purified, then further ligated to the 6667 bp fragment which was isolated and purified after pdHL7-CC49K1 was digested with the same restriction endonucleases. The resultant construct pdHL7-CC49 was characterized by BsrGI and XhoI restriction endonuclease digestion and DNA sequencing.

b. Construction of MAb-WW1

To construct plasmid pWW1, the vector pdHL7-CC49 was digested with HindIII and PstI restriction endonucleases to isolate a 890 bp fragment. The fragment was isolated by agarose gel electrophoresis, then purified. The replicative form (RF) DNA of phage M13mp18 was digested with HindIII and PstI restriction endonucleases and the large DNA fragment isolated. The 890 bp fragment was then inserted into the HindIII and PstI site of the M13mp18 DNA to yield phage M13-W21. Then site-directed mutagenesis was performed as described. Phage M13-W21 was introduced into the *Escherichia coli* CJ236 strain, which is a dut, ung strain and lacks the enzyme uracil N-glycosylase which normally removes uracil from DNA. This results in incorporation of uridine in the DNA. Then single-stranded (SS)-DNA containing uridine from phage M13-W21 was used as template for site-directed mutagenesis to prepare the mutant M13-WW1. The oligodeoxynucleotide m120, 5'-GCAGC-CTCCACCAGGCGCCCATCGGTC-3', (SEQUENCE ID NO. 16) was used for site-directed mutagenesis. Oligonucleotide m120 contains a phosphokinase recognition site RRPS and also a NarI recognition site. Oligonucleotide m120 was annealed to uridine-containing SS-DNA of phage M13-WW21, followed by the in vitro synthesis of the complementary strand. Afterwards, the resultant double-stranded (DS)-DNA was transformed into *E. coli* DH5αF' strain with a functional uracil N-glycosylase to remove the parental strand. The desired mutant was characterized by NarI restriction endonuclease digestion and DNA sequencing. Thus we obtained the construct M13-WW1. Then RF-DNA of phage M13-WW1 was digested with HindIII and BstEII restriction endonucleases, and the resultant 410 bp fragment was inserted into the vector pCC49 that was digested with the same endonucleases to yield plasmid pWW1. The vector pWW1 expresses the MAb-WW1 with amino acid substitutions K120R and G121R in the MAb-chCC49 heavy chain.

c. Construction of MAb-WW2

To construct plasmid pWW2, the vector pCC49 was digested with HindIII and NaeI restriction endonucleases to isolate a 1424 bp fragment. The fragment was isolated by agarose gel electrophoresis, then purified. The replicative form (RF) DNA of phage M13mp19 was first digested with XbaI restriction endonuclease, then blunt-ended by Klenow fragment of DNA polymerase. Afterwards, this DNA was further digested with HindIII restriction endonuclease, and the large DNA fragment was isolated. The 1424 bp fragment was then inserted into the XbaI blunt-ended and HindIII site of the M13mp19 DNA to yield phage M13-W22. Then site-directed mutagenesis was performed as described. Phage M13-W22 was introduced into the *E. coli* CJ236 strain and SS-DNA containing uridine from phage M13-

W22 was used as template for site-directed mutagenesis to prepare the mutant M13-WW2. The oligodeoxynucleotide m221rev, 5'-GGGCATGTGTGACGTCTGTCACAA-GATTTG-3', SEQUENCE ID NO. 17 was used for site-directed mutagenesis. Oligonucleotide m221rev contains a phosphokinase recognition site RRHT and also an AatII recognition site. Oligonucleotide m221rev was annealed to uridine-containing SS-DNA of phage M13-WW22, followed by the in vitro synthesis of the complementary strand. Afterwards, the resultant DS-DNA was transformed into *E. coli* DH5αF' strain with a functional uracil N-glycosylase to remove the parental strand. The desired mutant was characterized by AatII restriction endonuclease digestion and DNA sequencing. Thus we obtained the construct M13-WW2. Then RF-DNA of phage M13-WW2 was digested with SacII restriction endonuclease, and the resultant 410 bp fragment was inserted into the vector pCC49 that was digested with the same endonuclease to yield plasmid pWW2. The vector pWW2 expresses the MAb-WW2 with amino acid substitutions K221R and T222R in the MAb-chCC49 heavy chain.

d. Construction of MAb-WW3

To construct plasmid pWW3, the vector pCC49 was digested with HindIII and SnaBI restriction endonucleases to isolate a 708 bp fragment. The fragment was isolated by agarose gel electrophoresis, then purified. The replicative form (RF) DNA of phage M13mp19 was first digested with XbaI restriction endonuclease, then blunt-ended by Klenow fragment of DNA polymerase. Afterwards, this DNA was further digested with HindIII restriction endonuclease, and the large DNA fragment was isolated. The 708 bp fragment was then inserted into the XbaI blunt-ended and HindIII site of the M13mp19 DNA to yield phage M13-W23. Then site-directed mutagenesis was performed as described. Phage M13-W23 was introduced into the *E. coli* CJ236 strain and SS-DNA containing uridine from phage M13-W23 was used as template for site-directed mutagenesis to prepare the mutant M13-WW3. The oligodeoxynucleotide m18rev, 5'-CCTGGGGCTTCGCGAAGGATTTCCTG-CAAGG-3', (SEQUENCE ID NO. 18) was used for site-directed mutagenesis. Oligonucleotide m18rev contains a phosphokinase recognition site RRIS and also a NruI recognition site. Oligonucleotide m18rev was annealed to uridine-containing SS-DNA of phage M13-WW23, followed by the in vitro synthesis of the complementary strand. Afterwards, the resultant DS-DNA was transformed into *E. coli* DH5αF' strain with a functional uracil N-glycosylase to remove the parental strand. The desired mutant was characterized by NruI restriction endonuclease digestion and DNA sequencing. Thus we obtained the construct M13-WW3. Then RF-DNA of phage M13-WW3 was digested with XhoI and HindIII restriction endonucleases, and the resultant 420 bp fragment was first inserted into the intermediate vector pdHL7-BB that was digested with the same endonucleases to yield plasmid pCC49t-WW3. Then pCC49t-WW3 was digested with XbaI, and HindIII restriction endonucleases, and the resultant 2983 bp fragment was isolated. The vector pCC49 was digested with the same endonucleases and large fragment of 6440 bp was isolated. The 2983 bp fragment was ligated to this 6440 bp of the vector fragment to yield plasmid pWW3. The vector pWW3 expresses the MAb-WW3 with amino acid substitutions V18R and K19R in the MAb-chCC49 heavy chain.

e. Construction of MAb-WW4

To construct plasmid pWW4, the vector pCC49 was digested with XbaI and BamHI restriction endonucleases to isolate a 415 bp fragment. The fragment was isolated by agarose gel electrophoresis, then purified. The replicative form (RF) DNA of phage M13mp18 was digested with XbaI and BamHI restriction endonucleases and the large DNA fragment isolated. The 415 bp fragment was then inserted into the XbaI and BamHI site of the M13mp18 DNA to yield phage M13-W24. Then site-directed mutagenesis was performed as described. Phage M13-W24 was introduced into the *E. coli* CJ236 strain and SS-DNA containing uridine from phage M13-W24 was used as template for site-directed mutagenesis to prepare the mutant M13-WW4. The oligodeoxynucleotide mL17-2,5'-GTGTCAGTTGGCCG-GAGGGTTACTTTGAGC-3', (SEQUENCE ID NO. 19) was used for site-directed mutagenesis. Oligonucleotide mL17-2 contains a phosphokinase recognition site RRVT and also a EaeI recognition site. Oligonucleotide mL17-2 was annealed to uridine-containing SS-DNA of phage M13-WW24, followed by the in vitro synthesis of the complementary strand. Afterwards, the resultant DS-DNA was transformed into *E. coli* DH5αF' strain with a functional uracil N-glycosylase to remove the parental strand. The desired mutant was characterized by EaeI restriction endonuclease digestion and DNA sequencing. Thus we obtained the construct M13-WW4. Then RF-DNA of phage M13-WW4 was digested with XbaI and BamHI restriction endonucleases, and the resultant 410 bp fragment was inserted into vector pCC49 that was digested with the same endonucleases to yield plasmid pWW4. The vector pWW4 expresses the MAb-WW4 with amino acid substitutions E17R and K18R in the MAb-chCC49 light chain.

f. Construction of MAb-WW5

To construct WW5, SS-DNA containing uridine from phage M13-W22 was used as template for site-directed mutagenesis to prepare the mutant M13-WW5. The oligodeoxynucleotide, m221m1rev, 5'-CGGTGGGCATGAGT-GACGTCTGTCACAAGATTTG-3', (SEQUENCE ID NO. 20) was used for site-directed mutagenesis. Oligonucleotide m221 m1 rev contains the phosphokinase recognition site RRHS and also an AatII recognition site. Oligonucleotide m221m1rev was annealed to uridine-containing SS-DNA of M13-WW22, followed by the in vitro synthesis of the complementary strand. Afterwards, the resultant DS-DNA was transformed into *E. coli* DH5αF' strain with a functional uracil N-glycosylase to remove the parental strand. The desired mutant was characterized by AatII restriction endonuclease digestion and DNA sequencing. Thus we obtained the construct M13-WW5. Then RF-DNA of M13-WW5 was digested with SacII restriction endonuclease, and the resultant 410 bp fragment was inserted into the vector pdHL7-CC49 that was digested with the same endonuclease to yield plasmid pWW5. The vector pWW5 expresses the MAb-WW5 with amino acid substitutions K221R, T222R and T224S in the MAb-chCC49 heavy chain.

g. Construction of MAb-WW6

To make the plasmid pLgpCXIIHuWW5ΔCH2 for expression of the heavy chain of the MAb-WW6, the plasmid pLgpCXIIHuCC49ΔCH2 was digested with ApaI and XhoI restriction endonucleases. to isolate a 340 bp fragment. The fragment was isolated by agarose gel electrophoresis, purified and cloned into pBluescript, which was digested with the same restriction endonucleases. The resultant plasmid pBSKS-huHdCH2 was then digested with EcoRI and KpnI restriction endonucleases. The smaller DNA fragment was isolated. The 370 bp fragment was then inserted into the EcoRI and KpnI site of the M13mp19 DNA to yield phage M13-huHdCH2. Then site-directed mutagenesis was performed as described in Section D.3.b. Phage M13-huHdCH2 was introduced into the *E. coli* CJ236 strain and SS-DNA containing uridine from phage M13-huHdCH2 was used as template for site-directed mutagenesis to prepare the mutant M13 -huWW5. The oligodeoxynucleotide, m221m1rev, 5'-CGGTGGGCATGAGTGACGTCTGTCA-CAAGATTTG-3', (SEQUENCE ID NO. 21) was used for site-directed mutagenesis. Oligonucleotide m221m1rev contains the phosphokinase recognition site RRHS and also an AatII recognition site. Oligonucleotide m221m1rev was annealed to uridine-containing SS-DNA of M13-huHdCH2, followed by the in vitro synthesis of the complementary strand. Afterwards, the resultant DS-DNA was transformed into E. coli DH5αF' strain with a functional uracil N-glycosylase to remove the parental strand. The desired mutant was characterized by AatII restriction endonuclease digestion and DNA sequencing. Thus we obtained the construct M13-huWW5. Then RF-DNA of M13-huWW5 was digested with ApaI and XhoI restriction endonucleases, and the resultant 340 bp fragment was inserted into the vector pLgpCXIIHuCC49ΔCH2 that was digested with the same endonuclease to yield plasmid pLgpCXIIHuWW5ΔCH2. The vector pLgpCXIIHuWW5ΔCH2 expresses the heavy chain of MAb-WW6 with amino acid substitutions K221R, T222R and T224S in the MAb-huCC49 heavy chain.

h. Construction of MAb-WW7

Two plasmids pLNCXIIHuCC49HuKV5 and pLgpCXIIHuWW5V8ΔCH2 were made for the expression of the light chain and the heavy chain of MAb-WW7, respectively.

To make pLNCXIIHuCC49HuKV5, the plasmid pBScHuCC49V5 was first digested with HindIII and, ApaI restriction endonucleases, then blunt-ended by Klenow fragment of DNA polymerase to yield a 1.1 kb fragment. Another plasmid pLNCXIIHuCC49HuK was digested with HindIII restriction endonuclease, blunt-ended, and the resultant 6.5 kb large fragment was isolated. Then the 1.1 kb fragment was ligated to this 6.5 kb fragment to yield plamid pLNCXIIHuCC49HuKV5. The plasmid pLNCXIIHuCC49HuKV5 was characterized by NheI restriction endonuclease digestion and DNA sequencing.

To make pLgpCXIIHuWW5V8ΔCH2, the plasmid pBScHuCC49V8ΔCH2 was first digested with HindIII and ClaI restriction endonucleases, and the resultant 1.1 kb fragment was isolated and purified. The plasmid pLgpCXIIHuWW5ΔCH2 was digested with same restriction endonucleases. The 6.5 kb fragment was isolated from the two fragments obtained. The 1.1 kb fragment was then ligated to this 6.5 kb fragment to yield plasmid pLgpCXIIHuCC49V8ΔCH2. Afterwards, the pLgpCXIIHuCC49V8ΔCH2 was digested with ApaI and XhoI restriction endonucleases. The large 7269 bp fragment was isolated. Then the pLgpCXIIHuWW5ΔCH2 was digested with same restriction endonucleases to isolate a 340 bp fragment. This 340 bp fragment was finally ligated to the 7269 bp fragment to yield the plamid pLgpCXIIHuWW5V8ΔCH2.

i. Construction of MAb-WW8

To construct the expression vector for MAb-WW8, an intermediate vector pWW5t-BB was made so that one of two XhoI restriction sites in pWW5 could be removed. To construct pWW5t-BB, the pWW5 was digested with BstEI and BglII restriction endonucleases. The resultant 7800 bp fragment was isolated, blunt-ended, and then self-ligated to generate intermediate vector pWW5t-BB. Then a 420 bp fragment was amplified from the plasmid pLgpCXIIHuCC49ΔCH2 by PCR with the 5' primer, 5'-kashH-7, CCCCTCGAGCCACCATGGAGTGGTCCTGGGTC, (SEQUENCE ID NO. 22) and 3' primer, 3'-kashH-420, CCCAAGCTTTTTGGCGCTGGAGACGGTGACCAG, (SEQUENCE ID NO. 23) respectively. This PCR fragment was then digested with XhoI and HindIII restriction endonucleases, isolated by agarose gel electrophoresis, purified, and subcloned into pWW5t-BB, which was digested with the same restriction endonucleases to obtain pWW5t-huVH-BB. Then pWW5t-huVH-BB was digested with BamHI and XbaI restriction endonucleases to isolate a 7400 bp fragment. Then a 400 bp fragment was amplified from the plasmid pLNCXIIHuCC49HuK by PCR with the 5' primer, 5'-kashL-11, CCTCTAGACCACCATGGATAGCCAGGCCCAG, (SEQUENCE ID NO. 24) and 3' primer, 3'-kashL-425, GCCGCGGCCCGTGGATCCTTCAGTTCCAGCTT, (SEQUENCE ID NO. 25) respectively. This PCR fragment was then digested with BamHI and XbaI restriction endonucleases, purified, and ligated to the 7400 bp fragment to yield pWW8-BB. Finally, pWW8-BB was digested with HindIII and XbaI restriction endonucleases, and yielded two fragments. The smaller fragment, 3000 bp, was isolated and purified. Then the plasmid pWW5 was digested with the same restriction endonucleases. The large fragment, which was 6400 bp, was also isolated, purified, and ligated into the purified 3000 bp fragment. The resultant construct pWW8 was characterized by EaeI restriction endonuclease digestion and DNA sequencing. The vector pWW8 expresses the humanized MAb-WW5 with amino acid substitutions K221R, T222R and T224S in the MAb-chCC49 heavy chain.

4. Expression of Monoclonal Antibodies a. Expression of MAb-chCC49-6P, MAb-WW1, MAb-WW2, MAb-WW3, MAb-WW4 and MAb-WW5

Electroporation was used to introduce the plasmids pMAb-chCC49-6P, pMAb-WW1, -WW2, -WW3, -WW4 and -WW5 into mouse myeloma NS0 cells. First, $2 \times 10^7$ cells in 450 µl of ice cold PBS was mixed with 12 µg of purified plasmid in an electroporation cuvette. The cells were incubated on ice for 10 min. The electroporator was adjusted to the following settings: 0.24 KV and 950 µF. After electroporation of cells for 30 msec (time constant), the cells were allowed to recover on ice for 10 min, then were transferred from the cuvette into 30 ml of medium containing DMEM, 10% fetal bovine serum and 1% glutamine, and then were dispensed into 96-well plates with 100 µl in each well. After 48 hours, selection medium containing DMEM, 10% fetal bovine serum, 1% glutamine, and 0.15 µM of methotrexate replaced the medium. Subsequently, selection medium was used every 3–4 days to replace the medium until stable transformants were obtained. The expression of the mutant protein in the cell culture supernatants was determined by ELISA. Clones with the highest expression of modified MAbs were chosen for expansion. First, cells from a 96-well plate were placed in a 24 well plate and then gradually expanded to 150 cm² flasks. In 150 cm² flasks, $5 \times 10^6$ cells were grown in 50 ml medium until the medium was yellow and most of the cells were dead, then supernatant was collected.

b. Expression of MAb-WW6

To express MAb-WW6, electroporation was used to introduce the plasmids pLNCXIIHuCC49HuK and pLgpCXIIHuWW5ΔCH2 into mouse myeloma NS0 cells. The procedure was the same as described in Section D.4.a except that the medium containing DMEM, 10% fetal bovine serum, 1% glutamine, 700 µg/ml of G418, 1 µg/ml of mycophenolic acid, 250 µg/ml of xanthine, and 15 µg/ml of hypoxanthine was used as selection medium.

After cells were expanded to 150 cm² flasks, $5 \times 10^6$ cells were grown in 50 ml protein-free hybridoma medium PFHM-II (Gibco BRL). The supernatant was then collected after most of the cells were dead.

c. Expression of MAb-WW7

To express MAb-WW7, electroporation was used to introduce the plasmids pLNCXIIHuCC49HuKV5 and pLgpCXIIHuWW5V8ΔCH2 into mouse myeloma NS0 cells. The procedure was the same as described in Section D.4.a except that the medium containing DMEM, 10% fetal bovine serum, 1% glutamine, 700 µg/ml of G418, 1 µg/ml of mycophenolic acid, 250 µg/ml of xanthine, and 15 µg/ml of hypoxanthine was used as selection medium.

After cells were expanded to 150 cm² flasks, 5×10⁶ cells were grown in 50 ml protein-free hybridoma medium PFHM-II (Gibco BRL). The supernatant was then collected after most of the cells were dead.

5. Purification of Monoclonal Antibodies a. Purification of MAb-chCC49-6P, MAb-WW1, MAb-WW2, MAb-WW3, MAb-WW4 and MAb-WW5

Before purification of MAb-chCC49-6P, MAb-WW1, -WW2, -WW3, -WW4 and -WW5, supernatants from several 150 cm² flasks were pooled. Then the cell culture supernatants containing the modified MAbs were purified as described with some minor modifications. Briefly, a 1 ml protein A column was equilibrated with three column volumes of buffer A (3 M NaCl, 1 M glycine, pH 8.8). Solid NaCl was added to the cell culture supernatants to a concentration of 3 M. Then the pH of the cell supernatants was adjusted to pH 8.0 with 1 M glycine (pH 8.8). Supernatants (about 300 ml) were centrifuged at 7268×g for 10 min. Then after passage through 0.2 μm filter units, the supernatants were loaded onto the protein A column at a flow rate of 1 ml/min. The columns were washed with buffer A for five column volumes. Afterwards, the columns were eluted with two column volumes of buffer B (0.2 M glycine•HCl, pH 2.5). Eluates were neutralized with 1 ml of buffer C (10 mM boric acid, 2.5 mM borax and 7.5 mM of NaCl, pH 8.5) with the neutralized solution having a pH of 7.0. The purified MAbs were dialyzed against 1000 volumes of PBS overnight at 4° C. The dialyzed MAbs were then concentrated with a Centricon concentrator. The protein concentrations of purified MAbs were determined by ELISA, and the purities of IgG were checked by SDS polyacrylamide gel electrophoresis. The purified MAbs were then aliquoted into 0.5 ml tubes and stored frozen at −20° C. or below until use.

b. Purification of MAb-WW6 and MAb-WW7

Since CH2 domain deleted MAbs could not bind to Protein A, Protein G-Sepharose (Pharmacia) was used to purify MAb-WW6 and MAb-WW7. Before purification of MAb-WW6 and MAb-WW7, supernatants from several 150 cm² flasks were pooled. Then the cell culture supernatants containing the modified MAbs were purified. Briefly, a 1 ml protein G column was equilibrated with three column volumes of Buffer A (3 M NaCl, 1 M glycine, pH 8.8). Solid NaCl was added to the cell culture supernatants to a concentration of 3 M. Then the pH of the cell supernatants was adjusted to pH 8.0 with 1 M glycine (pH 8.8). Supernatants (about 300 ml) were centrifuged at 7268×g for 10 min. Then after passage through 0.2 μm filter units, the supernatants were loaded onto the protein G column at a flow rate of 1 ml/min. The columns were washed with Buffer A for five column volumes. Afterwards, the columns were eluted with two column volumes of 0.1 M glycine•NaOH, pH 10). Eluates were neutralized with 80 μl of 2 M NaH₂PO₄ to adjust the pH to 7.0. The purified MAbs were dialyzed against 1000 volumes of PBS overnight at 4° C. The dialyzed MAbs were then concentrated with a Centricon concentrator. The protein concentrations of purified MAbs were determined by ELISA, and the purities of IgG were checked by SDS polyacrylamide gel electrophoresis. The purified MAbs were then aliquoted into 0.5 ml tubes and stored frozen at −20° C. or below until use.

6. Phosphorylation of MAb-chCC49-6P, MAb-WW1, MAb-WW2, MAb-WW3, MAb-WW4, MAb-WW5, MAb-WW6 and MAb-WW7

Each mutant MAb was labeled with [γ-³²P]ATP and the cAMP-dependent protein kinase as described previously. Approximately 10 μg of MAb was incubated at 30° C. for 60 min with 0.5 mCi of [γ-³²P]ATP and 15 units of the catalytic subunit of cAMP-dependent protein kinase from bovine heart muscle (6 mg/ml DTT) in 25 μl of 20 mM Tris•HCl, pH 7.4, 100 mM NaCl, and 12 mM MgCl₂, then cooled on ice to stop the reaction. After addition of 300 μl containing 5 mg/ml bovine serum albumin in 10 mM sodium pyrophosphate, pH 6.7, at 4° C., the 0.325 ml reaction mixture was dialyzed against 10 mM sodium pyrophosphate, pH 6.7, overnight at 4° C. Dialysis buffer was changed twice. Incorporation of radioactivity into the monoclonal antibodies was measured with a liquid scintillation spectrometer after precipitation of the protein with trichloroacetic acid (Pestka, 1972). To remove any labile ³²P, the final product in 0.325 ml was adjusted to pH 7.4 with 1 M Tris base, then incubated at 37° C. overnight.

7. Determination of Immunoreactivities of [32P]MAbs

Direct binding assays were carried out as follows. The 96-well plates were coated with 100 μl of TAG-72 positive bovine submaxillary mucin (BSM) or TAG-negative porcine submaxillary mucin (PSM) at a concentration of 10 μg/ml in PBS overnight at 4° C. Then the plates were blocked with 5% BSA in PBS. The [³²P]MAbs were serially diluted in 1% BSA in PBS, starting with 2×10⁵ cpm in 100 μl. The plates were incubated overnight at 4° C., then washed four times with 1% BSA in PBS. Finally, 150 μl of 0.2 N NaOH was added into each well, then collected and placed into a scintillation vial. The process was repeated with another 150 μl of 0.2 N NaOH that was added to the same scintillation vial and counted.

Direct binding assays were also carried out by passing [³²P]MAbs over beads coated either with BSM or PSM. The BSM was immobilized onto beads (Reacti-Gel HW65F; Pierce, Rockford, Ill.) as described (Johnson et al., 1986; Kashmiri et al., 1995) at a ratio of 2 mg BSM to 1 ml of wet-packed beads. The BSM beads (50 μl wet-packed volume) were placed in a 1.5 ml Eppendorf tube in duplicate. Then 2×10⁵ cpm of [³²P]MAbs in 1 ml of 1% bovine serum albumin (BSA) in PBS was added to each tube in duplicate. After incubation for 2 hours at room temperature with end-over-end mixing, the BSM beads were then pelleted at 1000×g for 5 minutes. The supernatant was removed by aspiration and discarded. The beads were then washed three times with 1 ml of 1% BSA in PBS by centrifugation followed by aspiration of the supernatant as described. The radioactivity remaining on the beads in each tube was measured and the total percent of [³²P]MAbs bound to the BSM beads was calculated as (counts bound)/(total counts loaded)×100 where total counts represents 2×10⁵ cpm and counts bound represents the counts on the beads.

8. Determination of Stability of ³²P-labeled MAbs in Sera

The stability of ³²P-labeled MAbs were determined as described previously with minor modification. Briefly, each reaction contained 0.5 ml of human serum, mouse serum, fetal bovine serum or a solution of bovine serum albumin (5 mg/ml in PBS), 125 μl of 1 M Tris•HCl, pH 7.4, and 3 μl of the [³²P]MAb (2.4×10⁶ cpm) for a total volume of 628 μl and was incubated at 37° C. Portions of 20 μl were taken in duplicate over a 24-hour, 5-day, or 21-day period to determine the stability of [³²P]phosphate attached to the MAb by TCA precipitation.

II. Results

Construction of Phosphorylatable Chimeric Monoclonal Antibodies of MAb-chCC49

1. Model of MAb-chCC49

Figure 4:
FIG. 4 illustrates a model of the MAb-chCC49 antibody. This figure shows the complete 3D model of MAb-chCC49. The light chains are shown in yellow, while the heavy chain on the left is in cyan, and the one on the right in royal-blue. The red-orange regions shown in space-filling models represent the sites where protein kinase recognition sites were considered: nine sites on the heavy chains and three on the light chains.
Figure 5:
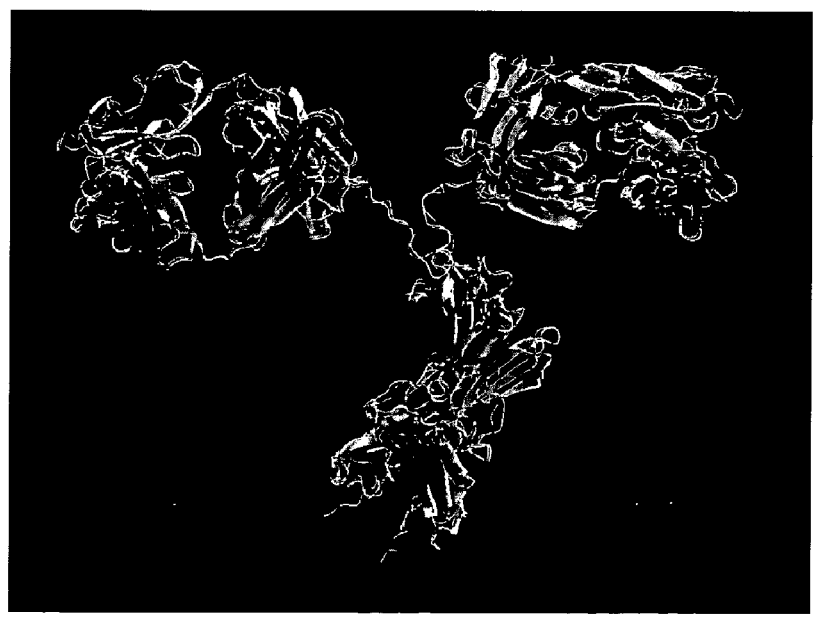
FIG. 5 depicts a comparison of the structures of the MAb-chCC49 and MAb231 antibodies. MAb-chCC49 is shown in magenta, and MAb231 is shown in green.

The 3-D model of MAb-chCC49 was built by using the crystal structure of MAb231 as template as described herein (see also FIG. 4). The modeled MAb-chCC49 showed overall structural similarity to the template molecule MAb231. Again, the asymmetrical T shape and the extended hinge region were seen in the MAb-chCC49 model, which was consistent with its overall sequence similarities to MAb231. However, when MAb-chCC49 was superimposed on MAb231 (FIG. 5), the local structural differences were noticed, especially in the CDR regions of the two MAbs. This is consistent with the differences in the primary amino acid sequences of two molecules in this region.

2. Overview of the Models of the Phosphorylatable Chimeric Monoclonal Antibodies of MAb-chCC49 and Phosphorylated Modified MAbs The models of the phosphorylatable chimeric monoclonal antibodies of MAb-chCC49 and phosphorylated modified MAbs are shown in FIGS. 6–9. The modeled modified MAbs all showed, the asymmetrical T shape and extended hinge region as noted above for MAb231 (FIG. 5). A close look at the site where we introduced the cAMP-dependent phosphorylation site revealed that almost all the amino acid residues which are essential to the phosphorylation were exposed on the surface, suggesting that this site would be accessible for the binding of PKA and thereby facilitating the phosphorylation. Not surprisingly, when MAb-chCC49 and modified MAbs were superimposed, they exhibited identical structures in most of the regions except for the area where the phosphorylation site was introduced in the mutant MAbs (FIG. 10, where only superimposion of models of MAb-WW5 and MAb-chCC49 are shown.). No significant structural differences in the backbone geometry were noticeable in the CDR regions of MAb-chCC49 or modified MAbs, which suggested that after introduction of a phosphorylation site in MAb-chCC49, the binding ability of the modified MAbs would not be changed significantly.

The systematic search results for each kinase recognition site are summarized in Table 1. It can be seen that on some constructs (MAb-chCC49K1, MAb-CC49CKI, MAb-CC49CKII, MAb-CC49Tyr, MAb-chCC49-6P, MAb-WW5, -WW6, -WW7 and -WW8), the attached phosphates have more allowed conformations than those on other constructs (MAb-WW1, -WW2, -WW3 and -WW4).

a. Models of MAb-chCC49K1 and Phosphorylated MAb-chCC49K1

Figure 6A:
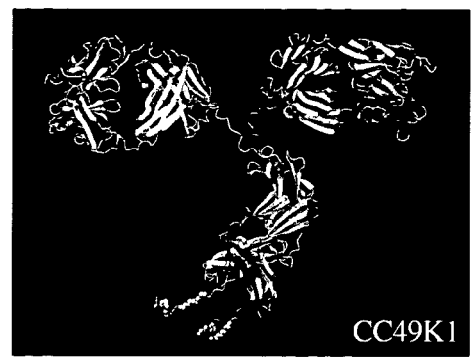
FIG. 6 illustrates models of mutant MAbs. The light chains of the MAbs are shown in yellow, while the heavy chain on the left is in cyan, and the one on the right in royal-blue. The red-orange regions shown in the space-filling models represent the region where the protein kinase recognition sites are introduced. A: the model of Mab-chCC49K1; B: the model of MAb-CC49CKI; C: the model of MAB-CC49CKII; D: the model of MAb-CC49Tyr.
Figure 8A:
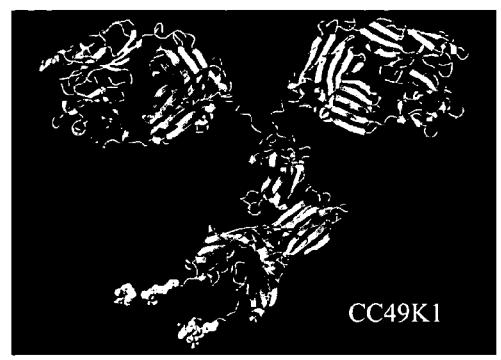
FIG. 8 illustrates models of mutant [$^{32}$P]MAbs. The light chains of the MAbs are shown in yellow, while the heavy chains are in royal-blue. The white regions shown in the space-filling models represent the regions where the protein kinase recognition sites are introduced. The green regions that represent the phosphates attached to the serine or tyrosine residues are barely visible. The oxygens attached to the phosphates are in red. A: the model of [$^{32}$P]MAb-chCC49K1; B: the model of [$^{32}$P]MAb-CC49CKI; C: the model of [$^{32}$P]MAb-CC49CKII; D: the model of [$_{32}$P]MAb-Tyr.

The models of MAb-chCC49K1 and phosphorylated MAb-chCC49K1 are shown in FIG. 6A and FIG. 8A. It can be seen that the phosphorylation site in MAb-chCC49K1 is more extended than those in MAb-WW1, -WW2, -WW3, -WW4, and WW5 and is highly accessible to the enzyme. Phosphate groups were attached to serine residues (Ser449 and Ser455) on the PKA sites of MAb-chCC49K1 and the systematic conformational searches (Table 1) were done as described herein to determine the conformation of the phosphate groups. As seen from Table 1, the searches corresponding to Ser455 and Ser449 of heavy chains 1 and 2, respectively, yielded 43 and 54 conformations, more than for the other mutant MAbs in Table 1, suggesting the easy accessibility of the PKA recognition site in these sites of the MAb. However, the searches corresponding to Ser449 and Ser455 of heavy chains 1 and 2, respectively, only yielded 18 and 15 conformations. But since the PKA recognition sites on MAb-chCC49K1 are on the flexible C-terminus of the MAb, additional searches along the main chain of the MAb was allowed in performing searches to see if more conformations were allowed for the attached phosphates. Therefore, we searched along Cϕ-Cψ of Ser449 as well as Cα-Cβ and Cβ-Oγ of Ser449, chain 1. The results are shown in Table 1. This search yielded 655 allowed conformations for the attached phosphates, reflecting the flexible nature of the site. Similar results were obtained for the search corresponding to Ser455 (chain 2). We searched along Cϕ-Cψ of Ala454, Ser455, Met456 as well as Cα-Cβ and Cβ-Oγ of Ser455 (chain 2), and it was found that 2298 conformations were allowed for the attached phosphates.

Figure 11:
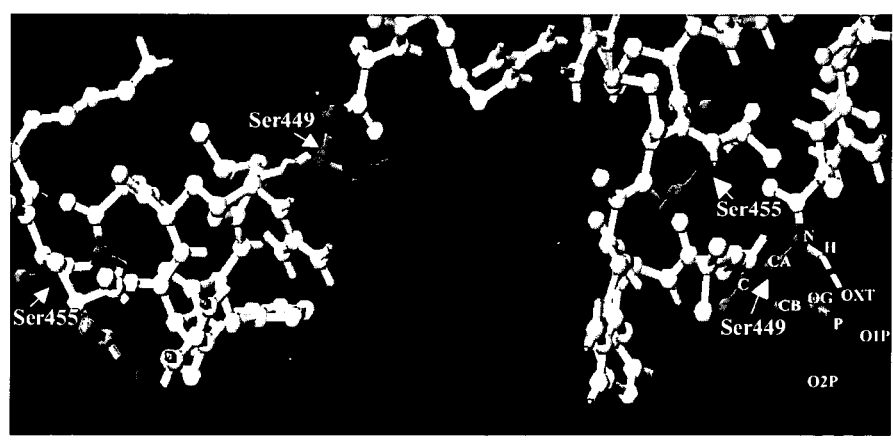
FIG. 11 shows the hydrogen bond of the serine phosphate group with the adjacent amino acid in MAb-chCC49K1. The serine carbons are: C, carbonyl carbon; CA, alpha carbon; CB, beta carbon to which the phosphate (P) is attached through the serine oxygen (OG). Other symbols are: OXT, first oxygen of the phosphate in hydrogen bond on the right; O1P, second oxygen on phosphate; O2P, third oxygen on phosphate; H, hydrogen in a hydrogen bond from amino acid nitrogen (N) to phosphate oxygen OXT. All four serine residues shown in this figure are modified with phosphate groups. Only one of the phosphates forms a hydrogen bond.

One interesting phenomenon we noticed when we did first-round systematic searches was that on some sites, the phosphates had potential to form hydrogen bonds with the surrounding amino acids in some of the allowed conformations (Table 1). However on the other sites, the phosphates had no potential at all to form hydrogen bonds in any of the allowed conformations. As to MAb-chCC49K1, one of the four phosphates attached to MAb-chCC49K1 could be stabilized through a hydrogen bond (FIG. 11). The hydrogen bond was formed with the NH group of Ser449 of the same heavy chain. Overall these data clearly demonstrate that the two heavy chains are not symmetrical and exhibit significant differences in their structures.

b. Models of MAb-chCC49CKI and Phosphorylated MAb-chCC49CKI

Figure 6B:
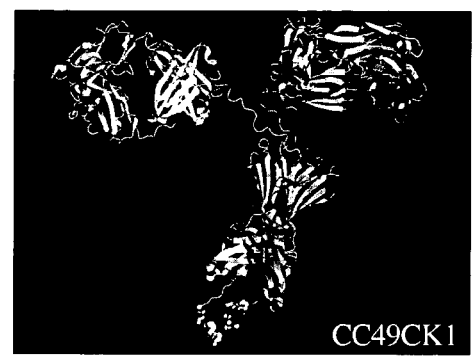
Figure 8B:
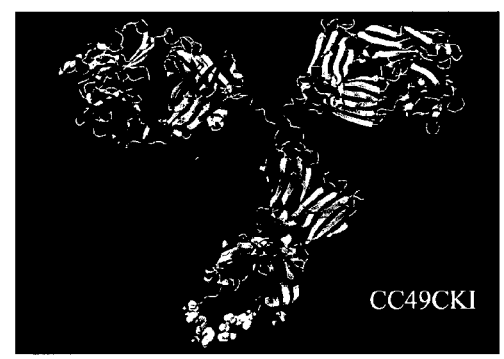

The models of MAb-chCC49CKI and phosphorylated MAb-chCC49CKI are shown in FIG. 6B and FIG. 8B, respectively. Phosphate groups were attached to serine residues (Ser450 and Ser457) on the PKA sites of MAb-chCC49CKI and the systematic conformational searches (Table 1) were done as described herein to determine the conformation of the phosphate groups. As seen in Table 1, the search corresponding to Ser450 of heavy chain 1 yielded 40 conformations, more than for some other mutant MAbs in Table 1. However, the other three searches yielded 28, 6, and 30 conformations. But since the PKA recognition sites on MAb-chCC49CKI are also on the flexible C-terminus of the MAb, we did additional searches along the main chain of the MAb to see if more conformations were allowed for the attached phosphates. The results are shown in Table 1. For the search corresponding to Ser457 (chain 1), we searched along Cϕ-Cψ of Ser457 as well as Cα-Cβ and Cβ-Oγ of Ser457 (chain 1). This search yielded 618 allowed conformations. Similar results were obtained for the searches corresponding to Ser450 and Ser457 (chain 2) evaluated as shown in Table 1.

Before we did additional conformational searches, we also performed searches to see if the attached phosphates have potential to form hydrogen bonds with the surrounding amino acids. Three of the four serine phosphates on MAb-chCC49CKI showed this potential (Table 1). Here again the asymmetry of the antibody structure is evident.

c. Models of MAb-chCC49CKII and Phosphorylated MAb-chCC49CKII

Figure 6C:
Figure 8C:
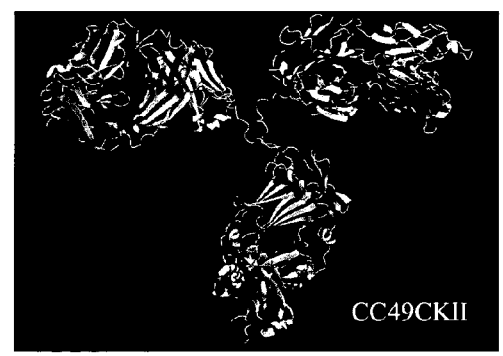

The models of MAb-chCC49CKII and phosphorylated MAb-chCC49CKII are shown in FIG. 6C and FIG. 8C, respectively. Phosphate groups were attached to serine residues (Ser436) on the PKA sites of MAb-chCC49CKII and the systematic conformational searches (Table 1) were done as described herein to determine the conformations of the phosphate groups. As seen from Table 1, two searches yielded 56 and 48 conformations, respectively.

We also performed specific searches to see if the attached phosphates have potential to form hydrogen bonds with the surrounding amino acids. One of the two serine phosphates on MAb-chCC49CKII showed the potential to form a hydrogen bond (Table 1).

d. Models of MAb-chCC49Tyr and Phosphorylated MAb-chCC49Tyr

Figure 6D:
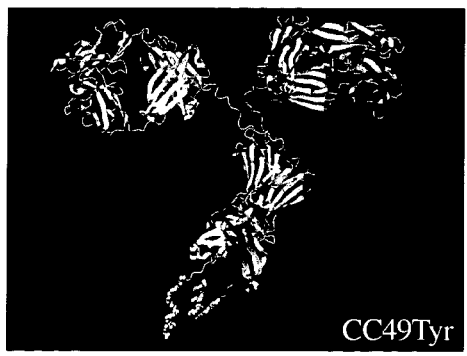
Figure 8D:

The models of MAb-chCC49Tyr and phosphorylated MAb-chCC49Tyr are shown in FIG. 6D and FIG. 8D, respectively. After phosphate groups were attached to tyrosine residues (Tyr455) on the PKA sites of MAb-chCC49Tyr, the systematic conformational searches were performed as described herein to determine the conformations of the phosphate groups. As seen from Table 1, two searches yielded 60 and 213 conformations, respectively.

We performed specific searches to see if the attached phosphates have potential to form hydrogen bonds with the surrounding amino acids. One of the two tyrosine phosphates on MAb-chCC49Tyr showed the potential to form a hydrogen bond (Table 1).

e. Models of MAb-chCC49-6P and Phosphorylated MAb-chCC49-6P

Figure 7A:
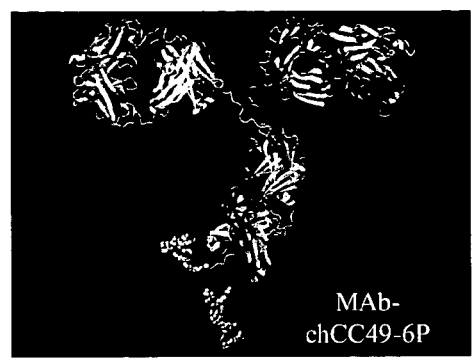
FIG. 7 also illustrates models of mutant MAbs. The light chains of the MAbs are shown in yellow, while the heavy chain on the left is in cyan, and the one on the right in royal-blue. The red-orange regions shown in the space-filling models represent the regions where the protein kinase recognition sites were introduced. A: the model of MAb-chCC49-6P; B: the model of MAb-WW1; C: the model of MAb-WW2; D: the model of MAb-WW3; E: the model of MAb-WW4; F: the model of MAb-WW5; G: the model of MAb-WW6; H: the model of MAb-WW7; I: the model of MAb-WW8.
Figure 9A:
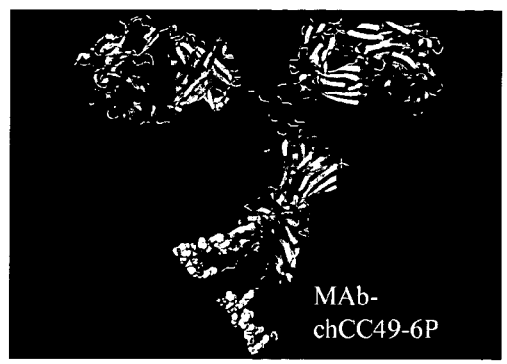
FIG. 9 depicts models of mutant [$^{32}$P]MAbs. The light chains of the MAbs are shown in yellow, while the heavy chains are in royal-blue. The white regions shown in the space-filling models represent the regions where the protein kinase recognition sites were introduced. The green regions that represent the phosphates attached to the serine or threonine residues are barely visible. The oxygens attached to the phosphates are in red. A: the model of [$^{32}$P]MAb-chCC49-6P; B: the model of [$^{32}$P]Mb-WW1; C: the model of [$^{32}$P]MAb-WW2; D: the model of [$^{32}$P]MAb-WW3; E: the model of [$^{32}$P]MAb-WW4; F: the model of [$^{32}$P]MAb-WW5; G: the model of [$^{32}$P]MAb-WW6; H: the model of [$^{32}$P]MAb-WW7; I: the model of [$^{32}$P]MAb-WW8.
Figure 10:
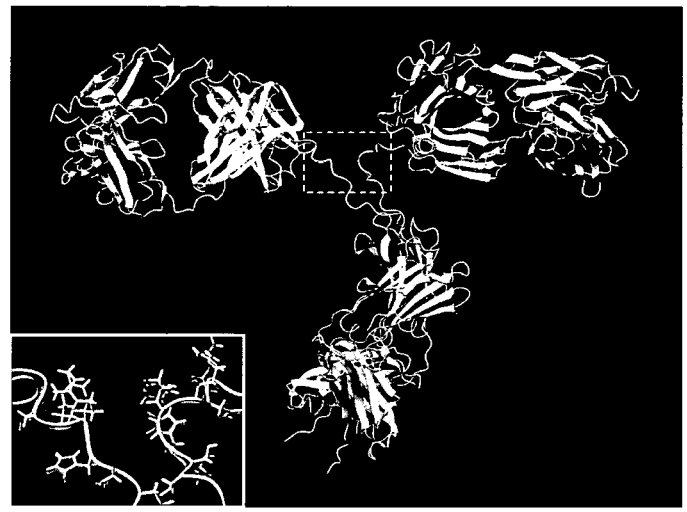
FIG. 10 is a comparison of the structures of MAb-chCC49 and MAb-WW5. MAb-WW5 is shown in cyan, while MAb-chCC49 is in magenta. The magenta is not visible because the two structures are virtually identical. The inset (lower left) shows a magnification of the hinge region with side chains between the CH1 and CH2 domains where the protein kinase recognition site was introduced (boxed area).

The models of MAb-chCC49-6P and phosphorylated MAb-chCC49-6P are shown in FIG. 7A and FIG. 9A, respectively. The systematic conformational search results are shown in Table 1. It could be seen that the searches corresponding to Ser470 (chain 1), Ser485 (chain 1) and Ser449 (chain 2) yielded about 50 conformations, much more than other searches on the same MAbs. But since the PKA recognition sites on MAb-chCC49-6P are also on the flexible C-terminus of the MAb, we did additional searches along the main chain of the MAb to see if more conformations were allowed for the other attached phosphates. As seen from Table 1, all of the additional searches for MAb-chCC49-6P yielded much more conformations than the first-round searches.

We performed specific searches to see if the attached phosphates have potential to form hydrogen bonds with the surrounding amino acids. Seven of the twelve serine phosphates on MAb-chCC49-6P showed the potential to form hydrogen bonds (Table 1).

f. Models of MAb-WW1 and Phosphorylated MAb-WW1

Figure 7B:
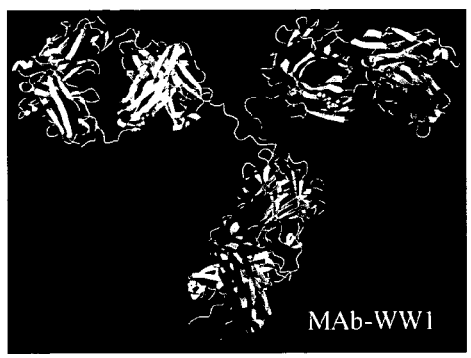
Figure 9B:

The models of MAb-WW1 and phosphorylated MAb-WW1 are shown in FIG. 7B and FIG. 9B. After phosphate groups were attached to serine residues (Ser21) on the PKA sites of MAb-WW1, the systematic conformational searches were done as described herein to determine the conformations of the phosphate groups. Search results revealed that for MAb-WW1, phosphate groups attached to Ser21 of heavy chain 1 had thirteen conformations, but only one allowed conformation on heavy chain 2 (Table 1). However since the PKA recognition sites on MAb-WW1 are in the CH1 region of the MAb, rather than in any of the flexible termini, no additional searches along the main chain of the MAb were allowed for the attached phosphates.

We performed specific searches to see if the attached phosphates have potential to form hydrogen bonds with the surrounding amino acids. None of the serine phosphates on MAb-WW1 showed the potential to form a hydrogen bond (Table 1).

g. Models of MAb-WW2 and Phosphorylated MAb-WW2

Figure 7C:
Figure 9C:

The models of MAb-WW2 and phosphorylated MAb-WW2 are shown in FIG. 7C and FIG. 9C, respectively. After phosphate groups were attached to threonine residues (Thr224) on the PKA sites of MAb-WW2, the systematic conformational searches were done as described herein. Similar results were obtained after two systematic searches. Twenty one and thirteen conformations were revealed after two searches. However, similar to MAb-WW1, since the PKA recognition sites on MAb-WW2 are in the hinge region of the MAb, rather than in any of the flexible termini, no additional searches along the main chain of the MAb were allowed for the attached phosphates.

Figure 12A:
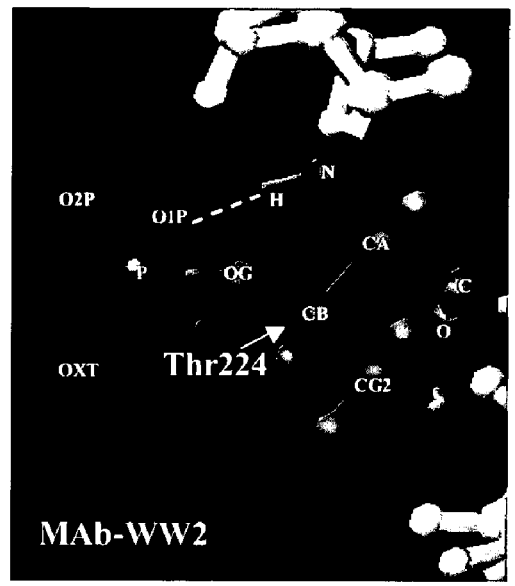
FIG. 12 depicts the hydrogen bond of the phosphate group with the adjacent amino acid. A. Hydrogen bond of the Thr-phosphate group with the adjacent amino acid in MAb-WW2. B. Hydrogen bond of the Ser-phosphate group with the adjacent amino acid in MAb-WW3. The Ser/Thr carbons are: C, carboxyl carbon; CA, alpha carbon; CB, beta carbon to which the phosphate (P) is attached through the serine oxygen (OG). Other symbols are: OXT, one oxygen of the phosphate; O1P, second oxygen of phosphate; O2P, third oxygen on phosphate. The figure is a ball and stick model as described herein.

We performed specific searches to see if the attached phosphates have potential to form hydrogen bonds with the surrounding amino acids. Several conformations from both searches showed that the phosphate groups had the potential to form a hydrogen bond with the NH group of Thr224 (Table 1, FIG. 12A).

h. Models of MAb-WW3 and Phosphorylated MAb-WW3

Figure 7D:
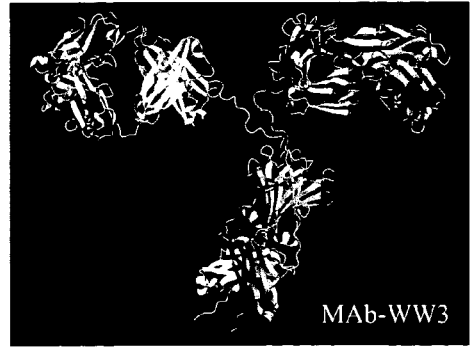
Figure 9D:
Figure 12B:
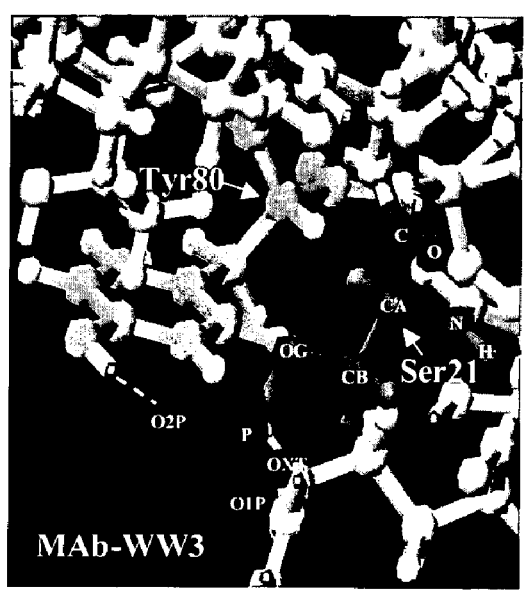

The models of MAb-WW3 and phosphorylated MAb-WW3 are shown in FIG. 7D and FIG. 9D, respectively. After phosphate groups were attached to serine residues (Ser21) on the PKA sites of MAb-WW3, the systematic conformational searches were done as described herein. For MAb-WW3, after the search corresponding to Ser21(chain 1) was performed, nine conformations were obtained. Potential for hydrogen bond formation was observed (Table 1). Among these conformations, we chose the one with the lowest energy (4127 kcal/mol), where phosphate group can form a hydrogen bond with hydroxyl group on the side chain of Tyr80 (FIG. 12B) to do the conformational search corresponding to Ser21 (chain 2). Results were similar to those obtained on the previous search. Similar to MAb-WW1, since the PKA recognition sites on MAb-WW3 are in the variable region of the heavy chain of the MAb, rather than in any of the flexible termini, no additional searches along the main chain of the MAb were allowed for the attached phosphates.

i. Models of MAb-WW4 and Phosphorylated MAb-WW4

Figure 7E:
Figure 9E:

The models of MAb-WW4 and phosphorylated MAb-WW4 are shown in FIG. 7E and FIG. 9E, respectively. After phosphate groups were attached to threonine residues (Thr17) on the PKA sites of MAb-WW4, the systematic conformational searches were done as described herein. For MAb-WW4, the results obtained from two systematic searches were very similar. Only two conformations were obtained from each search. Similar to MAb-WW1, since the PKA recognition sites on MAb-WW4 are in the variable region of the light chain of the MAb, rather than in any of the flexible termini, no additional searches along the main chain of the MAb were allowed for the attached phosphates.

No hydrogen bond formation was observed between the phosphates on MAb-WW4 and any surrounding amino acid residues after two systematic searches (Table 1).

j. Models of MAb-WW5 and Phosphorylated MAb-WW5

Figure 7F:
Figure 9F:
Figure 13A:
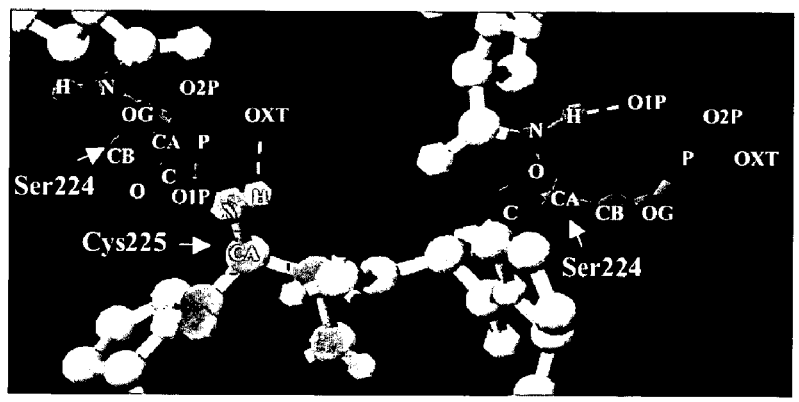
FIG. 13 shows the stabilization of the phosphate moiety on serine 224 in MAb-WW5. A. The side chain of Ser224 stabilized the phosphate moiety through hydrogen bonding either between the phosphate and main chain nitrogen on cysteine 225 (on the left), or between the phosphate and main chain nitrogen on serine 224 (on the right). B. The side chain of Ser224 stabilized the phosphate moiety through hydrogen bonding between the phosphate and main chain nitrogen. The serine carbons are: C, main chain carbonyl carbon; CA, alpha carbon; CB, beta carbon to which the phosphate (P) is attached through the serine oxygen (OG). Other symbols are: OXT, first oxygen of the phosphate; O1P, second oxygen of phosphate that forms a hydrogen bond; O2P, third oxygen on phosphate; H, hydrogen in hydrogen bonds from amino acid nitrogens (N) to phosphate oxygens.
Figure 13B:
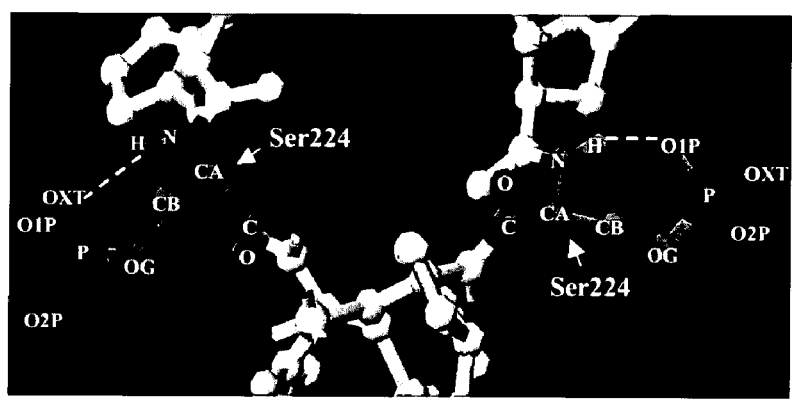

The models of MAb-WW5 and phosphorylated MAb-WW5 are shown in FIG. 7F and FIG. 9F. After phosphate groups were attached to serine residues (Ser224) on the PKA sites of MAb-WW5, the systematic conformational searches were performed as described herein. For MAb-WW5, similar results were obtained after two systematic searches. Sixty-one conformations were revealed after the search corresponding to Ser224 (heavy chain 1). The search corresponding to Ser224 (heavy chain 2) yielded similar results as the previous one with fifty-seven conformations possible. Analysis of the conformations showed that the phosphate group of the Ser224 of chain 1 had the potential to form a hydrogen bond with either NH group on Cys225 or Ser224 (Table 1, FIG. 13A). In contrast, the phosphate group of the Ser224 of chain 2 could only form a hydrogen bond with Ser224 (Table 1, FIG. 13B).

k. Models of MAb-WW6 and Phosphorylated MAb-WW6

Figure 7G:
Figure 9G:
Figure 14A:
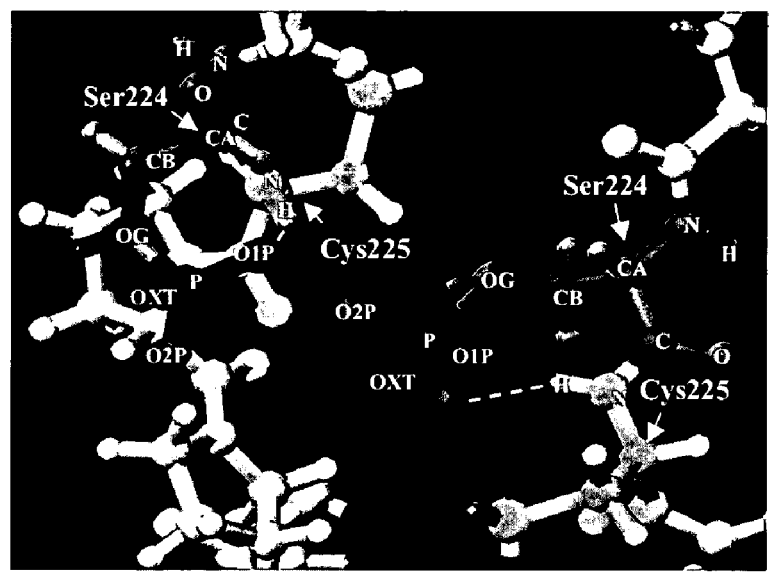
FIG. 14 shows the stabilization of the phosphate moiety on serine 224 in MAb-WW6. A. The side chain of Ser224 stabilized the phosphate moiety through hydrogen bonding between the phosphate and main chain nitrogen on cysteine 225. B. The side chain of Ser224 stabilized the phosphate moiety through hydrogen bonding between the phosphate and main chain nitrogen on cysteine 225 on the left, and hydrogen bonding between the phosphate and main chain nitrogen on cysteine 225 on the right. Serine 224 are shown in magenta, and cysteine 225 in green. The serine carbons are: C, main chain carbonyl carbon; CA, alpha carbon; CB, beta carbon to which the phosphate (P) is attached through the serine oxygen (OG). Other symbols are: OXT, first oxygen of the phosphate; O1P, second oxygen of phosphate; O2P, third oxygen on phosphate; H, hydrogen in hydrogen bonds from amino acid nitrogens (N) to phosphate oxygens.
Figure 14B:
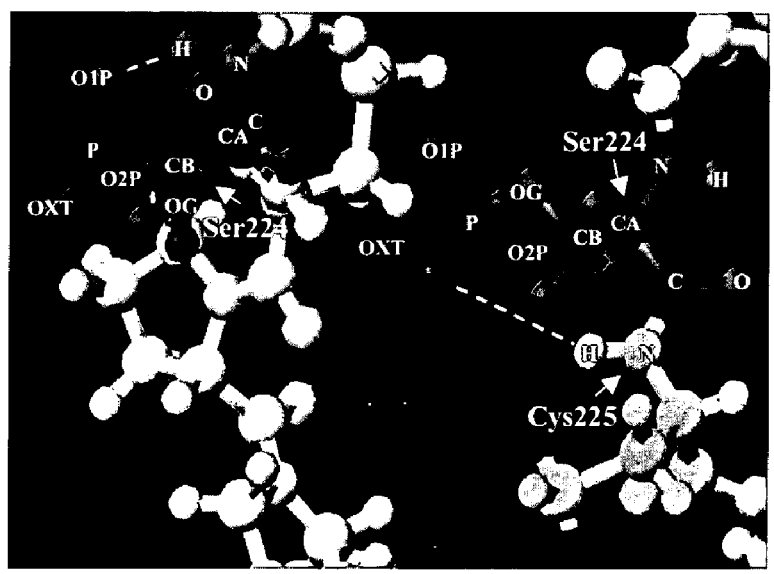

The models of MAb-WW6 and phosphorylated MAb-WW6 are shown in FIG. 7G and FIG. 9G. After phosphate groups were attached to serine residues (Ser224) on the PKA sites of MAb-WW6, the systematic conformational searches were performed as described herein. For MAb-WW6, similar results were obtained after two systematic searches. Sixty-five conformations were revealed after the search corresponding to Ser224 (heavy chain 1). The search corresponding to Ser224 (heavy chain 2) yielded fifty-four conformations. Analysis of the conformations showed that the phosphate group of the Ser224 of chain 1 had the potential to form a hydrogen bond with either NH group on Cys225 or Ser224 (Table 1, FIG. 14A). In contrast, the phosphate group of the Ser224 of chain 2 could only form a hydrogen bond with Cys225 (Table 1, FIG. 14B).

l. Models of MAb-WW7 and Phosphorylated MAb-WW7

Figure 7H:
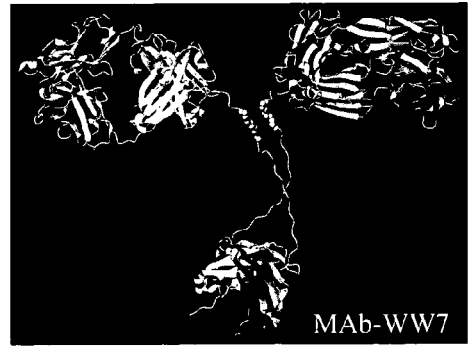
Figure 9H:

The models of MAb-WW7 and phosphorylated MAb-WW7 are shown in FIG. 7H and FIG. 9H. After phosphate groups were attached to serine residues (Ser224) on the PKA sites of MAb-WW7, the systematic conformational searches were performed as described herein. For MAb-WW7, similar results were obtained after two systematic searches.

Figure 15A:
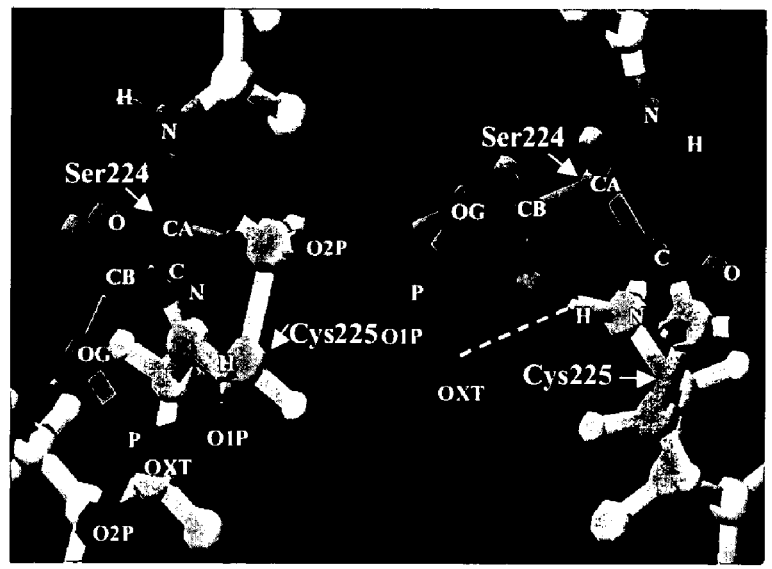
FIG. 15 depicts the stabilization of the phosphate moiety on serine 224 in MAb-WW7. A. The side chain of Ser224 stabilized the phosphate moiety through hydrogen bonding between the phosphate and main chain nitrogen on cysteine 225. B. The side chain of Ser224 stabilized the phosphate moiety through hydrogen bonding between the phosphate and main chain nitrogen on cysteine 225 on the left, and hydrogen bonding between the phosphate and main chain nitrogen on cysteine 225 on the right. Serine 224 are shown in magenta, and cysteine 225 in green. The serine carbons are: C, main chain carbonyl carbon; CA, alpha carbon; CB, beta carbon to which the phosphate (P) is attached through the serine oxygen (OG). Other symbols are: OXT, first oxygen of the phosphate; O1P, second oxygen of phosphate; O2P, third oxygen on phosphate; H, hydrogen in hydrogen bonds from amino acid nitrogens (N) to phosphate oxygens.
Figure 15B:
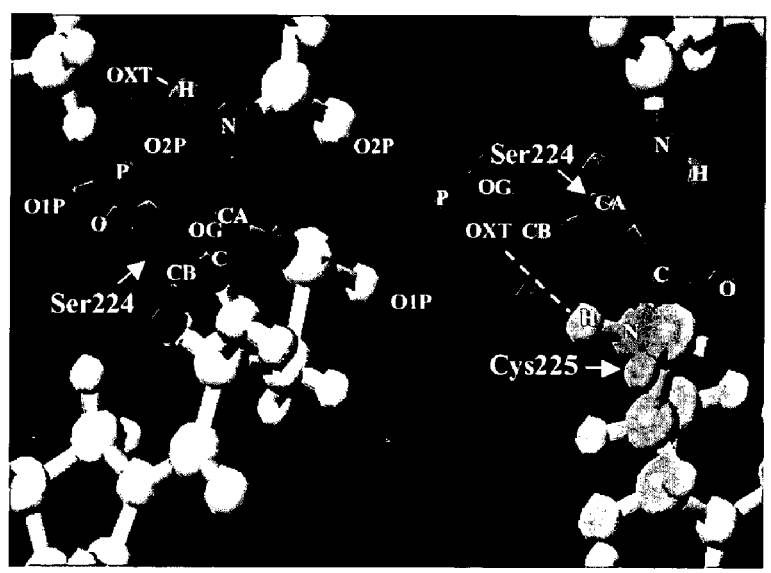

Sixty-four conformations were revealed after the search corresponding to Ser224 (heavy chain 1). The search corresponding to Ser224 (heavy chain 2) yielded fifty-six conformations. Analysis of the conformations showed that the phosphate group of the Ser224 of chain 1 had the potential to form a hydrogen bond with either NH group on Cys225 or Ser224 (Table 1, FIG. 15A). In contrast, the phosphate group of the Ser224 of chain 2 could only form a hydrogen bond with Cys225 (Table 1, FIG. 15B).

m. Models of MAb-WW8 and Phosphorylated MAb-WW8

Figure 7I:
Figure 9I:
Figure 16A:
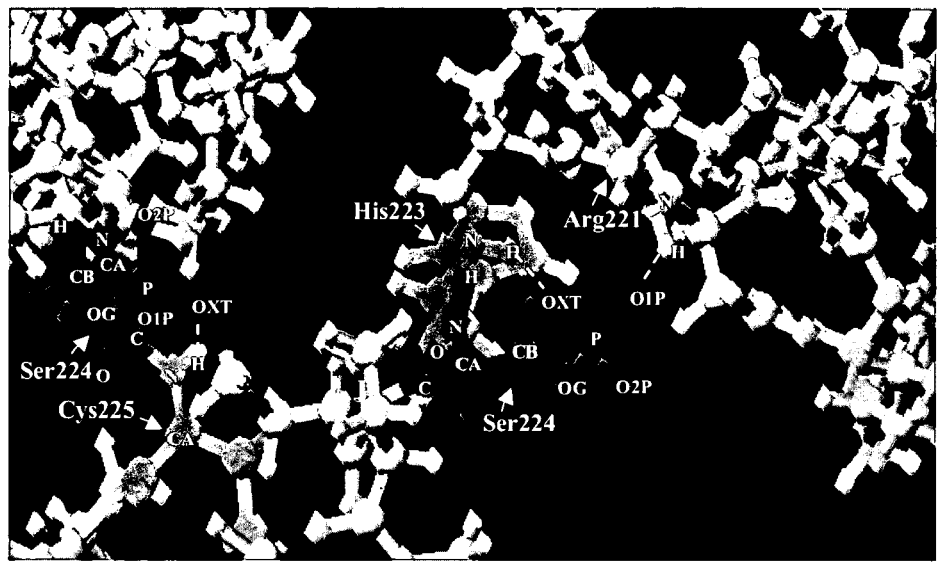
FIG. 16 depicts the stabilization of phosphate moiety on serine 224 in MAb-WW8. A. The side chain of Ser224 stabilized the phosphate moiety through hydrogen bonding either between the phosphate and main chain nitrogen on cysteine 225 (on the left), or between the phosphate and main chain nitrogen on both histidine 223 and arginine 221 (on the right). B. The side chain of Ser224 stabilized the phosphate moiety through hydrogen bonding either between the phosphate and main chain nitrogen on serine 224 (on the left), or between the phosphate and main chain nitrogen on both histidine 223 and arginine 221 (on the right). The serine carbons are: C, main chain carbonyl carbon; CA, alpha carbon; CB, beta carbon to which the phosphate (P) is attached through the serine oxygen (OG). Other symbols are: OXT, first oxygen of the phosphate; O1P, second oxygen of phosphate; O2P, third oxygen on phosphate; H, hydrogen in hydrogen bonds from amino acid nitrogens (N) to phosphate oxygens.
Figure 16B:
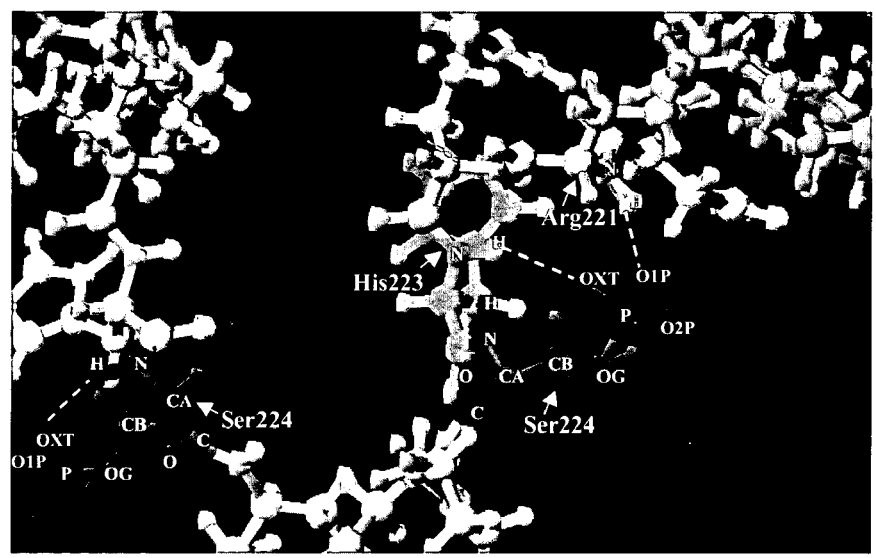

The models of MAb-WW8 and phosphorylated MAb-WW8 are shown in FIG. 7I and FIG. 9I. After phosphate groups were attached to serine residues (Ser224) on the PKA sites of MAb-WW8, the systematic conformational searches were performed as described herein. For MAb-WW8, sixty-two conformations were revealed after the search corresponding to Ser224 (heavy chain 1). The search corresponding to Ser224 (heavy chain 2) yielded thirty-nine conformations. Analysis of the conformations showed that the phosphate group of the Ser224 of chain 1 had the potential to form a hydrogen bond with either NH group on Cys225 or Ser224 (Table 1, FIG. 16A). In contrast, the phosphate group of the Ser224 of chain 2 could form hydrogen bonds with NH groups on both Arg221 and His223 (Table 1, FIG. 16B).

3. Hypotheses

According to the systematic searches shown in Table 1, we observed that on some constructs (MAb-chCC49K1, MAb-CC49CKI, MAb-CC49CKII, MAb-CC49Tyr, MAb-chCC49-6P, MAb-WW5, -WW6, -WW7 and -WW8), the attached phosphate groups had much more allowed conformations than the others (MAb-WW1, -WW2, -WW3 and -WW4). Since the more allowed conformations might suggest easier accessibility of the enzymes to the recognition site, we therefore hypothesized that the greater the number of allowed conformations, the easier accessibility of the enzymes to the recognition site, the more efficient the phosphorylation. According to this hypothesis, we predicted that MAb-chCC49-6P, MAb-WW5, -WW6, -WW7 and -WW8 would be radiolabeled by PKA to a much higher specific activity than the other mutant MAbs, MAb-WW1, -WW2, -WW3 and -WW4.

Another phenomenon we noticed from Table 1 was that the phosphates on the modified MAbs had different potentials to form hydrogen bonds with the neighboring amino acid residues. On some constructs (MAb-WW2, -WW3, -WW5, -WW6, -WW7 and -WW8), all of the attached phosphates could form hydrogen bonds with the surrounding amino acid residues. However, on the other constructs, none or only some of the attached phosphates could form hydrogen bonds (MAb-chCC49K1, MAb-CC49CKI, MAb-CC49CKII, MAb-CC49Tyr, MAb-chCC49-6P, MAb-WW1 and MAb-WW4). Since formation of hydrogen bonds physically stabilizes the phosphate moiety, we hypothesized that the greater the potential for hydrogen bond formation, the greater the resistance of the phosphate to hydrolysis. That is, the stronger the potential to form hydrogen bonds, the more stable the attached $^{32}P$ would be. In other words, the stability of the attached phosphate is compromised if it cannot form hydrogen bond(s) with the neighboring amino acids. According to this hypothesis, the stabilities of the phosphates on MAb-WW2, -WW3, -WW5, -WW6, -WW7 and -WW8 would be greater than those on MAb-chCC49K1, MAb-CC49CKI, MAb-CC49CKII, MAb-CC49Tyr, MAb-chCC49-6P, MAb-WW1 and MAb-WW4.

4. Construction of MAb-chCC49-6P, MAb-WW1, MAb-WW2, MAb-WW3, MAb-WW4, MAb-WW5, MAb-WW6, MAb-WW7 and MAb-WW8 a. Construction of MAb-chCC49-6P

Figure 17:
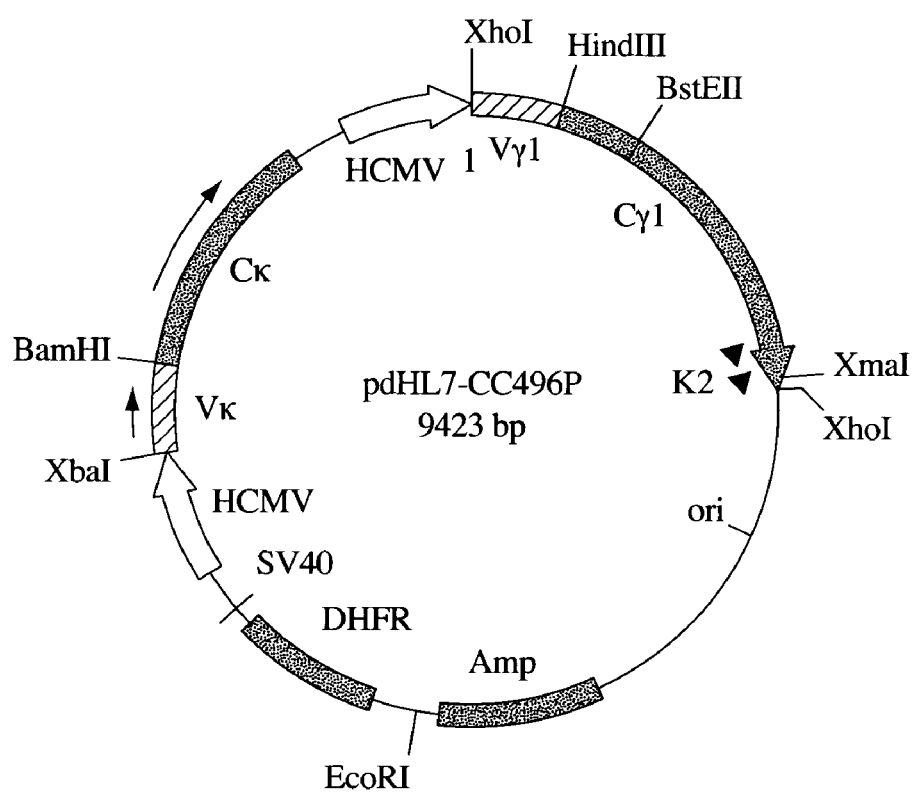
FIG. 17 depicts the expression vector, pdHL7-CC49-6P, constructed for the expression of MAb-CC49-6P.

The plasmid pdHL7-CC49-6P (FIG. 17) that expresses MAb-chCC49-6P was constructed by cloning two synthetic fragments K2 (FIG. 3) into the XmaI site of the expression vector pdHL7-CC49K1. The details of the construction are described herein.

b. Construction of MAb-WW1

Figure 18A:
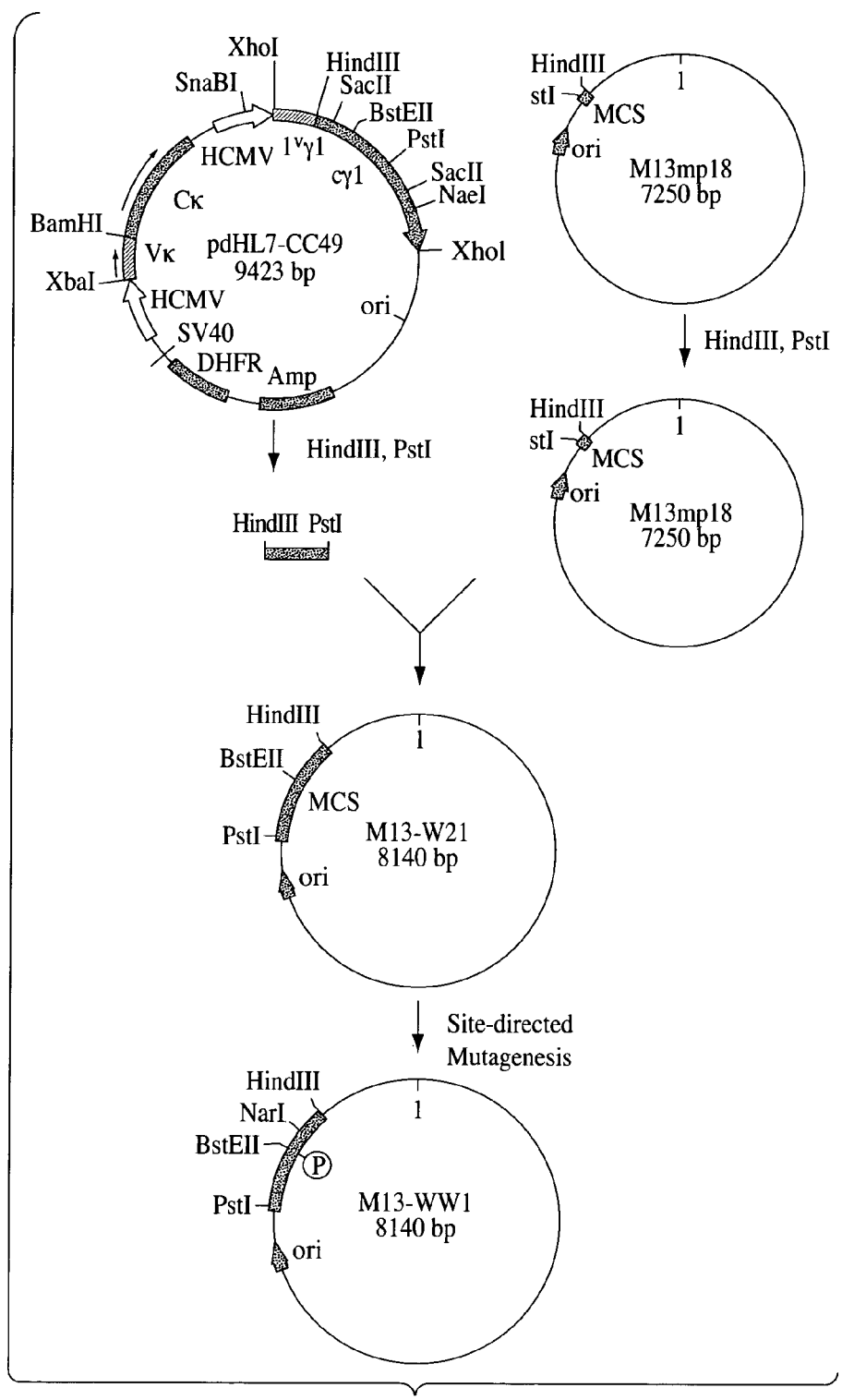
FIG. 18 illustrates the construction of pWW1. Because the construction is extensive, the figure provides the details in sequential parts (FIGS. 18A and 18B).
Figure 18B:
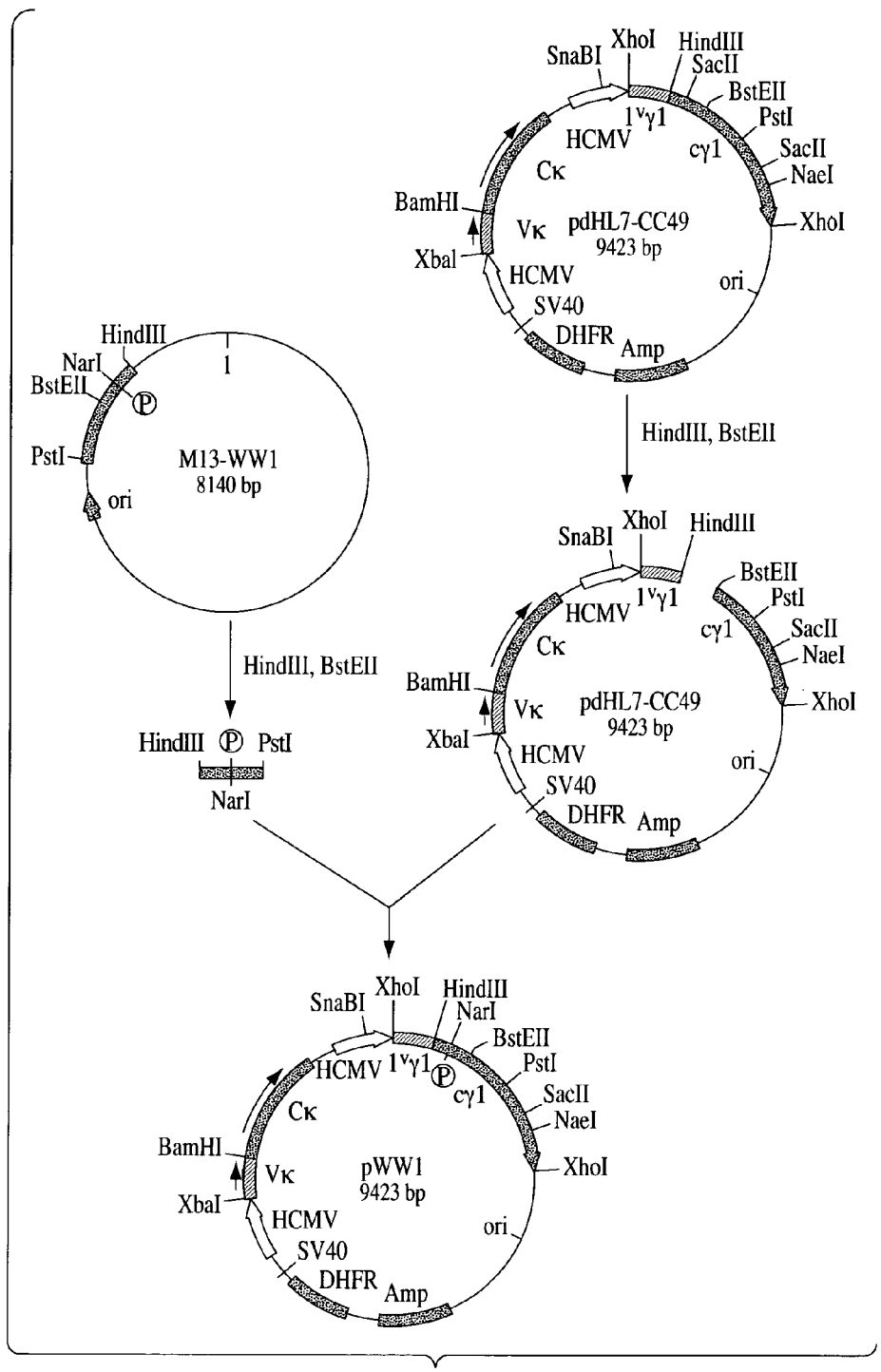

The plasmid pWW1 that expresses MAb-WW1 was constructed as shown in FIGS. 18A and B. The details of the construction are described herein.

c. Construction of MAb-WW2

Figure 19A:
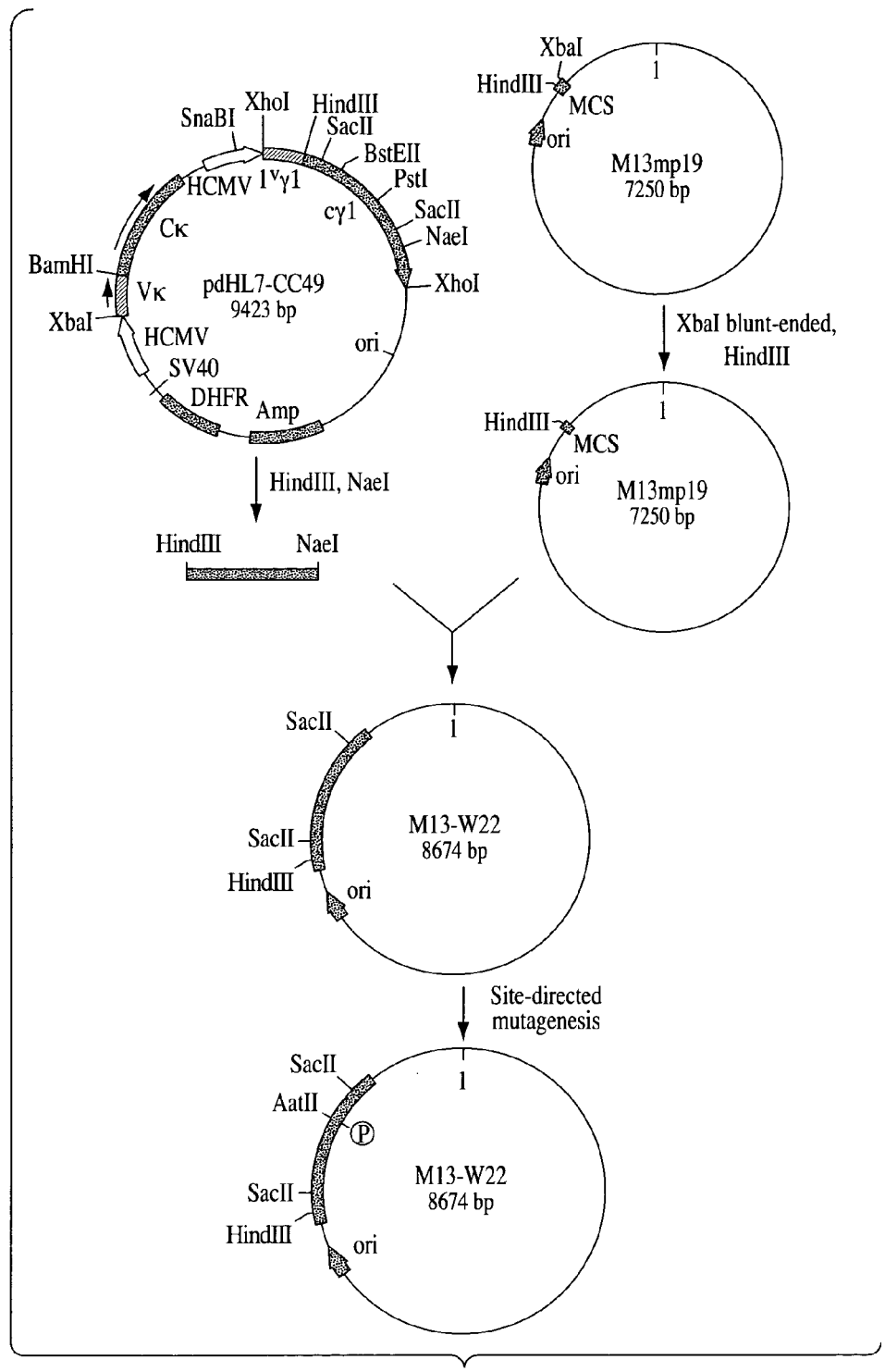
FIG. 19 shows the construction of pWW2. Because the construction is extensive, the figure provides the details in sequential parts (FIGS. 19A and 19B).
Figure 19B:
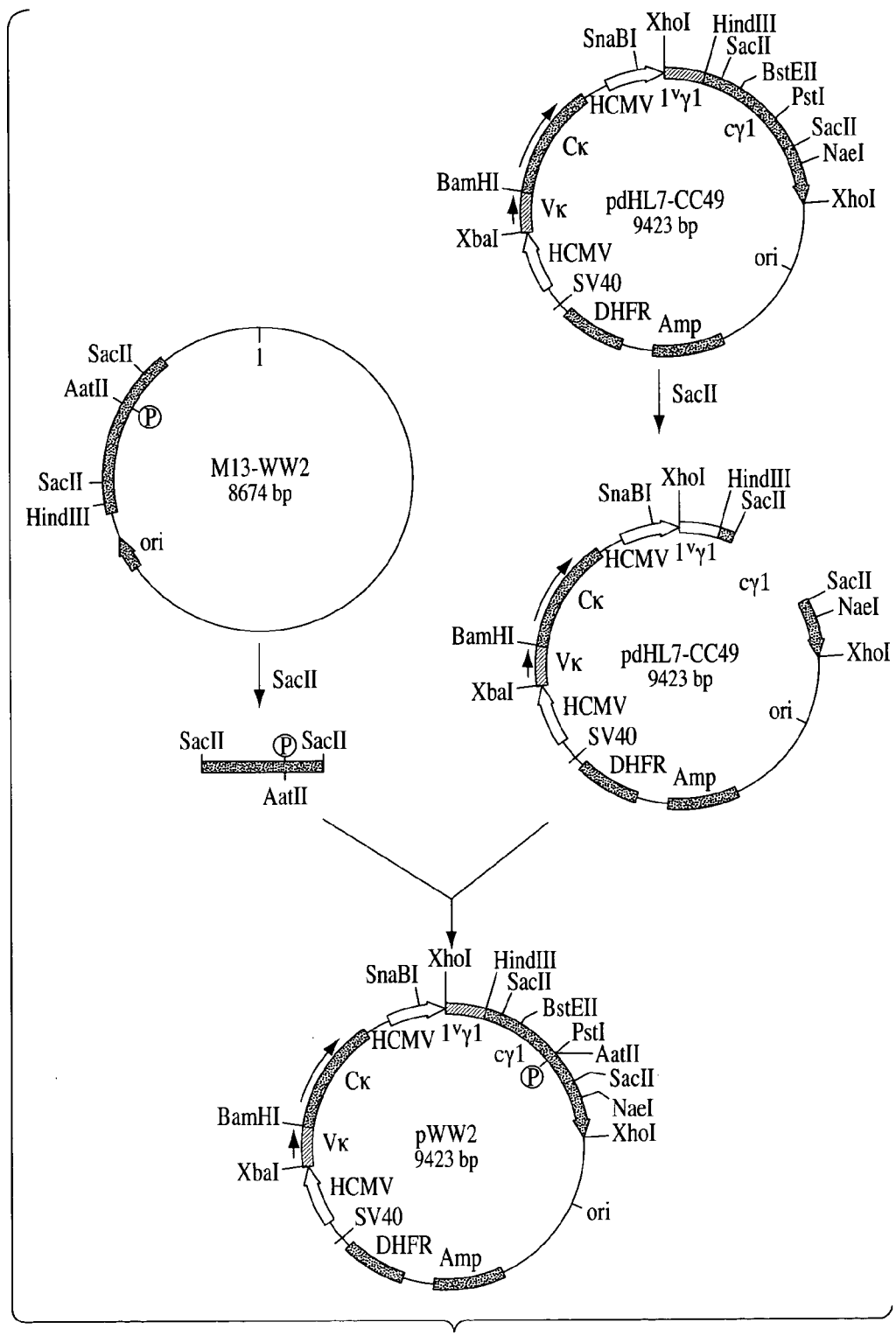
Figure 20A:
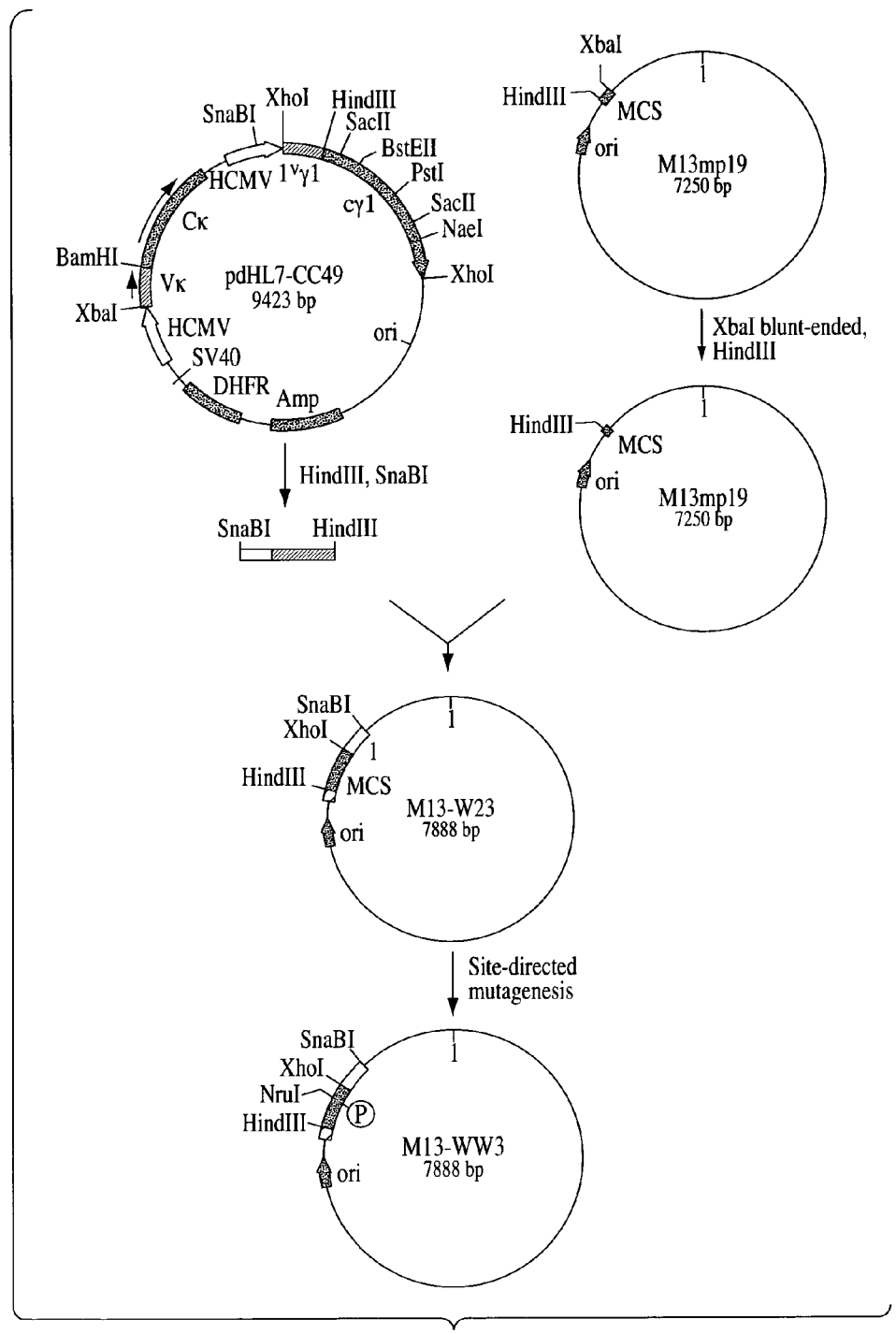
FIG. 20 shows the construction of pWW3. Because the construction is extensive, the figure provides the details in three sequential parts (FIGS. 20A, 20B and 20C).
Figure 20B:
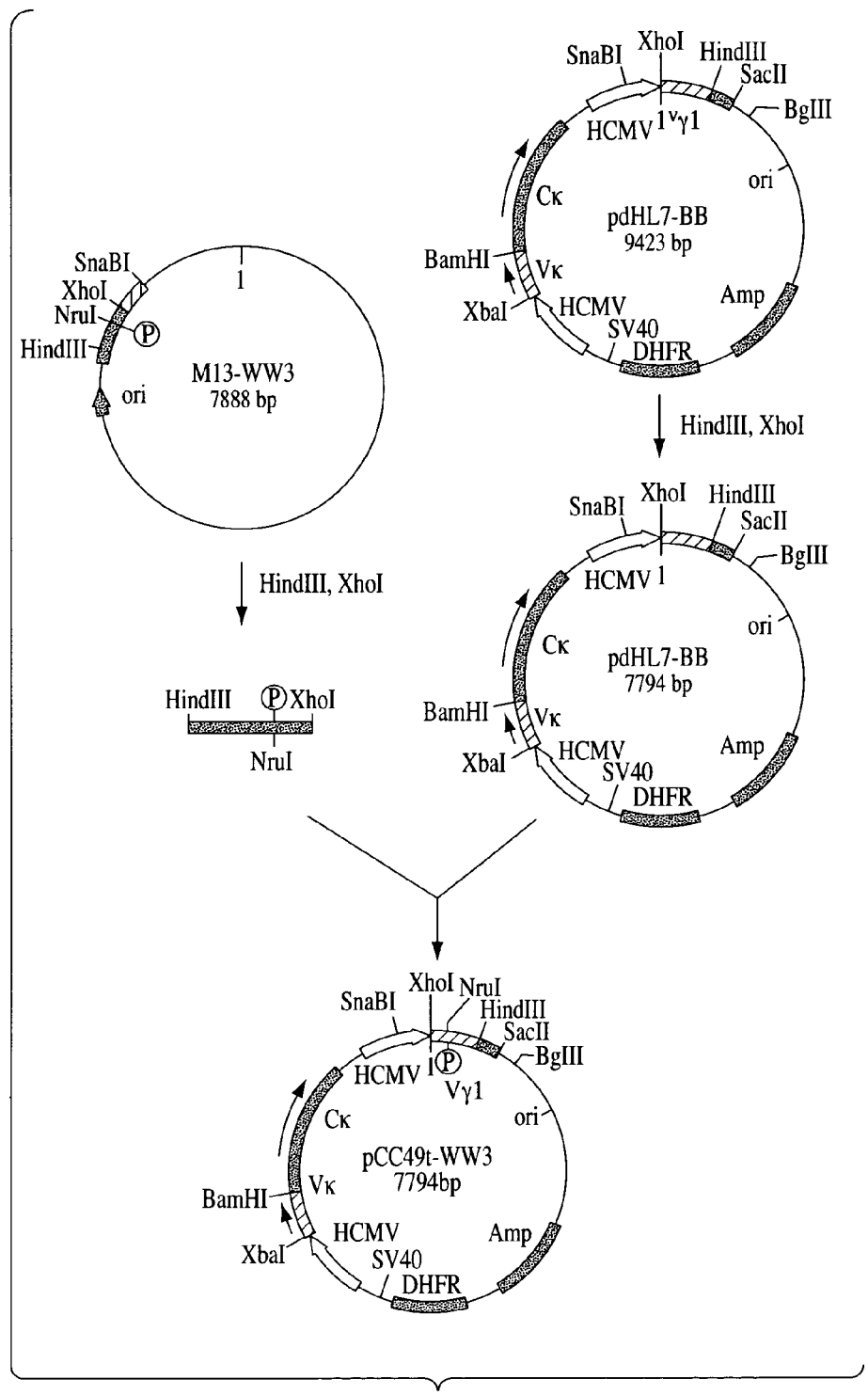
Figure 20C:
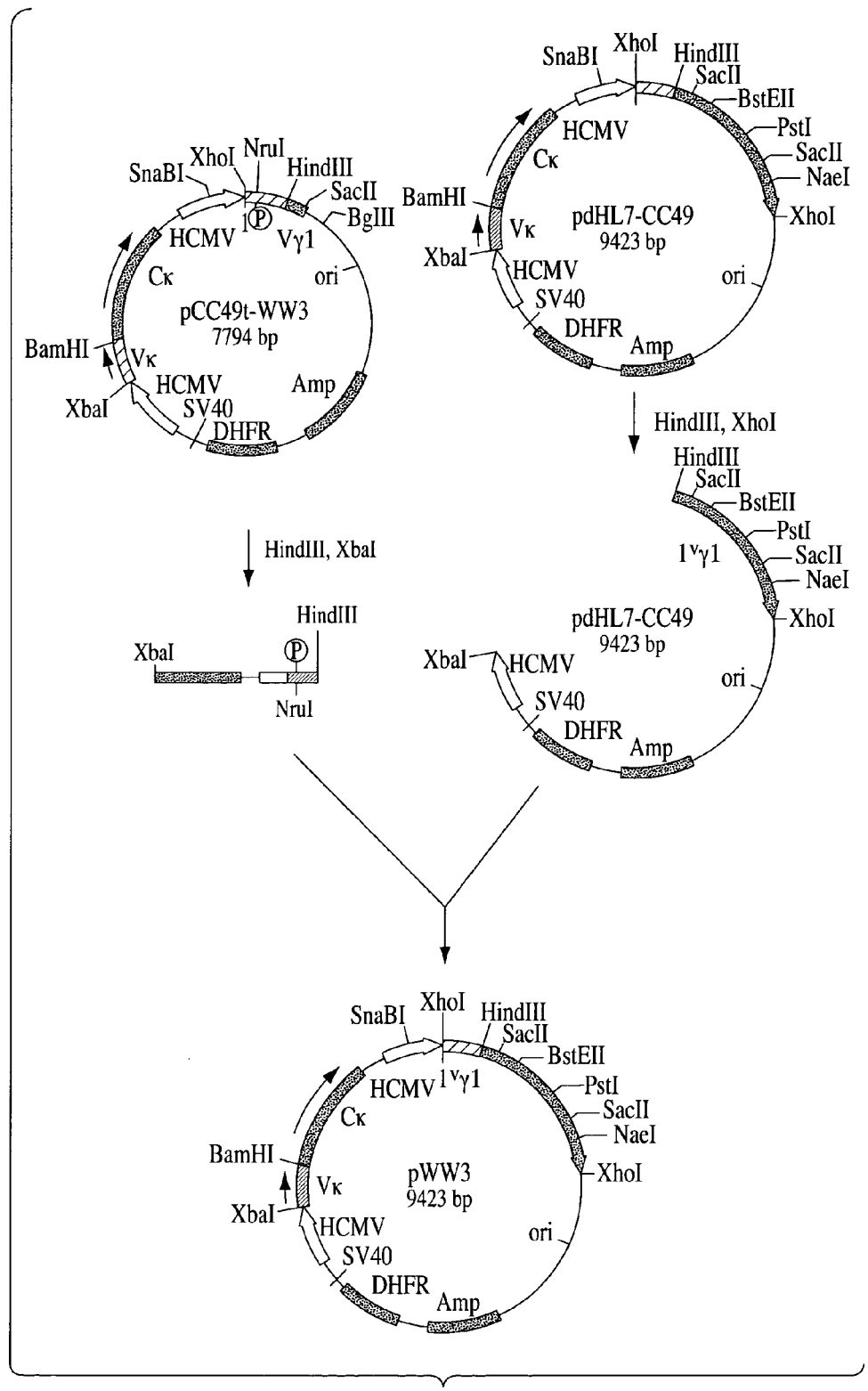

The plasmid pWW2 that expresses MAb-WW2 was constructed as shown in FIGS. 19A and B. The details of the construction are described herein.

d. Construction of MAb-WW3

The plasmid pWW3 that expresses MAb-WW3 was constructed as shown in FIGS. A, B and C. The details of the construction are described herein.

e. Construction of MAb-WW4

Figure 21A:
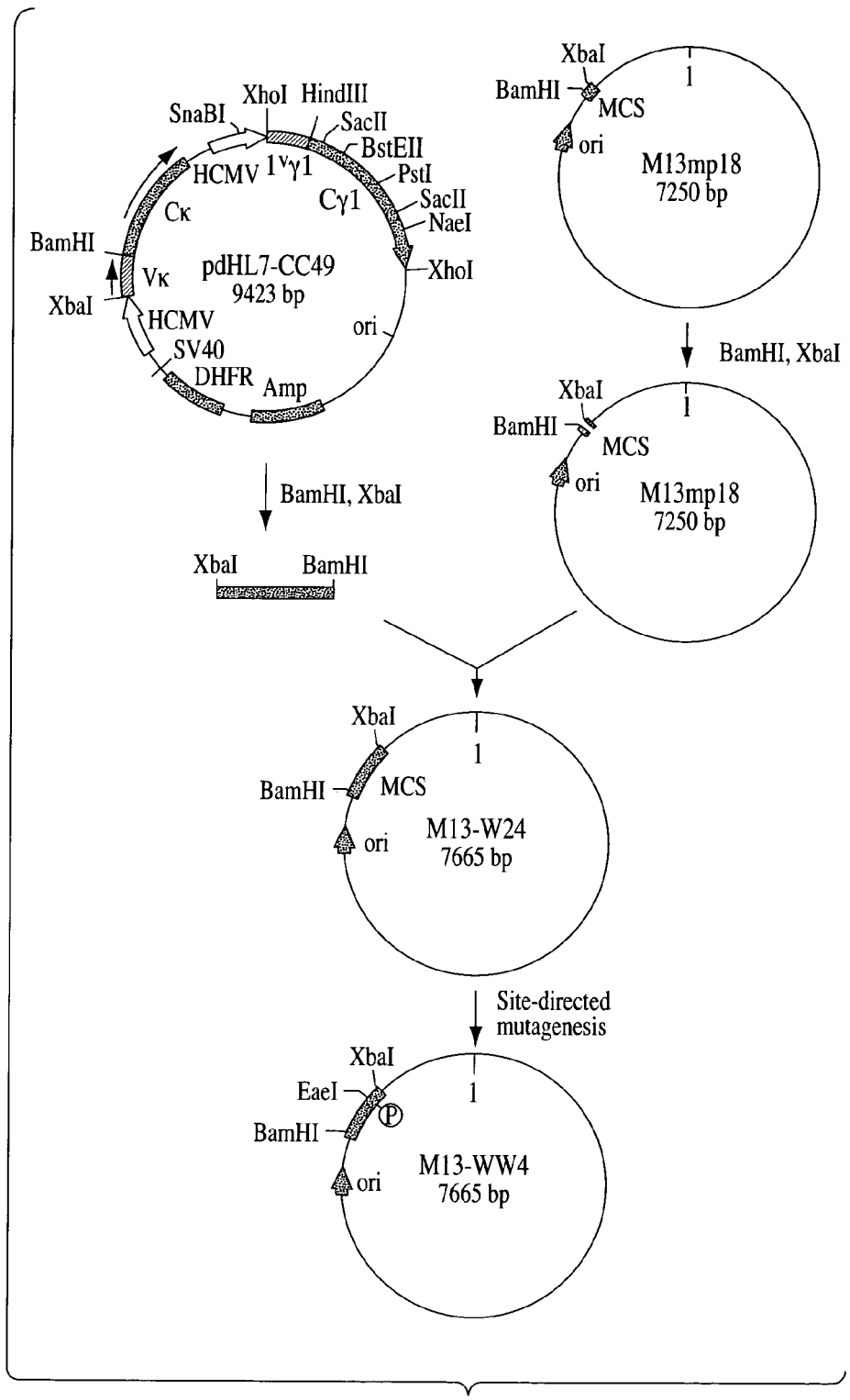
FIG. 21 shows the construction of pWW4. Because the construction is extensive, the figure provides the details in sequential parts (FIG. 21A and FIG. 21B).
Figure 21B:
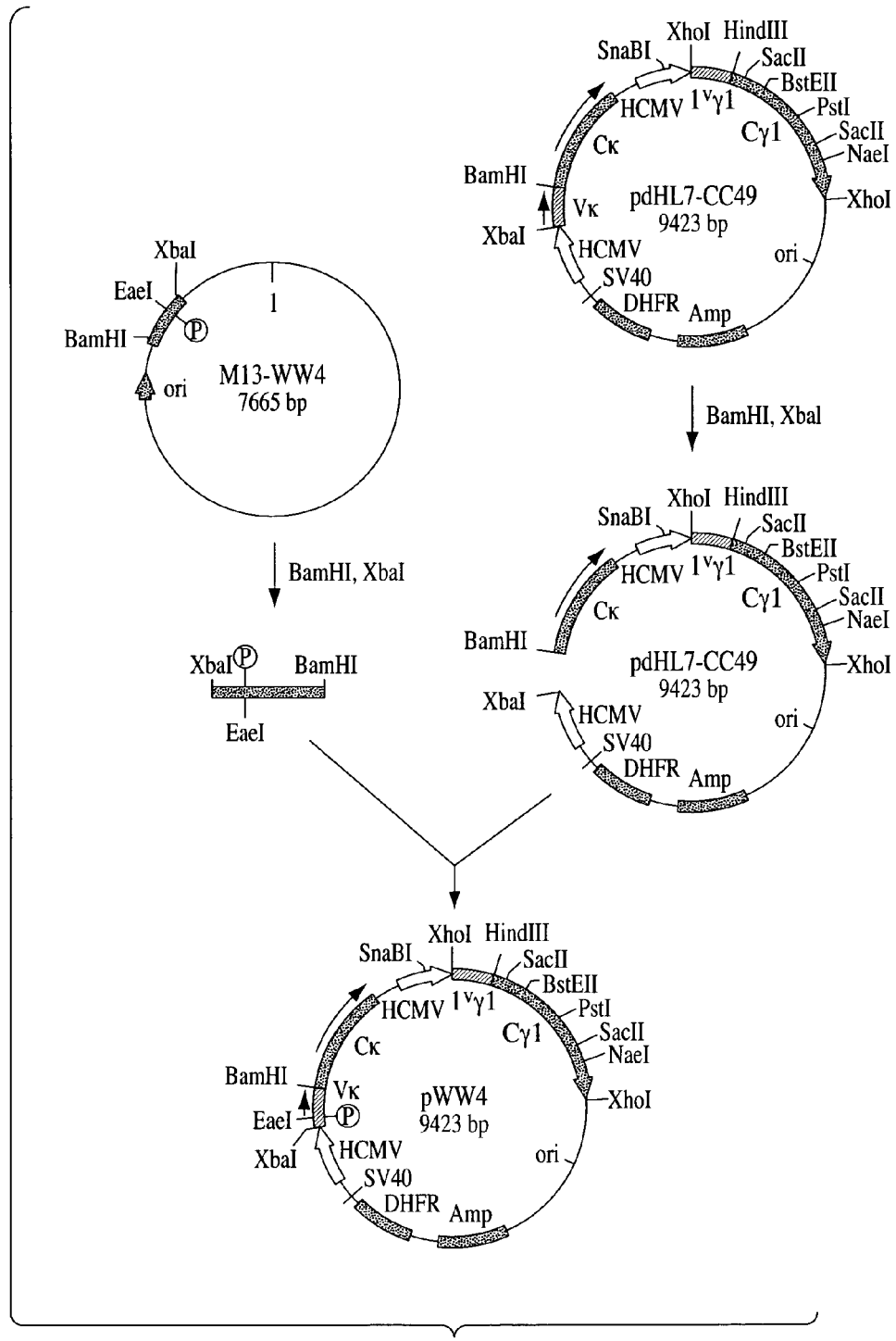

The plasmid pWW4 that expresses MAb-WW4 was constructed as shown in FIGS. 21A and B. The details of the construction are described herein.

f. Construction of MAb-WW5

Figure 22A:
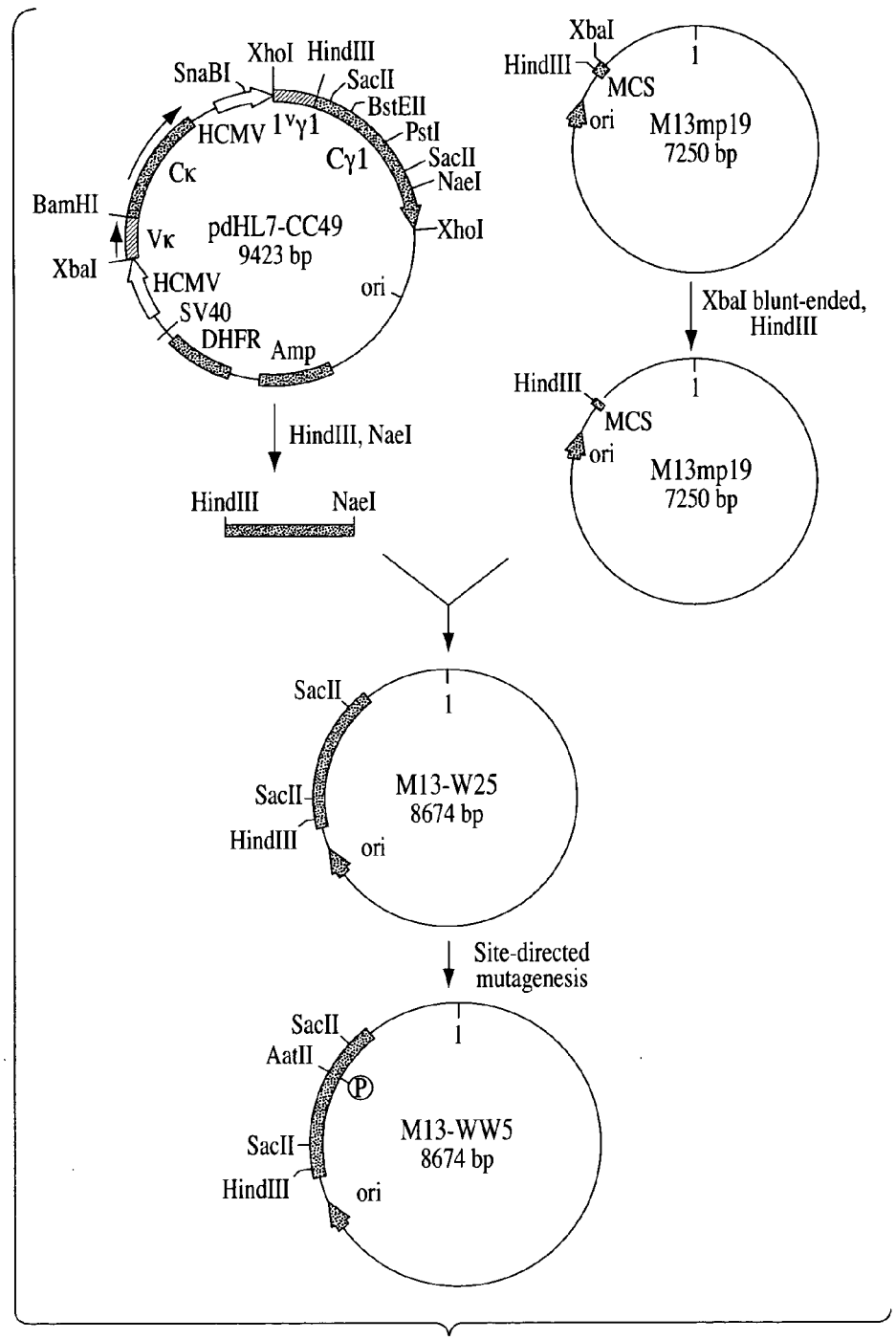
FIG. 22 shows the construction of pWW5. Because the construction is extensive, the figure provides the details in sequential parts (FIGS. 22A and 22B).
Figure 22B:
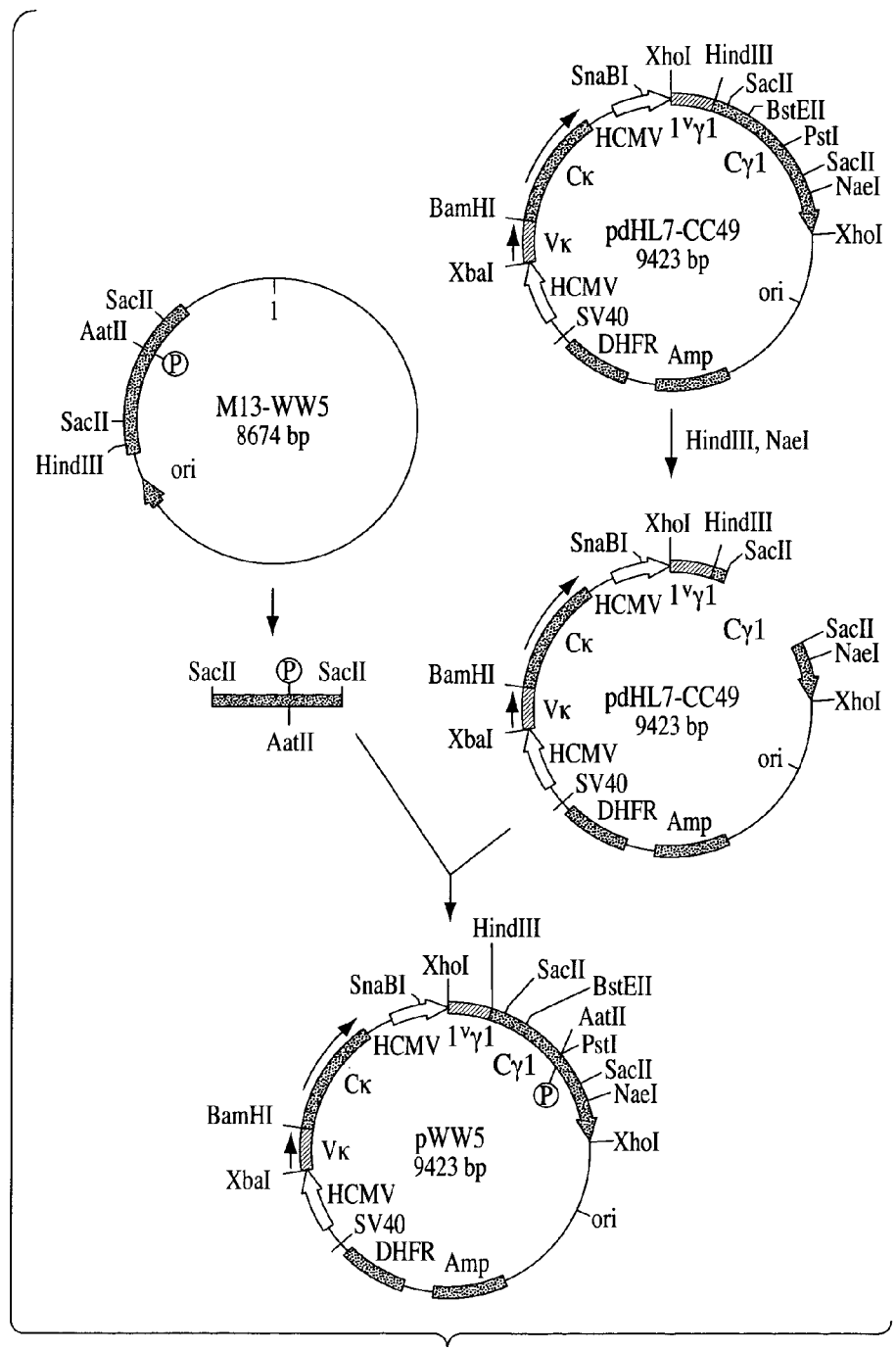

The plasmid pWW5 that expresses MAb-WW5 was constructed as shown in FIGS. 22A and B. The details of the construction are described herien.

g. Construction of MAb-WW6

Figure 23A:
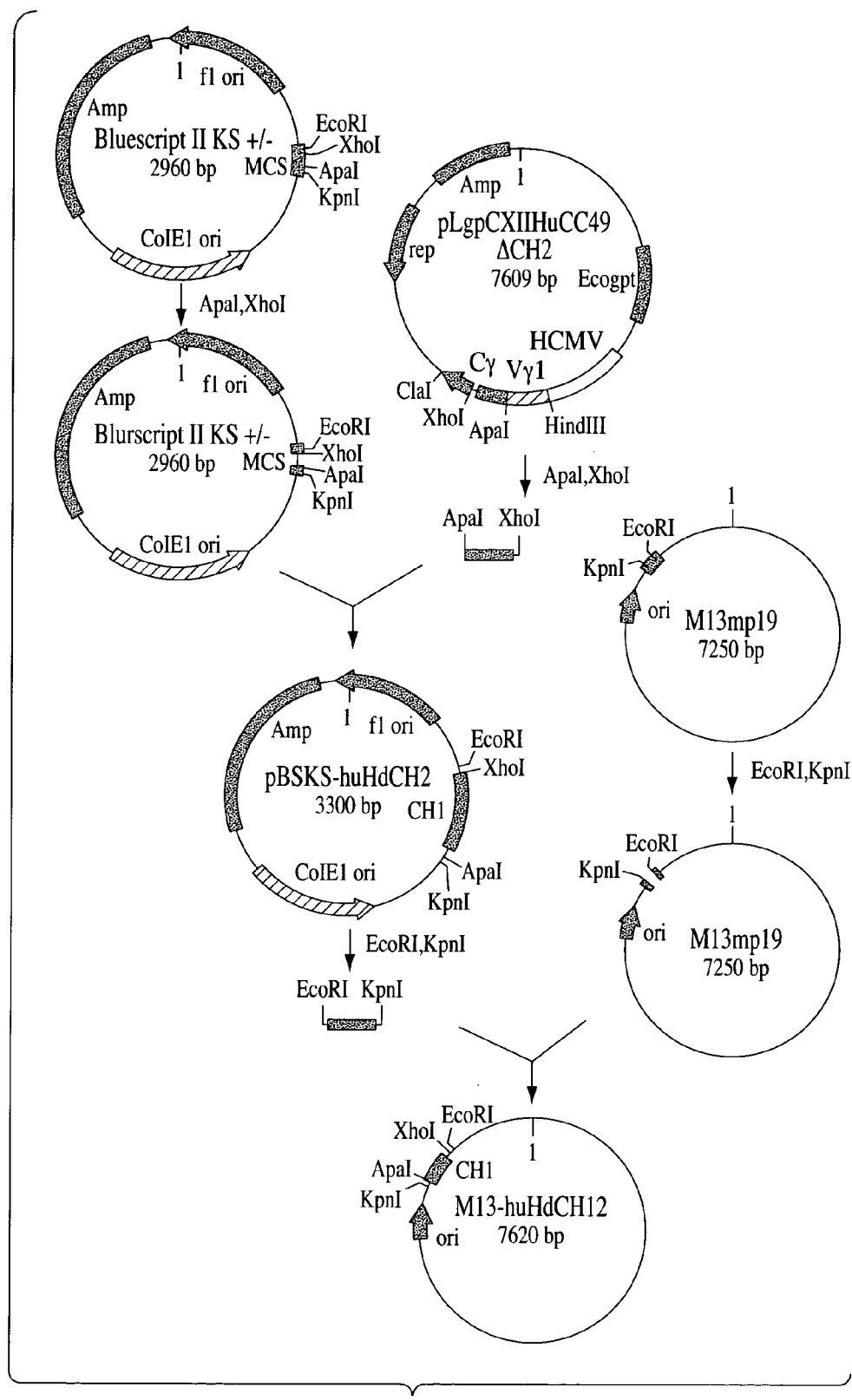
FIG. 23 shows the construction of pLgpCXIIIHuWW5. Because the construction is extensive, the figure provides the details in sequential parts (FIGS. 23A and 23B).
Figure 23B:
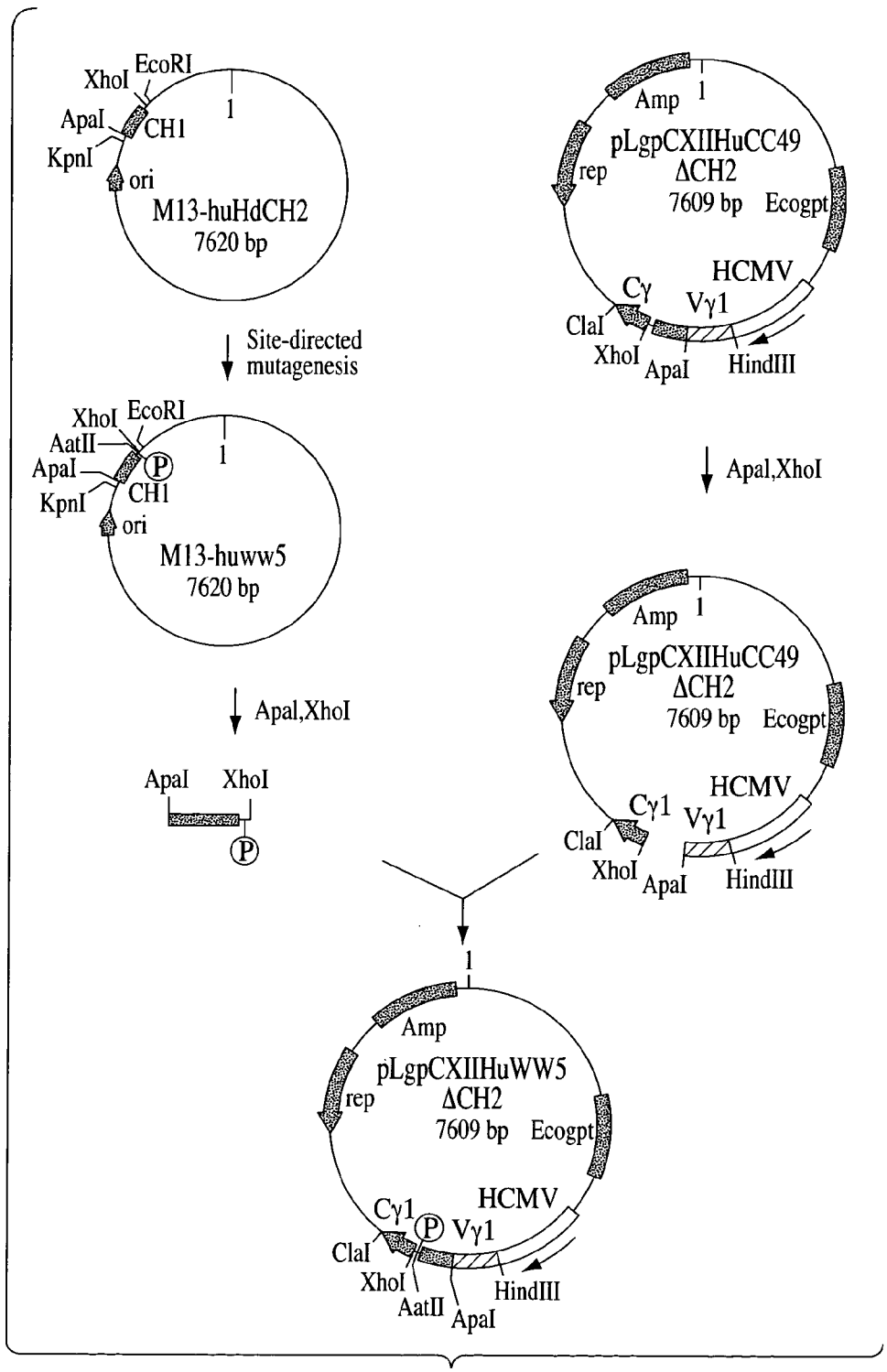

The plasmid pLgpCXIIHuWW5 that expresses the heavy chain of the MAb-WW6 was constructed as shown in FIGS. 23A and B. The details of the construction are described herein.

h. Construction of MAb-WW7

Figure 24:
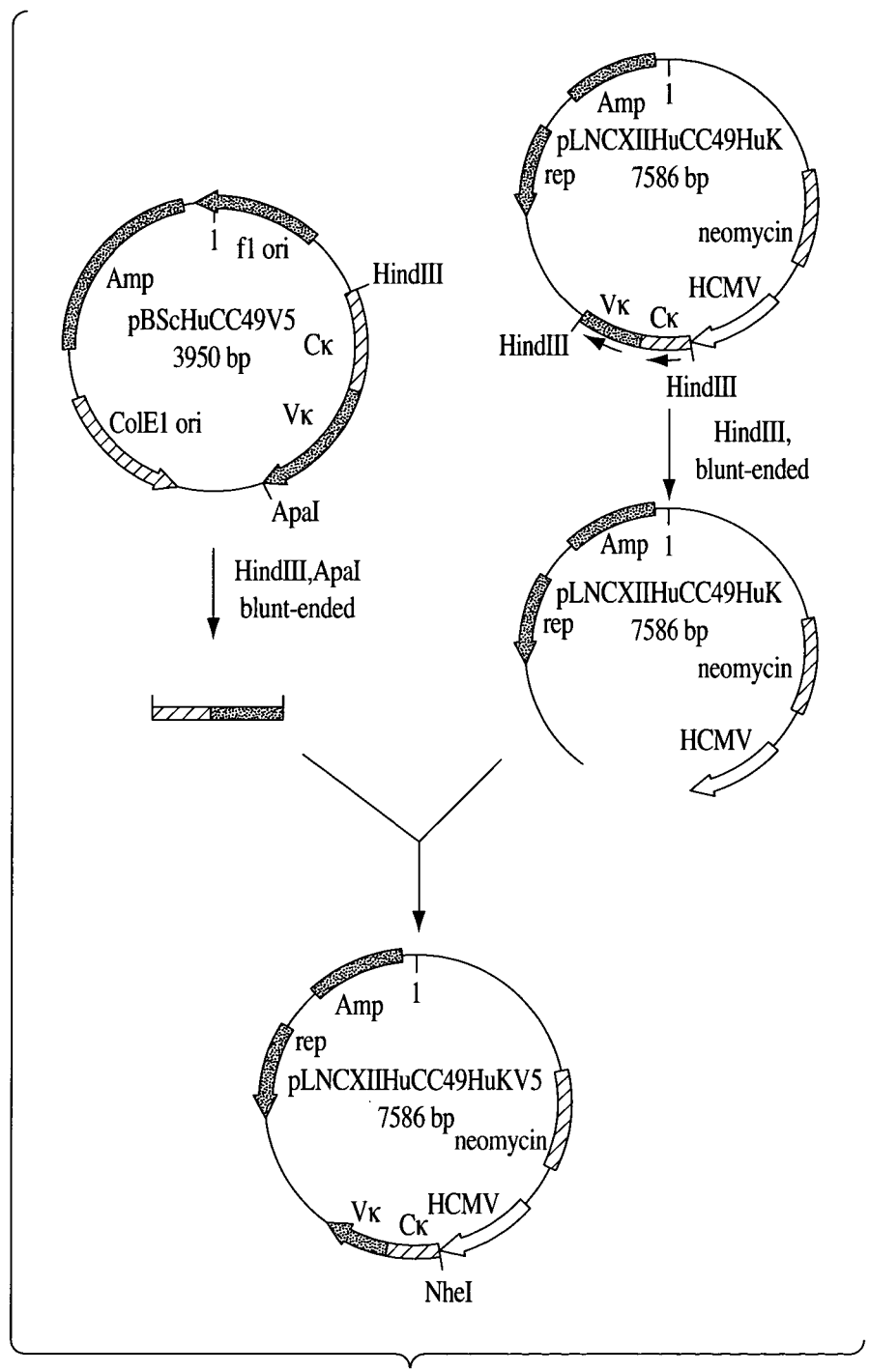
FIG. 24 shows the construction of pLNCXIIIHuCC49HuKV5. The construct pLNCXIIIHuCC49HuKV5 expresses the light chain of the MAb-WW7.
Figure 25:
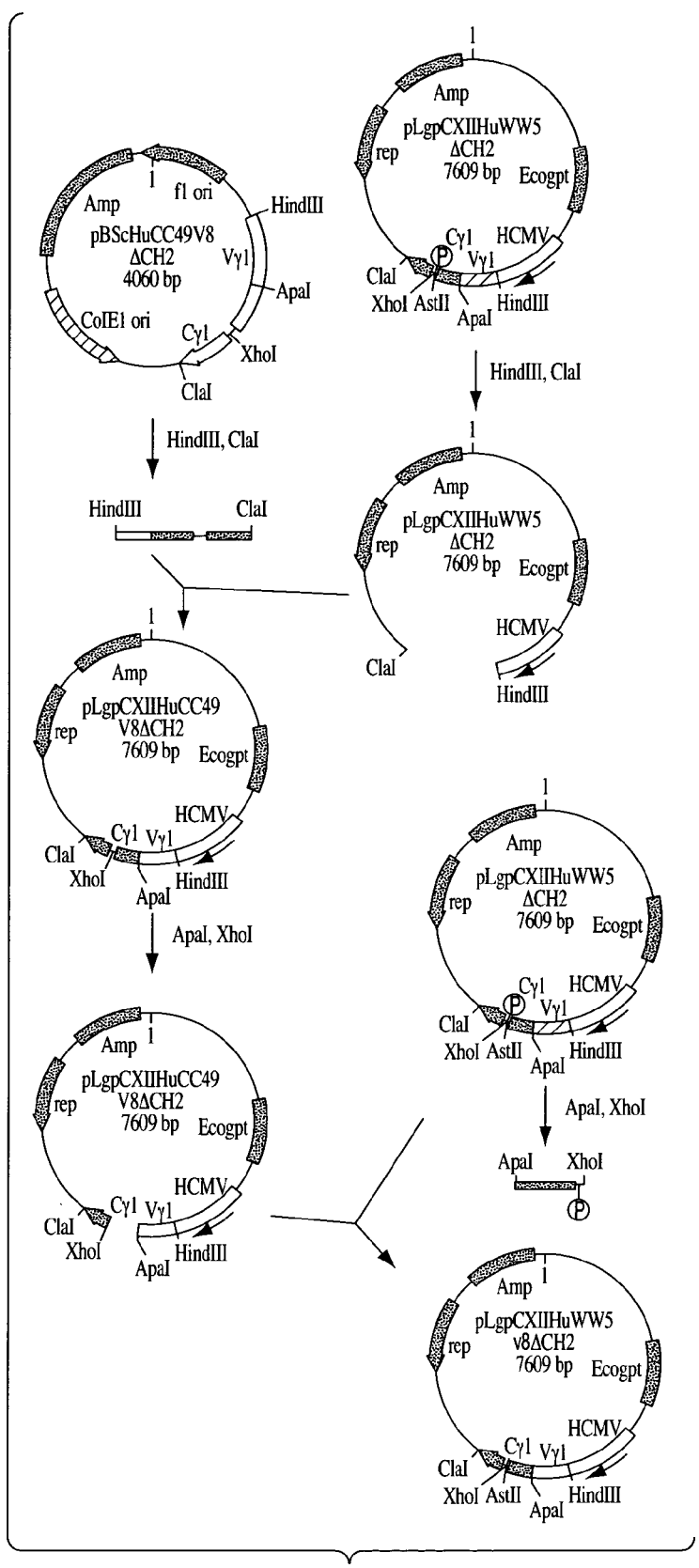
FIG. 25 shows the construction of pLgpCXIIIHuWW5V8ΔCH2. The final construct pLgpCXIIIHuWW5V8ΔCH2 expresses the heavy chain of the MAb-WW7 with the CH2-domain deleted and amino acid substitutions K221R, T222R and T224S in the humanized MAb-CC49.

The plasmid pLNCXIIHuCC49HuKV5 that expresses the light chain of the MAb-WW7 was constructed as shown in FIG. 24, and the plasmid pLgpCXIIHuWW5V8ΔCH2 that expresses the heavy chain of the MAb-WW7 in FIG. 25. The details of the construction are described herein.

i. Construction of MAb-WW8

Figure 26A:
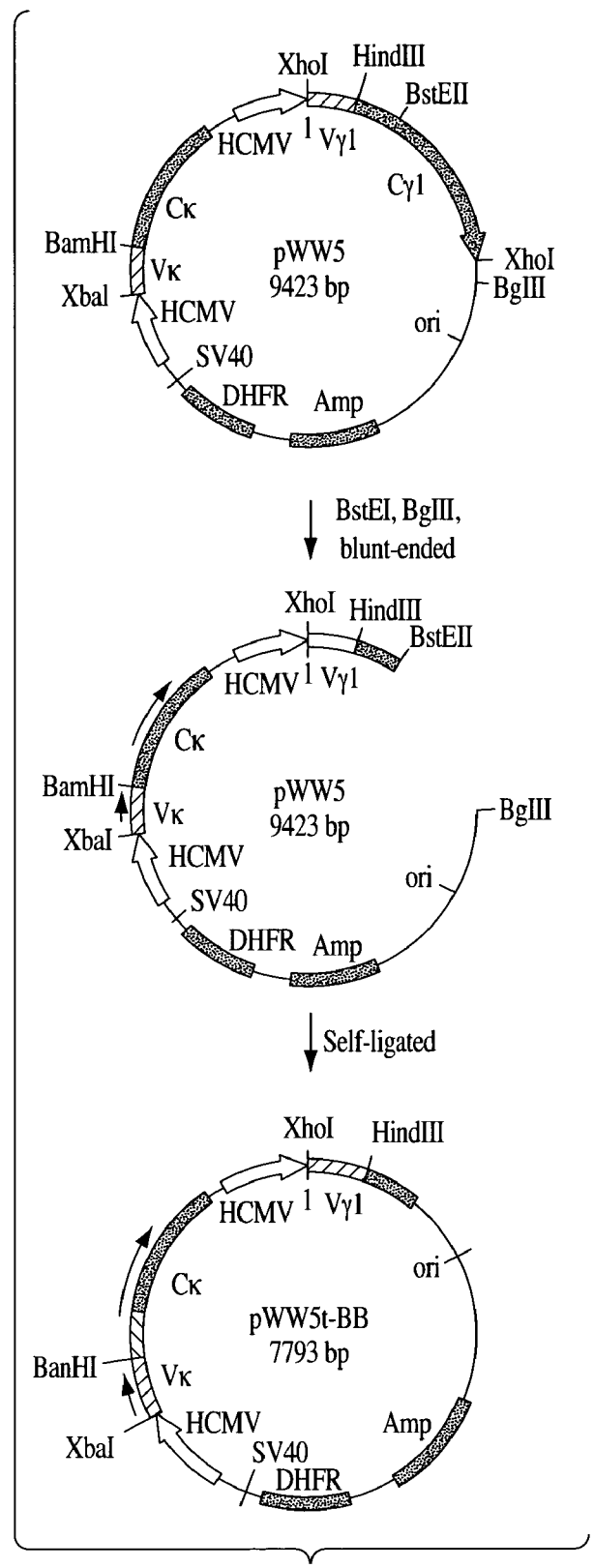
FIG. 26 shows the construction of pWW8. Because the construction is extensive, the figure provides the details in sequential parts (FIGS. 26A, 26B, 26C and 26D).
Figure 26B:
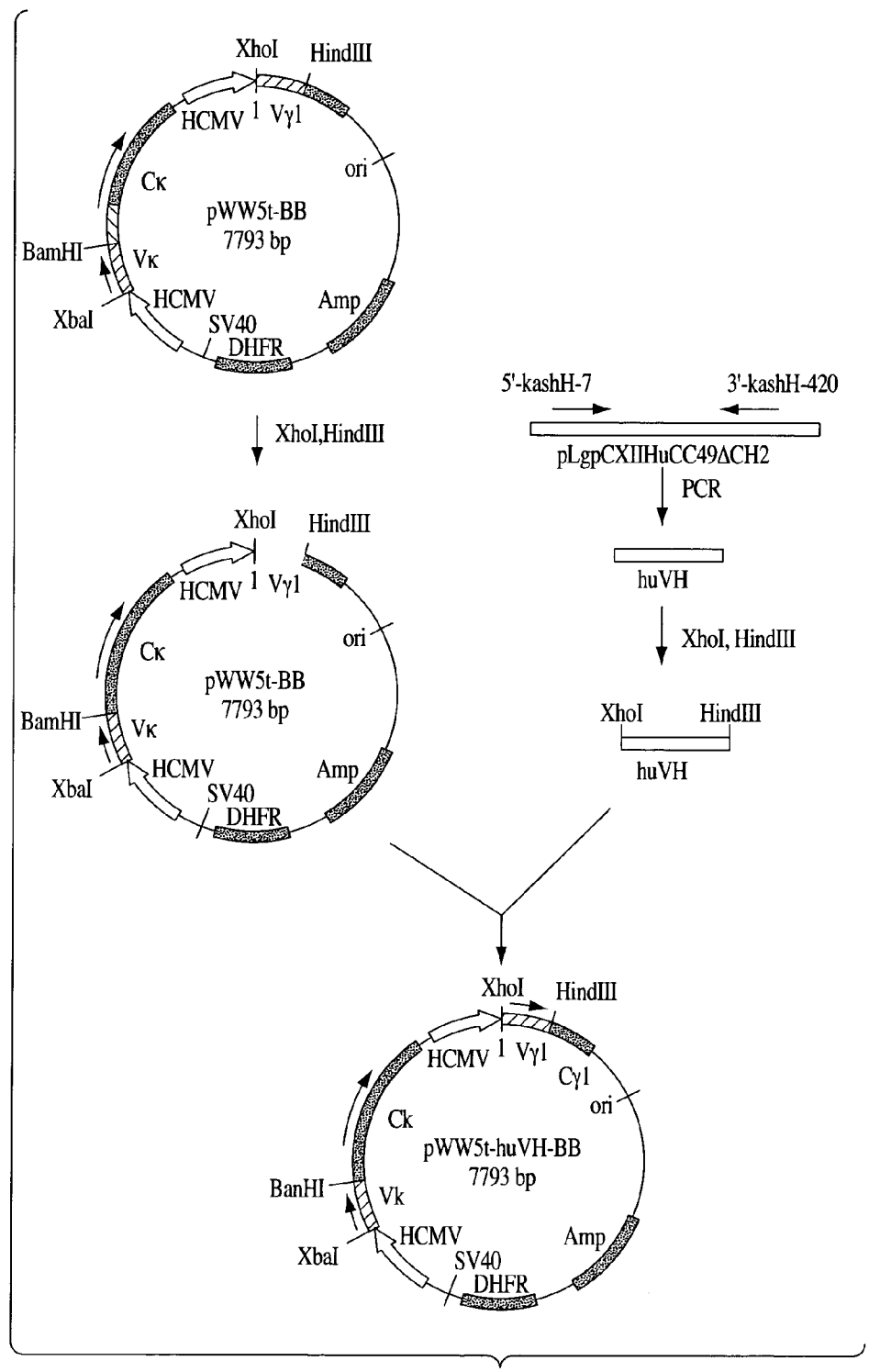
Figure 26C:
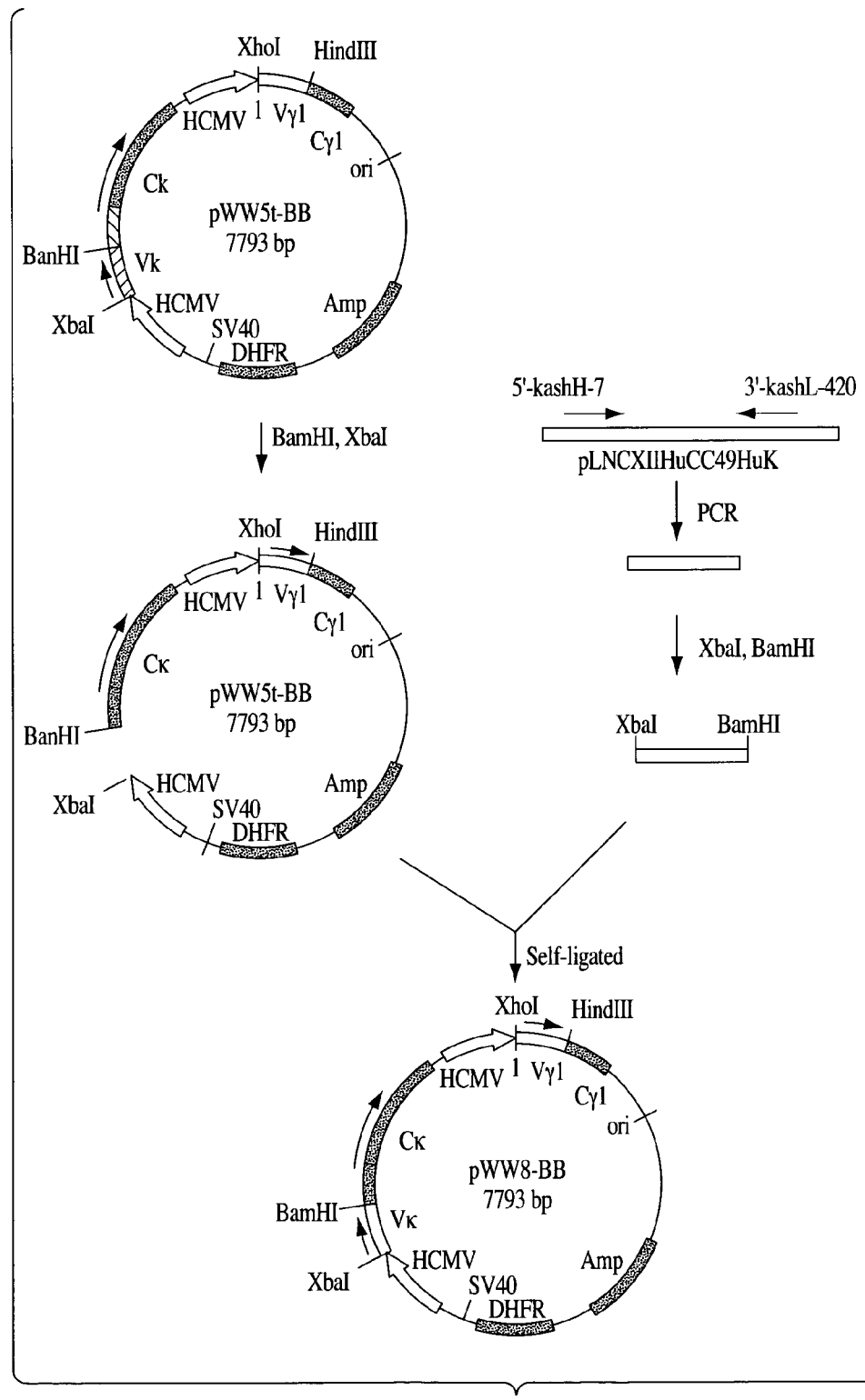
Figure 26D:
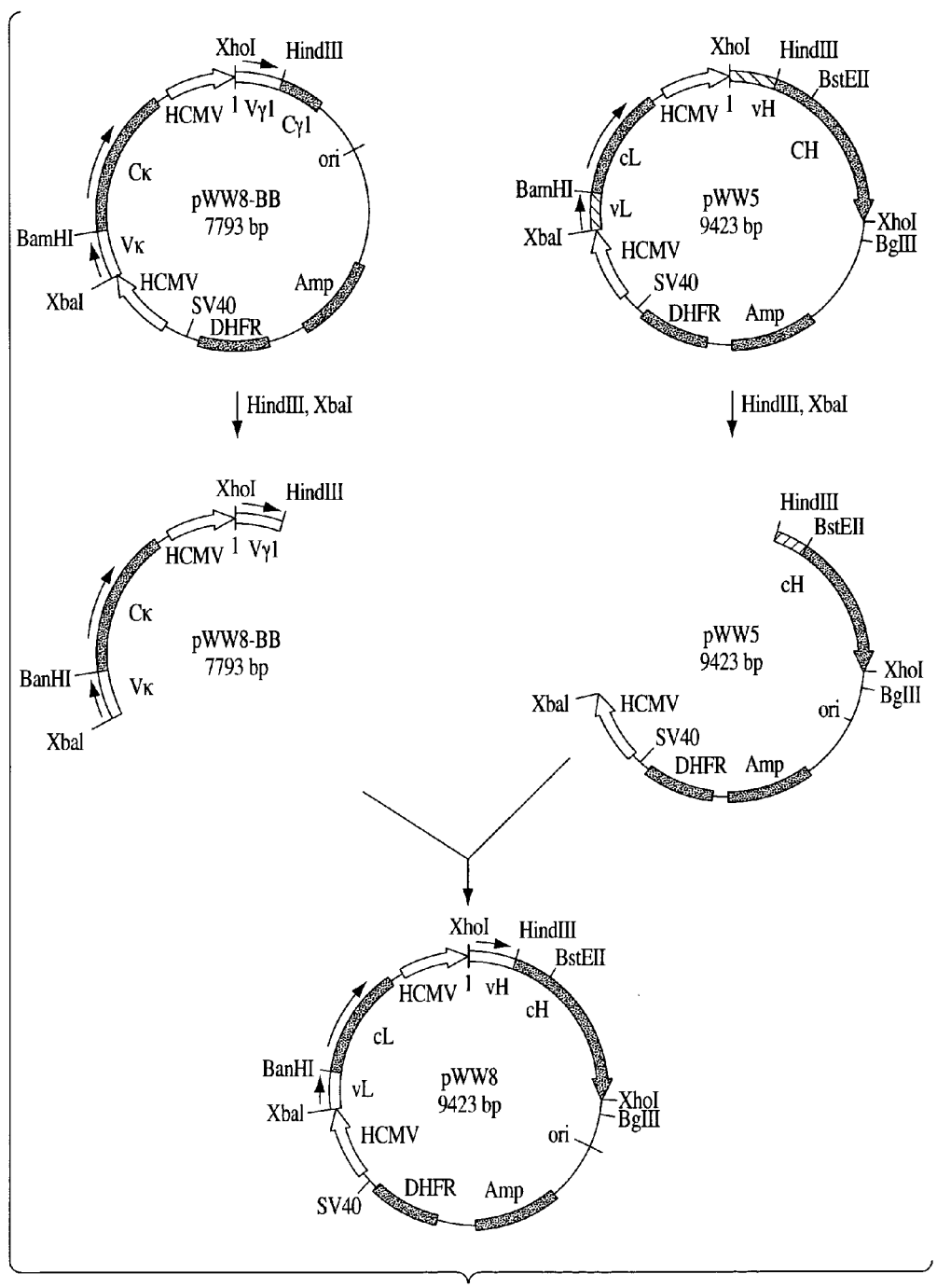
Figure 27F:
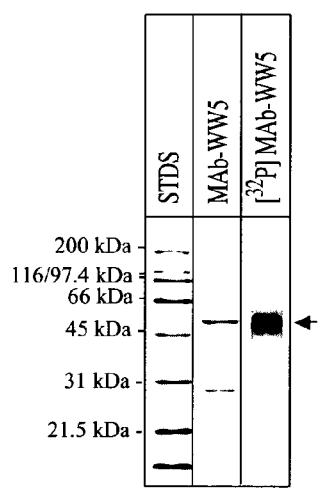
FIG. 27 illustrates an SDS-polyacrylamide gel electrophoresis of the modified MAbs. A: MAb-chCC49-6P represents the gel of unlabeled MAb-chCC49-6P. [$^{32}$P]MAb-CC49-6P represents the autoradiograph of the phosphorylated MAb-chCC49-6P. STDS represents the molecular weight markers (SDS-PAGE standards, broad range, Bio-Rad, Cat. No. 161-0317). The kDa of the markers is shown to the left of panels A and G. Arrows point to the places where the phosphorylated mutant MAbs migrated as seen on the autoradiograph (right lane of each panel). Similar labels are used to represent the SDS-polyacrylamide gel electrophoresis of the other mutant MAbs in B-H.
Figure 27G:
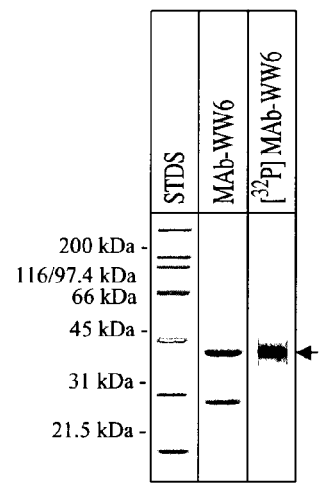
Figure 27H:
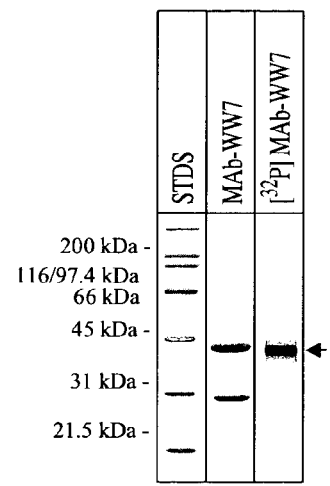

The plasmid pWW8 that expresses the humanized MAb-WW5 was constructed as shown in FIGS. 26A, B, C and D. The details of the construction are described herein.

5. Expression and Purification of Monoclonal Antibodies a. Expression and Purification of MAb-chCC49-6P Stable transfection of mouse myeloma NS0 cells with expression vectors pMAb-chCC49-6P was performed as described herein. The concentration of IgG produced by the clone with highest expression was about 2 µg/ml as determined by a sandwich ELISA. The mutant MAb secreted in the 90 ml of supernatant was purified and concentrated as described herein. The final concentration of purified MAb was 0.9 mg/ml as determined by ELISA.

b. Expression and Purification of MAb-WW1

Stable transfection of mouse myeloma NS0 cells with expression vectors pMAb-WW1 was performed as described herein. The concentration of IgG produced by the clone with highest expression was about 40 µg/ml as determined by a sandwich ELISA. The mutant MAb secreted in the 500 ml of supernatant was purified and concentrated as described herein. The final concentration of purified MAb was 5.3 mg/ml as determined by ELISA.

c. Expression and Purification of MAb-WW2

Stable transfection of mouse myeloma NS0 cells with expression vectors pMAb-WW2 was performed as described herein. The concentration of IgG produced by the clone with highest expression was about 18 µg/ml as determined by a sandwich ELISA. The mutant MAb secreted in the 150 ml of supernatant was purified and concentrated as described herein. The final concentration of purified MAb was 4.5 mg/ml as determined by ELISA.

d. Expression and Purification of MAb-WW3

Stable transfection of mouse myeloma NS0 cells with expression vectors pMAb-WW3 was performed as described herein. The concentration of IgG produced by the clone with highest expression was about 22 µg/ml as determined by a sandwich ELISA. The mutant MAb secreted in the 430 ml of supernatant was purified and concentrated as described herein The final concentration of purified MAb was 0.9 mg/ml as determined by ELISA.

e. Expression and Purification of MAb-WW4

Stable transfection of mouse myeloma NS0 cells with expression vectors pMAb-WW4 was performed as described herein. The concentration of IgG produced by the clone with highest expression was about 7 µg/ml as determined by a sandwich ELISA. The mutant MAb secreted in the 290 ml of supernatant was purified and concentrated as described herein. The final concentration of purified MAb was 35.2 mg/ml as determined by ELISA.

f. Expression and Purification of MAb-WW5

The stable transfection of mouse myeloma NS0 cells with expression vector pMAb-WW5 was performed as described herein. Clone #24, which expressed the highest concentration of IgG, 10 µg/ml as determined by a sandwich ELISA, was chosen for expansion and collection of supernatants. Before purification of MAb-WW5, supernatants from six 150 cm² flasks were pooled. Purification of MAb-WW5 was performed as described herein. The concentration of purified MAb-WW5 was 3.3 mg/ml as determined by ELISA. Then 10 µl aliquots of purified MAb-WW5 were placed in 0.5 ml tubes and stored frozen at −20° C. or below until use.

g. Expression and Purification of MAb-WW6

The stable transfection of mouse myeloma NS0 cells with expression vectors pLNCXIIHuCC49HuK and pLgpCXIIHuWW5ΔCH2 was performed as described herein. Clone #24, which expressed the highest concentration of IgG, 2 µg/ml as determined by a sandwich ELISA, was chosen for expansion and collection of supernatants. Before purification of MAb-WW6, supernatants from three 150 cm² flasks were pooled. Purification of MAb-WW6 was performed as described herein. The concentration of purified MAb-WW6 was 3.0 mg/ml as determined by ELISA. Then 10 µl aliquots of purified MAb-WW6 were placed in 0.5 ml tubes and stored frozen at −20° C. or below until use.

h. Expression and Purification of MAb-WW7

The stable transfection of mouse myeloma NS0 cells with expression vectors pLNCXIIHuCC49HuKV5 and pLgpCXIIHuWW5V8ΔCH2 was performed as described herein. Clone #14, which expressed the highest concentration of IgG, 8 µg/ml as determined by a sandwich ELISA, was chosen for expansion and collection of supernatants. Before purification of MAb-WW7, supernatants from three 150 cm² flasks were pooled. Purification of MAb-WW7 was performed as described herein. The concentration of purified MAb-WW7 was 2.0 mg/ml as determined by ELISA. Then 10 µl aliquots of purified MAb-WW7 were placed in 0.5 ml tubes and stored frozen at −20° C. or below until use.

6. Characterazation of MAb-chCC49-6P, MAb-WW1, MAb-WW2, MAb-WW3, MAb-WW4, MAb-WW5, MAb-WW6 and MAb-WW7, and 32P Labeled MAbs The purified modified MAbs were analyzed by SDS polyacrylamide gel electrophoresis (SDS-PAGE). In the presence of mercaptoethanol, two bands, one of 50 kDa (in the case of MAb-chCC49-6P, MAb-WW1, -WW2, -WW3, -WW4 and -WW5), or 40 kDa (in the case of MAb-WW6 and MAb-WW7) and the other of 25 kDa were seen on the Coomassie brilliant-blue stained gel (FIGS. 27A–H). These bands corresponded to the heavy chain and the light chain of the modified MAbs, respectively. The modified MAbs, MAb-chCC49-6P, MAb-WW1, -WW2, -WW3, -WW4, -WW5, -WW6 and -WW7, were phosphorylated by the cAMP-dependent protein kinase with [γ-$^{32}$P]ATP to specific radioactivities of 11126 Ci/mmol, 49 Ci/mmol, 35 Ci/mmol, 30 Ci/mmol, 7 Ci/mmol, 2895 Ci/nmnol, 2380 Ci/mmol and 2837 Ci/mmol, respectively. After reduction with 2-mercaptoethanol followed by SDS-PAGE, it was seen that the [$^{32}$P]MAb-chCC49-6P, and [$^{32}$P]MAb-WW5, [$^{32}$P]MAb-WW6 [$^{32}$P]MAb-WW7 migrated as strong single bands at either 50 kDa, or 25 kDa shown by autoradiography, corresponding to the positions of the heavy chains of the MAbs on a Coomassie blue stained gel. However, the MAb-WW1, -WW2, -WW3 and -WW4 were barely labeled when compared to MAb-chCC49-6P, -WW5, -WW6 and -WW7. This confirmed our prediction in Section A.3 (Results, page 96) that the specific radioacitivities of MAb-chCC49-6P, -WW5, -WW6 and -WW7 phosphorylated by PKA would be much higher than those of the other mutant MAbs because of the fewer potential conformations available for the serine or threonine of their protein kinase recognition sites. Furthermore, it can be seen on the autoradiographs that were overexposed for MAb-WW1, -WW2, -WW3 and -WW4 that the major band labeled was PKA, not the MAb.

7. Determination of Immunoreactivities of [32P]MAb-chCC49-6P, [32P]MAb-WW5, [32P]MAb-WW6 and [32P]MAb-WW7 a. Determination of Immunoreactivity of [32P]MAb-chCC49-6P

The immunoreactivity of [$^{32}$P]MAb-chCC49-6P was determined by direct binding assay (Table 2). The binding result using BSM-coated plates for [$^{32}$P]MAb-chCC49-6P was 66%. The nonspecific binding measured with the plates coated with PSM was less than 1%. The binding result using BSM-coated beads for [$^{32}$P]MAb-chCC49-6P was 95%. The nonspecific binding measured with the beads coated with PSM was 4%.

b. Determination of Immunoreactivity of [32P]MAb-WW5

The binding result using BSM-coated plates for [$^{32}$P] MAb-WW5 was 68% (Table 2). The nonspecific binding measured with the plates coated with PSM was less than 1%. The binding result using BSM-coated beads for [$^{32}$P]MAb-WW5 was 94%. The nonspecific binding measured with the beads coated with PSM was 4%.

c. Determination of Immunoreactivity of [32P]MAb-WW6

The immunoreactivity of [$^{32}$P]Mb-WW6 was determined by direct binding assay (Table 2). The binding result using BSM-coated plates for [$^{32}$P]MAb-WW6 was 68%. The nonspecific binding measured with the plates coated with PSM was less than 1%. The binding result using BSM-coated beads for [$^{32}$P]MAb-WW6 was 95%. The nonspecific binding measured with the beads coated with PSM was 3%.

d. Determination of Immunoreactivity of [32P]MAb-WW7

The immunoreactivity of [$^{32}$P]MAb-WW7 was determined by direct binding assay (Table 2). The binding result using BSM-coated plates for [$^{32}$P]MAb-WW7 was 68%. The nonspecific binding measured with the plates coated with PSM was less than 1%. The binding result using BSM-coated beads for [$^{32}$P]MAb-WW7 was 95%. The nonspecific binding measured with the beads coated with PSM was 2%.

8. Determination of Stabilities of [$^{32}$P]MAb-chCC49-6P, [$^{32}$P]MAb-WW5, [$^{32}$P]MAb-WW6 and [$^{32}$P]Mb-WW7 in Sera Stabilities of [$^{32}$P]MAb-chCC49-6P, [$^{32}$P]MAb-WW5, [$^{32}$P]MAb-WW6 and [$^{32}$P]MAb-WW7 in sera were determined. The stabilities of other mutant MAbs (MAb-WW1, -WW2, -WW3 and -WW4) could not be determined since none of these MAbs could be phosphorylated to high specificity. The consequence of this poor phosphorylation of the MAbs was that PKA in the phosphorylation assays got radiolabeled substantially (FIGS. 27B–E) so stability assays of these reactions reflected mostly the stability of the labeled PKA.

a. Determination of Stability of [32P]MAb-chCC49-6P in Sera

Figure 28:
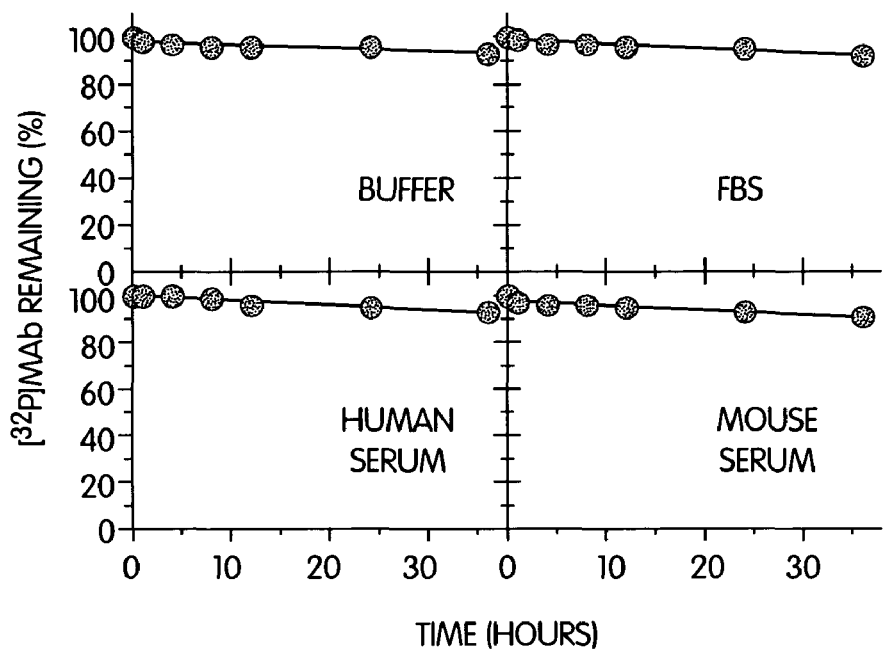
FIG. 28 depicts the stability of [$^{32}$P]MAb-chCC49-6P in various sera over a 24-hour period. The percentage of $_{32}$P remaining on the [$^{32}$P]MAb-chCC49-6P in sera and buffer over a 24-hour period at 37° C. is shown.

The percentage of [$^{32}$P]phosphate remaining on the [$^{32}$P]MAb-chCC49-6P was determined by comparing the radioactivity at different time points to that of the initial value in buffer and various sera (Table 3 and FIG. 28). It can be seen that about 91–93% of the phosphate remained stably attached to the MAb after 24-hour incubation in buffer, fetal bovine, human and mouse serum.

b. Determination of Stability of [32P]MAb-WW5 in Sera

Figure 29:
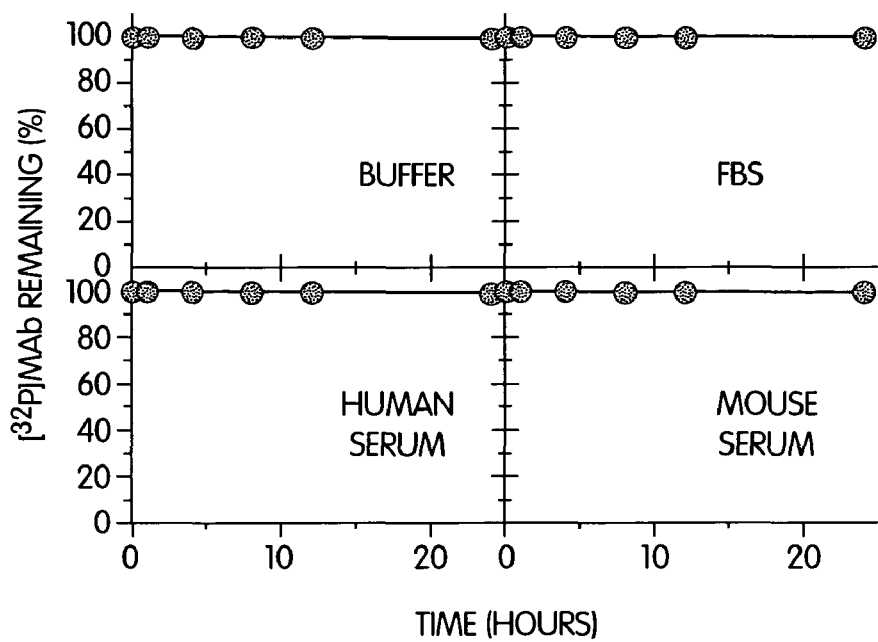
FIG. 29 depicts the stability of [$^{32}$P]MAb-WW5 in various sera over a 24-hour period. The percentage of $^{32}$P remaining on the [$^{32}$P]MAb-WW5 in sera and buffer over a 24-hour period at 37° C. is shown.
Figure 30:
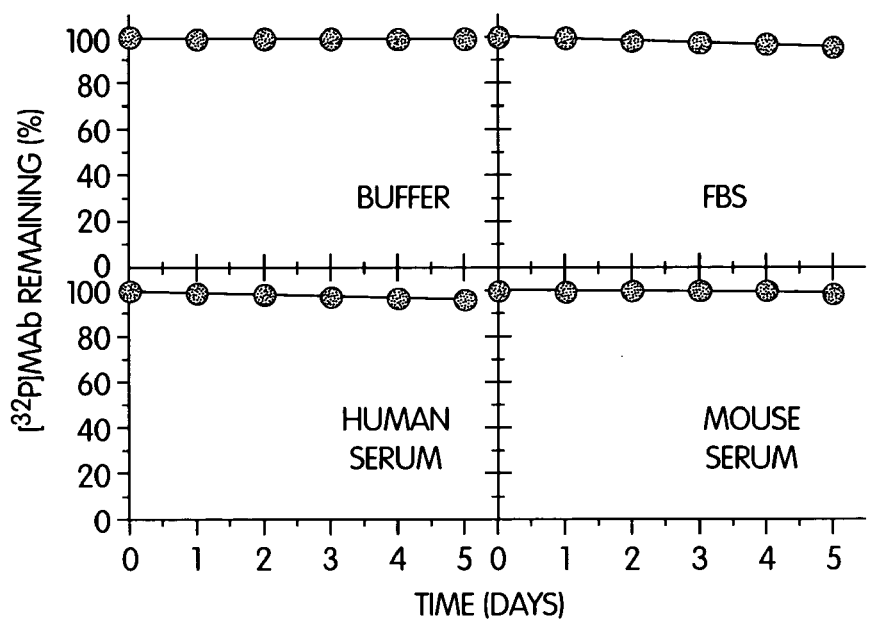
FIG. 30 depicts the stability of [$^{32}$P]MAb-WW5 in various sera over a 5-day period . The percentage of $^{32}$P remaining on the [$^{32}$P]MAb-WW5 in sera and buffer over a 5-day period at 37° C. is shown.
Figure 31:
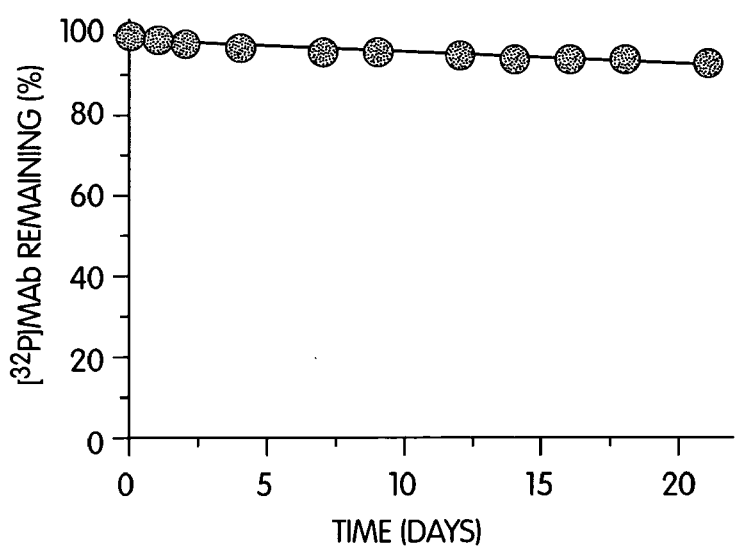
FIG. 31 depicts the stability of [$^{32}$P]MAb-WW5 in buffer over a 21-day period. The percentage of $^{32}$P remaining on the [$^{32}$P]MAb-WW5 in buffer over a 21-day period at 37° C. is shown.

The percentages of $^{32}$P radioactivity remaining on the MAb at different time points were determined by comparing it with that of the initial values of the [$^{32}$P]MAb. It showed that after 24 hr incubation in buffer, fetal bovine, human and mouse serum, at least 99% of the phosphate remained stably attached to the MAbs (Table 4, FIG. 29). Even after a five-day incubation in the above buffer and sera, more than 95% of the radioactivity remained attached to the MAb (Table 4, FIG. 30). We also measured a 21-day incubation of [$^{32}$P]MAb-WW5 in the buffer. More than 93% of the radioactivity remained attached to the MAb after 21 days at 37° C. (Table 5, FIG. 31).

This was consistent with our prediction in Section A.3 (Results, page 96) that the stabilities of the phosphates on MAb-WW5 would be greater than those on MAb-chCC49K1, MAb-CC49CKI, MAb-CC49CKII, MAb-CC49Tyr and MAb-chCC49-6P.

c. Determination of Stability of [32P]MAb-WW6 in Sera

Figure 32:
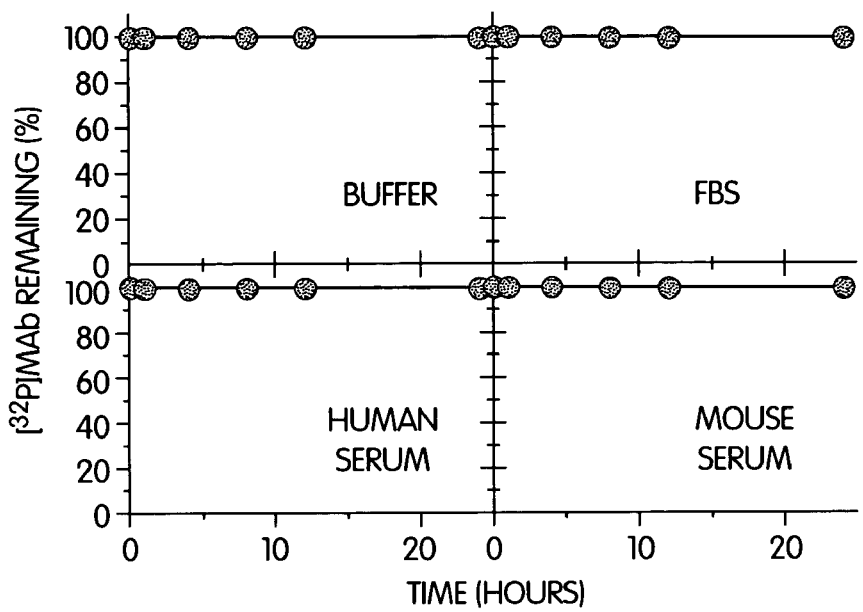
FIG. 32 depicts the stability of [$^{32}$P]MAb-WW6 in various sera over a 24-hour period. The percentage of $^{32}$P remaining on the [$^{32}$P]MAb-WW6 in sera and buffer over a 24-hour period at 37° C. is shown.
Figure 33:
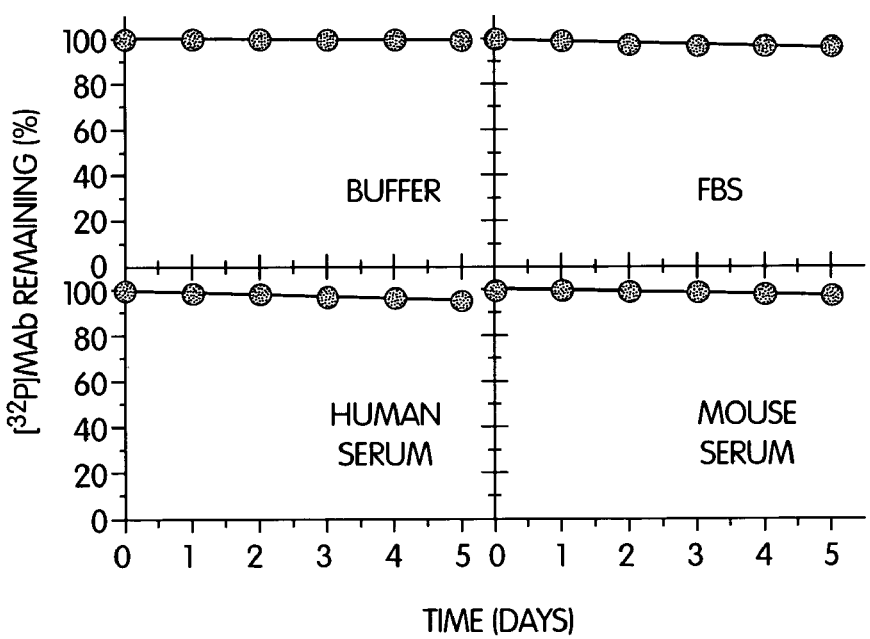
FIG. 33 depicts the stability of [$^{32}$P]MAb-WW6 in various sera over a 5-day period. The percentage of $^{32}$P remaining on the [$^{32}$P]MAb-WW6 in sera and buffer over a 5-day period at 37° C. is shown.
Figure 34:
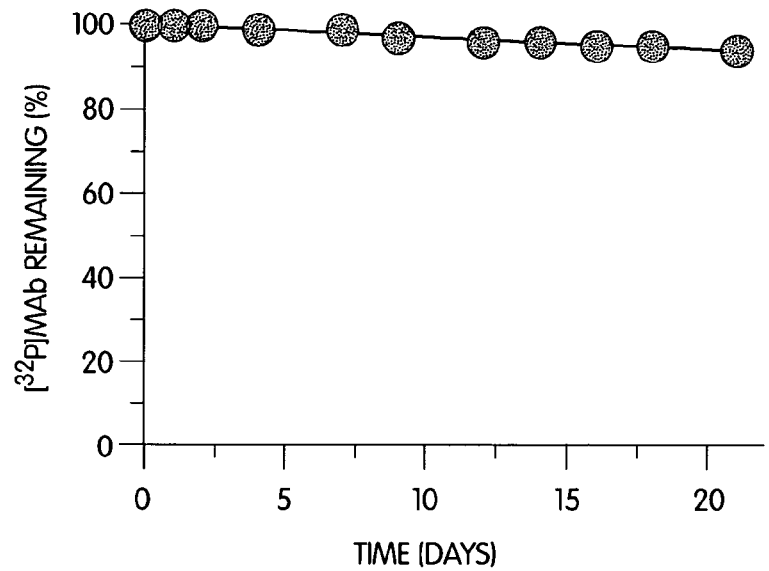
FIG. 34 depicts the stability of [$^{32}$P]MAb-WW6 in buffer over a 21-day period. The percentage of $^{32}$P remaining on the [$^{32}$P]MAb-WW6 in buffer over a 21-day period at 37° C. is shown.

The percentages of $^{32}$p radioactivity remaining on the MAb at different time points were determined by comparing it with that of the initial values of the [$^{32}$P]MAb. It showed that after 24 hr incubation in buffer, fetal bovine, human and mouse serum, at least 99% of the phosphate remained stably attached to the MAbs (Table 6, FIG. 32). Even after a five-day incubation in the above buffer and sera, more than 95% of the radioactivity remained attached to the MAb (Table 6, FIG. 33). We also measured a 21-day incubation of [$^{32}$ P]MAb-WW6 in the buffer. More than 94% of the radioactivity remained attached to the MAb after 21 days at 37° C. (Table 5, FIG. 34).

d. Determination of Stability of [32P]MAb-WW7 in Sera

Figure 35:
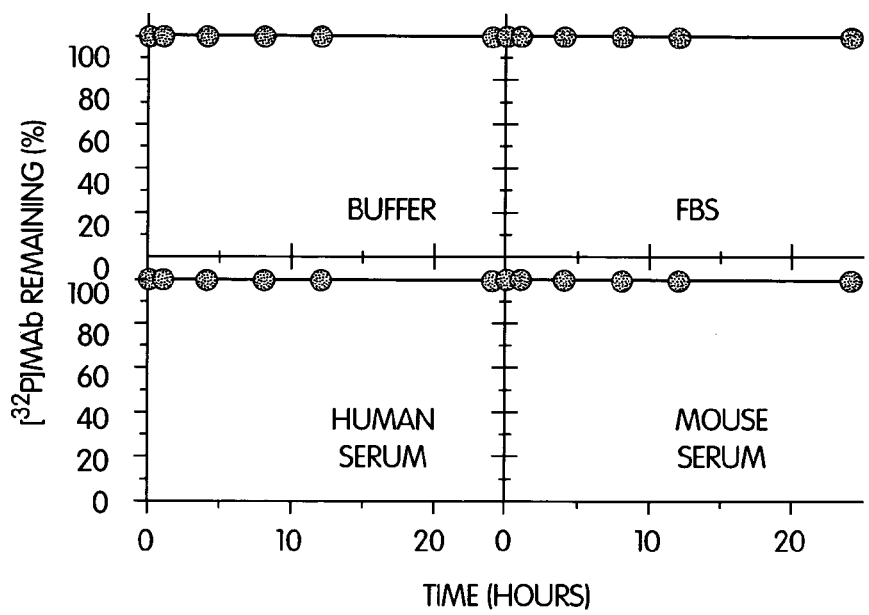
FIG. 35 depcuts the stability of [$^{32}$P]MAb-WW7 in various sera over a 24-hour period. The percentage of $^{32}$p remaining on the [$^{32}$P]MAb-WW7 in sera and buffer over a 24-hour period at 37° C. is shown.
Figure 36:
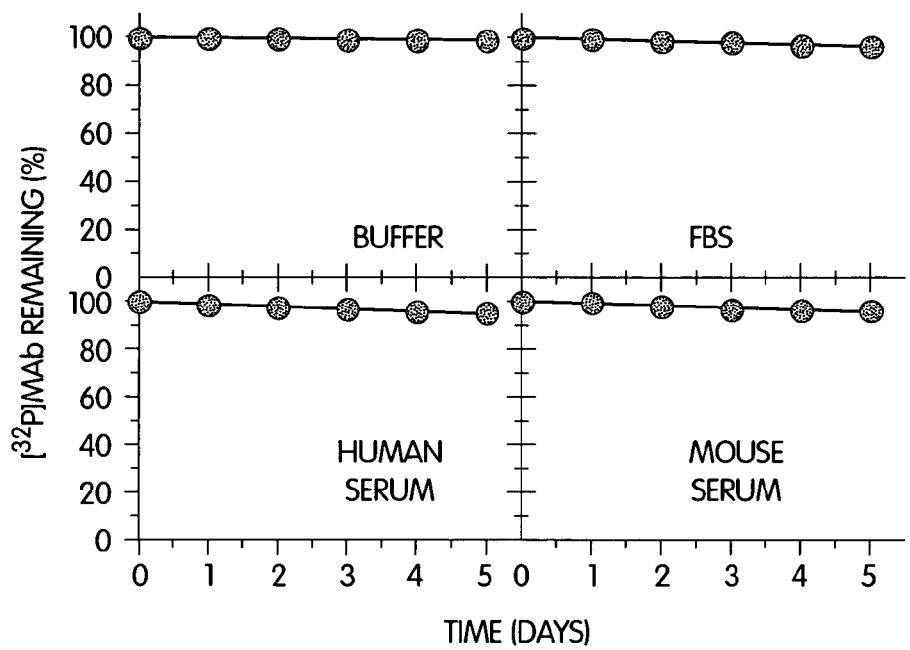
FIG. 36 depicts the stability of [$^{32}$P]MAb-WW7 in various sera over a 5-day period. The percentage of 32p remaining on the [$^{32}$P]MAb-WW7 in sera and buffer over a 5-day period at 37° C. is shown.
Figure 37:
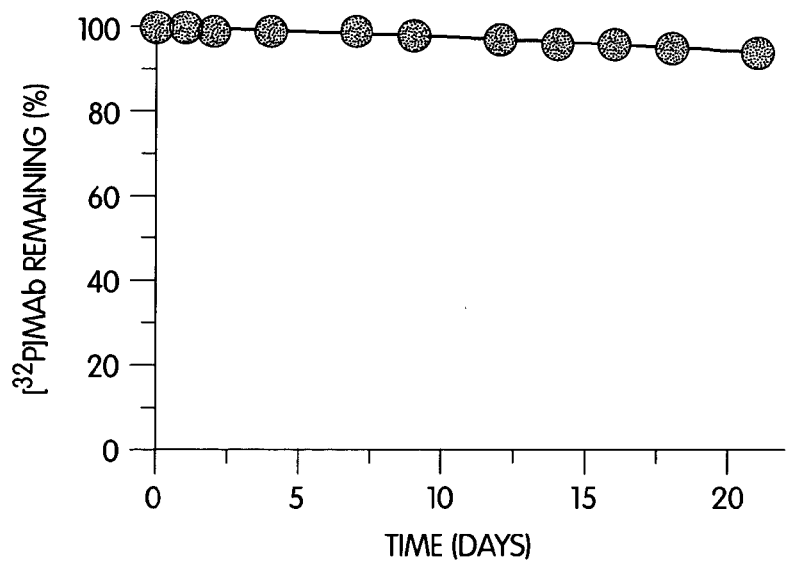
FIG. 37 depicts the stability of [$^{32}$P]MAb-WW7 in buffer over a 21-day period. The percentage of $^{32}$P remaining on the [$^{32}$P]MAb-WW7 in buffer over a 21-day period at 37° C. is shown.

The percentages of $^{32}$P radioactivity remaining on the MAb at different time points were determined by comparing it with that of the initial values of the [$^{32}$P]MAb. It showed that after 24 hr incubation in buffer, fetal bovine, human and mouse serum, at least 99% of the phosphate remained stably attached to the MAbs (Table 7, FIG. 35). Even after a five-day incubation in the above buffer and sera, more than 95% of the radioactivity remained attached to the MAb (Table 7, FIG. 36). We also measured a 21-day incubation of [$^{32}$P]MAb-WW7 in the buffer. More than 93% of the radioactivity remained attached to the MAb after 21 days at 37° C. (Table 5, FIG. 37).

III. Disscussion

Design and Construction of Phosphorylatable Monoclonal Antibodies with Highly Stable Phosphates with the Aid of Molecular Modeling Although $^{32}$P has been considered a useful radioisotope for radioimmunotherapy with several ideal characteristics, its utilization for labeling of MAbs was limited because there were no simple labeling procedures applicable. However, this problem has been overcome, and a labeling procedure which proved to be simple, efficient and applicable to virtually any protein has been developed. The phosphorylatable MAbs (MAb-chB72.3-P, MAb-chCC49K1, MAb-chCC49CKI, MAb-chCC49CKII and MAb-chCC49Tyr) were created by inserting the predicted consensus sequences for phosphorylation by the cAMP-dependent protein kinase and other protein kinases at the carboxyl terminus of the heavy chain constant region of MAb-chB72.3-P or MAb-chCC49. These MAbs were purified and could be phosphorylated by the appropriate protein kinase with [γ-$^{32}$P]ATP to high specific activity. These [$^{32}$P]MAbs bound to cells expressing TAG-72 antigens with high specificity.

However, it was found that in the first generation of phosphorylatable antibodies, the attached $^{32}$P was not sufficiently stable in buffer or serum to be useful for in vivo application in animals and humans. Several methods were suggested to improve the stabilities of the phosphorylatable MAbs. Since RRX(S/T) is a PKA recognition site, it was believed that by changing the amino acid residue X or the amino acid residues downstream of this site, the stability of the phosphorylatable MAbs could be changed. It was also believed that using threonine, instead of serine, in the PKA recognition site could increase the stability of the phosphorylatable Mabs, although this would compromise the efficiency of the phosphorylation dramatically. Alternatively, the stability of the phosphorylatable MAbs might also be changed if other phosphorylation enzymes were used. In this thesis, molecular modeling is used to locate phosphorylation sites in MAb-chCC49 that would be more resistant to hydrolysis. Because molecular modeling is a powerful tool for the prediction of the three dimensional structure of proteins, it was applied to make precise predictions to optimize the choice of the position of the protein kinase recognition site and improve the stability of the attached phosphates.

1. Design of Phosphorylatable Monoclonal Antibodies with Highly Stable Phosphates with the Aid of Molecular Modeling a. Choice of Site for Introduction into MAb-chCC49

The sites for introduction of the cAMP-dependent protein kinase recognition sites were chosen using following criteria: (1) Since the consensus sequence for cAMP-dependent protein kinase is Arg-Arg-X-Ser/Thr, the sites with a maximum number of these four residues were investigated and chosen so that minimal modification of the original MAb structure would occur. (2) The sites in the complementarity-determining regions (CDR) were avoided. The CDR region on MAb-chCC49 is defined. This region is the portion of the MAb variable domain which binds to antigen, so any modification of these sites might change the binding affinity or specificity of the MAb. (3) The site would be accessible to the protein kinase. This was accomplished by visual analysis of the 3D molecular structure of MAb-chCC49.

By following the first criterium, twelve sites in the whole MAb-chCC49 molecule were found for introduction of PKA site. Evaluation of 3D models of these putative mutant Abs and model of MAb-chCC49 suggested that not all these sites were good for site-directed mutagenesis (Table 8) (SEQ ID NOs 47–70). First, analysis of the MAb-chCC49 model revealed that four out of twelve potential sites (site 5, 6, 8, 9) were buried. Furthermore, it was showed by molecular modeling that introduction of arginine residues into these sites would cause severe steric problems in the structure of the MAb-chCC49 molecule (Table 8). These sites, therefore, were excluded for further consideration. The rest of the sites were examined to see if the mutations of the sites would change the CDR regions of MAb-chCC49 as described. Site 11 was excluded since all four amino acid residues in the PKA recognition site are in the CDR2 region of the light chains of MAb-chCC49. Mutations of some amino acid residues (e.g. Cys320 in site 6, and Pro117 in site 12) were also avoided since these residues might play critical roles in maintaining proper structure of the MAb. Those possible mutants, which did not show the obvious problems of the above kinds, were eventually chosen (three sites on the heavy chain and one site on the light chain) for the further work.

b. Choice of Template for Modeling MAb-chCC49

Before MAb-chCC49 was modeled, questions arose as to which structure could be used as template. Although the structures of intact MAbs have been a subject of great interest for many years, due to the intrinsic mobility and segmental flexibility of antibodies, it is extremely difficult to get the crystal structure of an intact antibody. So far crystal structures of only two intact MAbs have been solved. One is MAb231, a mouse IgG2a MAb against canine lymphoma cells. While the other is MAb61.1.3, a murine IgG1 MAb against phenobarbital. Since one site chosen to introduce mutations was in the hinge region of the MAb, it was decided to use the crystal structure of the intact MAb as template. Evaluation of the crystal structures of these two intact MAbs revealed the relative position of the Fab, hinge and Fc regions. In addition, both showed an overall asymmetry, which might manifest a considerable degree of intrinsic mobility and segmental flexibility of the antibodies. Other structural features of the two MAbs though, were quite different. The IgG1 has a distorted yet compact Y shape, whereas IgG2a has a more extended T shape. This difference may well reflect different amino acid residues in their hinge regions. The hinge of IgG2a which has 23 amino acids is longer than that of IgG1 by six amino acids, three in the upper hinge region and three in the lower hinge region. The overall sequence comparisons performed with the Bestfit Program in the GCG package (Wisconsin Package Version 10, Genetics Computer Group (GCG), Madison, Wis.) indicated that IgG1 shares a little more sequence homology with MAb-chCC49 than does IgG2a. The results demonstrated that the light chain sequences of MAb61.1.3 (IgG1) and MAb-chCC49 share 65% identity and 72% similarity, whereas that of MAb231 (IgG2a) and MAb-chCC49 share 63% identity and 70% similarity; and that the heavy chain sequences of IgG1 and MAb-chCC49 show 64% identity and 74% similarity, whereas IgG2a and MAb-chCC49 show 60% identity and 68% similarity. However, when sequences of the hinge regions were used to do the comparison, it was found that the hinge of MAb-chCC49 resembles more that of MAb231 in terms of both length and amino acid sequence than that of MAb61.1.3 (FIG. 38). Like MAb231, MAb-chCC49 also has a long hinge, only one amino acid less than that of MAb231, suggesting that it might take on a similar extended structure as MAb231. MAb231 and MAb-chCC49 also share substantial sequence identity (about 90%), in both core and lower hinge regions. On the other hand, MAb-chCC49 and MAb61.1.3 do not resemble each other in this region. Compared to MAb-chCC49, MAb61.1.3 has a much shorter hinge. Sequence alignment also showed that they have relatively very low homology in this region. Since two of the mutant MAbs would have a phosphorylation site in the hinge region, it was decided to continue to use MAb231 as template to model the entire MAb-chCC49 molecule.

c. Molecular Modeling Protocol

A protocol was developed to build the models of the modified MAbs. Since the phosphate group is a large group, structural distortion may result from its attachment to serine or threonine residues of the MAb. To verify this possibility, the phosphate groups were attached to the serine or threonine residues at the PKA recognition sites of the MAb after the models of the mutant Mabs were built. In addition, systematic conformational searches were conducted to analyze all possible conformations the MAb would adopt after the attachment of the phosphate groups. The results showed that introduction of phosphate groups would not change the structures of the mutant MAbs significantly.

2. Construction of Phosphorylatable Monoclonal Antibodies with Highly Stable Phosphates a. In vitro Work Since the goal was to make stable radiolabeled MAbs for in vivo utilization, the stability profiles of the phosphorylatable Mabs was examined. Some of the modified MAbs (MAb-WW5, MAb-WW6, and MAb-WW7) showed superior stability in all the sera and the buffer tested. Compared to [$^{32}$P]MAb-chCC49K1 and [$^{32}$P]MAb-chCC49-6P, where about 93%–96% of the phosphates remained stably attached to the MAbs after 24 hours incubation in buffer and different sera, the stabilities of the phosphate of [$^{32}$P]MAb-WW5, [$^{32}$P]MAb-WW6 and [$^{32}$P]MAb-WW7 showed significant improvement (FIG. 39). After 24-hour incubation in the same buffer or sera as [$^{32}$P]MAb-chCC49K1 and [$^{32}$P]MAb-chCC49-6P, more than 99% of the phosphates remained stably attached to MAb-WW5, MAb-WW6 and MAb-WW7 whereas there was significant hydrolysis of the phosphate from [$^{32}$P]MAb-chCC49K1 where the protein kinase recognition site was fused to the C-terminus. Even after a 21-day incubation in buffer or sera, there was still more than 93% of the radioactivity attached to the MAbs. Thus, the phosphoserine (Ser224) in these new constructs is highly resistant to hydrolysis.

b. In vivo Work

Figure 40:
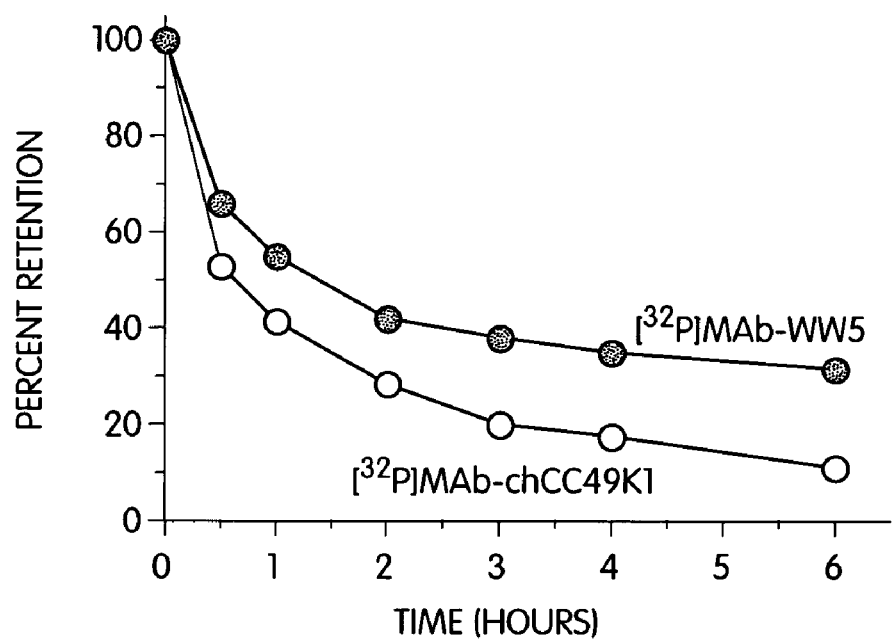
FIG. 40 is a comparison of plasma clearance of [$^{32}$P]MAb-WW5 and [$^{32}$P]MAb-chCC49K1 in mice. The plasma clearance was performed by collecting 10 μl of blood (by tail bleed) at various timepoints. The values are normalized to the bleed taken at about 2–5 minutes after the injection.

The in vivo studies, plasma clearance (FIG. 40) and biodistribution (Table 9), of both [$^{32}$P]MAb-WW5 and [$^{32}$P]MAb-chCC49K1 were performed. As seen from FIG. 38, more than 90% of [$^{32}$P]MAb-chCC49K1 was cleared from blood by six hours, however only about 70% of [$^{32}$P]MAb-WW5 was cleared from the blood by the same time. This data demonstrated that [$^{32}$P]MAb-WW5 showed much more improved stability over [$^{32}$P]MAb-chCC49K1 in plasma clearance assay.

Compared to [$^{32}$P]MAb-chCC49K1, [$^{32}$P]MAb-WW5 also showed much improved tumor localization. At all time points, [$^{32}$P]Mab-WW5 accumulated in significantly higher amount in tumor than those in all the other organs. The amount of [$^{32}$P]MAb-chCC49K1 accumulated in tumor was no significantly higher than those in other organs. [$^{32}$P]MAb-WW5 even showed comparable, if not better, tumor localization than [$^{125}$I]MAb-chCC49 and [$^{131}$I]MAb-chCC49, which has already undergone a phase II clinical trial in patients with breast cancer. It can be seen in Table 8 that at 24 hour time point, about two times of [$^{125}$I]MAb-chCC49 and [$^{131}$I]MAb-chCC49 were accumulated in spleen than in tumor, however, for [$^{32}$P]MAb-WW5, the ratio was the opposite.

These in vivo studies demonstrated that MAb-WW5 has great potential to be used in diagnosis and therapy of adenocarcinomas.

3. Hypotheses of the relationship between the models, stabilities of the phosphates on the MAbs and phosphorylation efficiencies of the phosphorylation sites.

After generating the models of the phosphorylatable MAbs with and without attached phosphates, two interesting phenomena were observed. First, the attached phosphates on some constructs (MAb-chCC49K1, MAb-CC49CKI, MAb-CC49CKII, MAb-CC49Tyr, MAb-chCC49-6P, MAb-WW5, MAb-WW6 and MAb-WW7) had much more allowed conformations than those on some other mutant MAbs (MAb- WW1, -WW2, -WW3 and -WW4). Thus, it was hypothesized that the greater the number of allowed conformations, the easier accessibility of the enzymes to the recognition site, the more efficient the phosphorylation of the MAb. According to this hypothesis, it was predicted that MAb-chCC49-6P, MAb-WW5, -WW6 and -WW7 would be radiolabeled by PKA to much higher specific activities than the other mutant MAbs (MAb-WW1, -WW2, -WW3 and -WW4). This prediction was confirmed by phosphorylation assays of the modified MAbs. The MAb-chCC49-6P, MAb-WW5, -WW6 and -WW7 were phosphorylated by PKA with [$\gamma$-$^{32}$P]ATP to specific radioactivities of 11,126 Ci/mmol, 2895 Ci/mmol, 2380 Ci/mmol and 2837 Ci/mmol, respectively. However, the mutant MAbs, MAb-WW1, -WW2, -WW3 and -WW4, were barely phosphorylated by PKA to specific radioactivities less than 49 Ci/mmol, 35 Ci/mmol, 30 Ci/mmol and 7 Ci/mmol, respectively.

Second, the phosphates on the modified MAbs constructed had different potentials to form hydrogen bonds with the neighboring amino acid residues. On some constructs (MAb-WW2, -WW3, -WW5, -WW6 and -WW7) (Table 1), all of the attached phosphates could form hydrogen bonds with the surrounding amino acid residues. However on the other constructs, none or only some of the attached phosphates could form hydrogen bonds, the others could not (MAb-WW1, MAb-WW4, MAb-chCC49K1, MAb-CC49CKI, MAb-CC49CKII, MAb-CC49Tyr and MAb-chCC49-6P). Since formation of hydrogen bonds physically defines where surrounding residues can ineract with the phosphate moiety, it was hypothesized that hydrogen bonds could serve as surrogate markers for regions where the phosphate could be protected from hydrolysis. The hydrogen bond itself, other factors being identical, should make the phosphate residue more susceptible to hydrolysis. However, as a surrogate marker for protected regions, the greater the potential for hydrogen bond formation, the greater the resistance of the phosphate to hydrolysis. That is, the stability of the attached phosphate is enhanced if the phosphate is protected by surrounding residues from attack by hydroxyl groups by charge interactions or by a hydrophobic environment, for example. According to this hypothesis, the stabilities of the phosphates on MAb-WW2, -WW3, -WW5, -WW6 and -WW7 would be greater than those on MAb-WW1, MAb-WW4, MAb-chCC49K1, MAb-CC49CKI, MAb-CC49CKII, MAb-CC49Tyr and MAb-chCC49-6P. This prediction was confirmed by comparing the stabilities of phosphorylated MAb-WW5, -WW6 and -WW7 with those of MAb-chCC49K1, MAb-CC49CKI, MAb-CC49CKII, MAb-CC49Tyr and MAb-chCC49-6P. [$^{32}$P]MAb-WW5, [$^{32}$P]MAb-WW6 and [$^{32}$P]MAb-WW7 were very stable in all the sera and the buffer tested.

The hypothesis could not be tested with other phosphorylated mutant MAbs (MAb-WW1, -WW2, -WW3 and -WW4), since none of these MAbs could be phosphorylated significantly. In these cases, there was low phosphorylation of the MAbs but PKA became radiolabeled substantially.

Figure 41:
FIG. 41 depicts the crystal structure of the catalytic subunit of the cAMP-dependent protein kinase from Bos Taurus with its inhibitor. The catalytic subunit of the PKA is shown in cyan, while its inhibitor is in magenta. Thr197 and Ser338 are shown in white. The green regions that represent the phosphates attached to the serine or threonine residues are also shown. The oxygens attached to the phosphates are in red.
Figure 42:
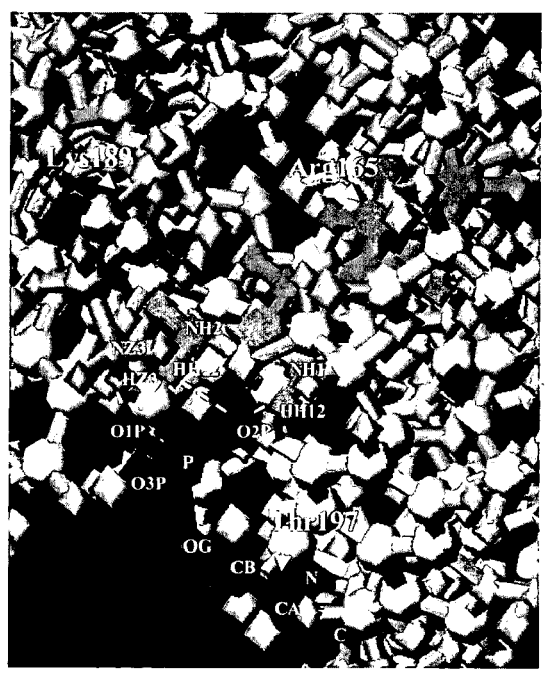
FIG. 42 depicts the stabilization of phosphate moiety on threonine 197 in the catalytic subunit of the cAMP-dependent protein kinase from Bos Taurus. The threonine carbons are: C, main chain carbonyl carbon; CA, alpha carbon; CB, beta carbon to which the phosphate (P) is attached through the serine oxygen (OG). Other symbols are: O1P, first oxygen of phosphate; O2P, second oxygen on phosphate; O3P, third oxygen of the phosphate; NZ3, nitrogen on the side chain of Lys189. HZ3, hydrogen in hydrogen bonds from side chain nitrogen (NZ3) of Lys189 to O1P of Thr197. NH1, first nitrogen on the side chain of Arg165. HH12, hydrogen in hydrogen bonds from side chain nitrogen (NH1) of Arg165 to O2P of Thr197. NH2, second nitrogen on the side chain of Arg165. HH22, hydrogen in hydrogen bonds from side chain nitrogen (NH2) of Arg165 to both O1P and O2P of Thr197.
Figure 43:
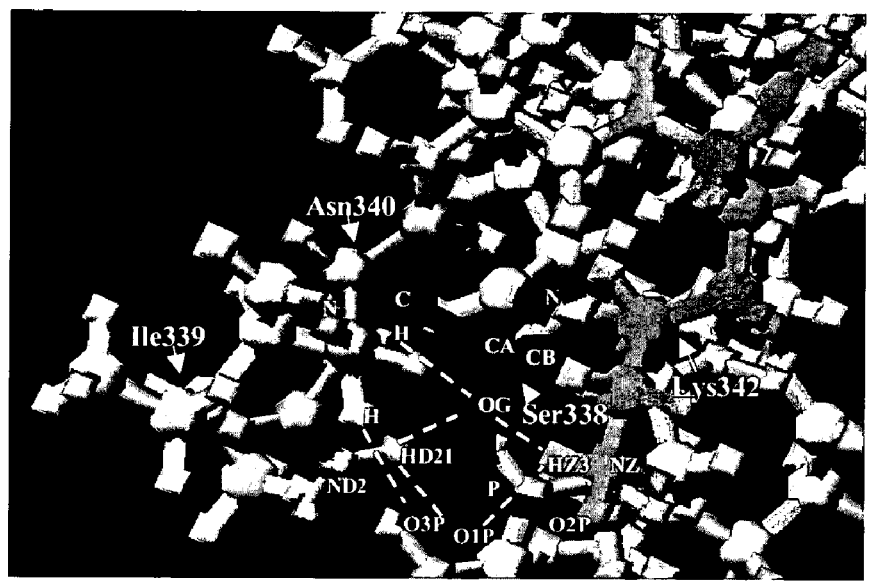
FIG. 43 depicts the stabilization of phosphate moiety on serine 338 in the catalytic subunit of the cAMP-dependent protein kinase from Bos Taurus. The side chain of Ser338 stabilized the phosphate moiety through hydrogen bondings between O1P and side chain nitrogens on both Asn189 and Lys342, and also between O3P and main chain nitrogen on Ile339. In addition the side chain OG of Ser338 could also form hydrogen bonds with both main chain nitrogen and the first side chain nitrogen on Asn340, and with third side chain nitrogen on Lys342. Other labels are the same as those in the legend to FIG. 42.

Another line of evidence that supports the hypothesis was the study of the structure of PKA. PKA has endogenous phosphates attached to Thr197 and Ser338 of the enzyme (FIG. 41). The phosphates on Thr197 and Ser338 form six and four hydrogen bonds, respectively (FIG. 42 and FIG. 43). Both Thr197 and Ser338 containing the recognition motifs RTWT and RVS, respectively, are not readily phosphorylated. The phosphates are highly stable because they remain attached after extensive purification of the protein and during the entire crystallization process. Such a phosphate recognition site internal to the protein would not be convenient for labeling a MAb efficiently. Thus, for labeling Mabs, a site has been judicially sought that is readily accessible to the enzyme, but still has sufficient opportunity for hydrogen bonding to be in a protected region. Alternatively, if a protein could be unfolded, then phosphorylated and refolded efficiently, this could be a useful strategy. However, this would not be practical for MAbs or other proteins. The data describing the stability of the phosphates on Thr197 and Ser338 together with our data describing the stability of the phosphates on MAb-WW5, -WW6 and -WW7 supports the hypothesis that hydrogen bond interaction of the phosphates with the surrounding amino acids defines regions of protection that contribute to the stabilities of the attached phosphates on the proteins.

4. Summary

The results demonstrate that molecular modeling can be used effectively to design phosphorylation sites with optimal characteristics to enable excellent phosphorylation and to minimize hydrolysis of the phosphate. Such monoclonal antibodies should prove to be very useful in diagnosis and therapy of cancer.

IV. Concluding Summary

Radiolabelled monoclononal antibodies against tumor-associated antigens (TAA) are used clinically for detection, staging and therapy of cancers. To develop more effective radiolabeled monoclonal antibodies, recognition sites were introduced for the cAMP-dependent protein kinase into MAb-chCC49 by site-directed mutagenesis of the coding sequence. Molecular modeling was used to locate appropriate regions for introduction of the cAMP-dependent phosphorylation sites, to construct variants of MAb-chCC49 without changing their immunoreactivity or biological properties, and to define sites where the attached phosphates would be particularly stable and the phosphorylation site would be accessible to the enzyme. Four sites on the heavy chain and one on the light chain were chosen. Vectors expressing the mutant MAbs were constructed and transfected into mouse myeloma NS0 cells that expressed a high level of the resultant mutant MAbs. Some of the mutant MAbs, MAb-WW5, MAb-WW6 and MAb-WW7, which contained the cAMP-dependent phosphorylation site at the hinge region of the heavy chain, can be phosphorylated by the catalytic subunit of cAMP-dependent protein kinase with [$\gamma$-$^{32}$P]ATP to high specific activity and retains the phosphate stably. Compared to MAb-chCC49K1, another phosphorylatable variant of MAb-chCC49, the phosphate attached to MAb-WW5, -WW6 and -WW7 showed much improved stability: about a ten-fold increase in resistance to hydrolysis. This was proved by both in vitro and in vivo studies. MAb-WW5, -WW6 and -WW7 exhibited high binding specificity to the TAG-72 antigen.

The models of the mutant monoclonal antibodies with or without attached phosphates demonstrated that the resistance of the phosphate to hydrolysis correlated with the potential for hydrogen bonding interaction of the phosphorylated serine or threonine sites. The more the potential for the hydrogen bond formation, the more stable was the phosphate on the phosphorylated monoclonal antibodies due to the environment surrounding the phosphate. In addition, the more conformations allowed for the attached phosphate groups on the MAb, the more accessible was the PKA recognition site to the enzyme, making radiolabeling of the MAb by the PKA more efficient. These general theses provide a foundation to construct phosphorylation sites on monoclonal antibodies and other proteins where the MAbs and proteins could be radiolabeled to high specific activity and the attached phosphates would be resistant to hydrolysis. Monoclonal antibodies with such sites labeled with [$^{32}$P]phosphate would be excellent candidates for therapy of various malignancies.

EXAMPLE 2

Example 2 is intended to compare the stabilities of phosphorylated monoclonal antibodies with engineered phosphorylated sites.

I. Materials and Methods

In the present study, the SYBYL molecular modeling package (version 6.5; Tripos Association, St. Louis, Mo., 1999) was used for structural analysis and geometry refinement. Most of the homology and mutant modeling was performed with the LOOK 3.5 program (Molecular Application Group, Palo Alto, Calif.). For the geometry optimization, Kollman united charges, molecular mechanics force field and the MAXIMIN2 minimizer of SYBYL were used. All these visualization analyses and simulations were performed on Silicon Graphics Octane workstations.

1. Template

The crystal structure of the intact MAb231, was used as template to model MAb-chCC49. These coordinates are now available from the Polypeptide Data Bank (PDB) as ID 1IGT. Because the crystal structure of MAb231 was previously the only one available for an intact antibody, MAb231 was used as the template for modeling in this study. In addition, after the crystal structure of MAb61.1.3 was reported, the length and sequence of the hinge region of MAb231 was noted as being more similar to the hinge region of MAb-chCC49 than that of MAb61.1.3. The resulting model of MAb-chCC49 was then used as template to model the MAb-chCC49 mutant.

2. Modeling MAb-chCC49

Overall procedure. The model of MAb-chCC49 was built with the homology modeling module of the LOOK3.5 program. After the coordinates of IgG2a MAb231 were obtained, the structure of MAb231 was used as template to develop a molecular model of MAb-chCC49. First of all, the four chains of MAb231 were separated individually and designated as L1, L2, H1, and H2 (L for light chain and H for heavy chain). The coordinates of each chain were extracted and saved separately. The strategy used to build a model of MAb-chCC49 was to do homology modeling on each chain of MAb-chCC49, separately. The 3-D structure of chain L1 of MAb231 was first displayed, then the sequence of the light chain of MAb-chCC49 was introduced into the program and the automatic alignment mode was set up to align the sequence of the MAb-chCC49 light chain with that of the sequence of MAb231 light chain. The model was built with the program module SEGMOD under the automated method with full refinement. The coordinates of chain L1 of MAb-chCC49 were thereafter generated and saved as a PDB file. The models and coordinates of chains L2, H1, and H2 of MAb-chCC49 were generated by the same procedure as described above.

Geometry refinement and energy minimization. Further geometry refinement and optimization was done with SYBYL molecular modeling software. The 3-D structure of chain L1 of MAb-chCC49, the coordinates of which were generated as described above, was displayed. Essential hydrogen atoms (hydrogen atoms attached to nitrogen, oxygen, and/or sulfur atoms that could potentially be involved in hydrogen binding with surrounding atoms/residues) were added. In the first step, the side chain was scanned to minimize conformational strains, if any, within side chain groups and surrounding residues. Proline is the only residue that contains a ring in its backbone and it adopts a phi angle close to 70. Therefore, the "fix-proline" command in SYBYL was used to maintain proline geometry. The orientations of the amide groups of Asn and Gln were scanned to favor potential hydrogen bonding with surrounding residues. Finally, the Kollman united charges were loaded on chain Li so that the electrostatic contribution in the energy calculation could be included. The 3-D structures of chain L2, H1, H2 were geometrically refined and optimized by the same procedure as used for chain L1. Then the refined models of chains L1, L2, H1, and H2 of MAb-chCC49 were merged into a single molecule. Afterwards, the side chains, as well as the amide groups of Asn and Gln, were fixed to relax the strain in the composite molecule.

Since MAb-chCC49 is a large polypeptide, the energy minimization step was broken into two parts. Before energy minimization of the whole molecule, the minimization of the side chains ws carried out first. The backbone was used by making it an aggregate set. Then energy minimization of the side chains was achieved with the Kollman united force field option for 100 iterations. In the next step, the aggregate was deleted, and energy minimization of the whole molecule was done by the Powell method in the SYBYL program.

3. Choice of Site for Introduction into MAb-chCC49

The site for introduction of the cAMP-dependent polypeptide kinase recognition site was chosen to have several properties. It would not be in the CDR region of the MAbs; introduction of the kinase recognition site would require no more than three amino acid changes; the site would be accessible to the polypeptide kinase. This was accomplished by the programs above as described in detail in "Results" section.

4. Modeling Mutant MAbs and Mutant [$^{32}$P]MAbs

This procedure was similar to modeling of MAb-chCC49. Briefly, each chain of the mutant MAb was homology modeled by using the corresponding chain of MAb-chCC49 as template. Geometry refinement and optimization, and energy minimization of the modeled mutant MAbs was carried out in the same way to obtain the refined model of MAb-chCC49.

After the model of the mutant MAb was obtained, a phosphate group was generated and attached to the hydroxyl group of Ser/Thr in the PKA recognition site by using 'builder' module of the SYBYL modeling package. For WW1, the phosphate group was attached to Ser 123; for WW2, to Thr 224; for WW3, to Ser 21; for WW4, to Thr 20. To obtain the optimal position and to generate favorable interaction with surrounding residues by the phosphate moiety, the systematic conformational search along C—C and C—C of Ser/Thr in the PKA recognition site was performed. The conformation of the Ser/Thr side chain in which phosphate moiety was stabilized through hydrogen bonding was chosen. Then minimization subset (only four amino acid residues in the PKA recognition site, RRXS/T were chosen) was done for 100 iterations by the Powell method.

5. Construction of Vectors for Expression of Mutant Polypeptides

The vector pdHL7-CC49K1 for expression of the phosphorylatable monoclonal antibody (MAb-chCC49K1) with two cAMP-kinase recognition sites on each heavy chain was modified as follows to construct site-specific mutations to introduce phosphorylation sites in various positions of MAb-CC49. To construct the expression vector for MAb-chCC49 without the phosphokinase recognition site, first of all, an intermediate vector pdHL7-BH was made so that one of two XhoI restriction sites in pdHL7-CC49K1 could be removed. To construct pdHL7-BH, the vector pdHL7-CC49K1 was digested with BamHI and HindIII restriction endonucleases. The resultant 6854 bp fragment was isolated by agarose gel electrophoresis, then purified, blunt-ended, and self-ligated to generate intermediate vector pdHL7-BH.

To construct pdHL7-CC49, a 358 bp fragment was amplified from pdHL7-CC49K1 by PCR with the 5' and 3' primers GTGACCGCTGTACCAACCTCTGTCC, SEQUENCE ID NO. 26 and CCCTCGAGTCA-CTTGCCCGGGGACAGG-GAGAGG, (SEQUENCE ID NO. 27) respectively. This PCR fragment was then digested with BsrGI and XhoI restriction endonucleases, and purified. The vector pdHL7-BH was digested with the same restriction endonucleases and a 6463 bp fragment was released, purified and ligated to the digested and purified 358 bp PCR fragment. The resultant plasmid pdHL7-CC49BH was then digested with XmaI and EcoRI restriction endonucleases, and yielded two bands. The smaller band, which was 2726 bp, was isolated and purified, then further ligated to the 6667 bp fragment which was isolated and purified after pdHL7-CC49K1 was digested with the same restriction endonucleases. The resultant construct pdHL7-CC49 was characterized by BsrGI and XhoI restriction endonuclease digestion and DNA sequencing.

To construct plasmid pWW1, the vector pdHL7-CC49 was digested with HindIII and PstI restriction endonucleases to isolate a 890 bp fragment. The fragment was isolated by agarose gel electrophoresis, then purified. The replicative form (RF) DNA of phage M13mp18 was digested with HindIII and PstI restriction endonucleases and the large DNA fragment isolated. The 890 bp fragment was then inserted into the HindIII and PstI site of the M13mp 18 DNA to yield plasmid pM 13-W21. Then site-directed mutagenesis was performed as described. Briefly, pM13-W21 was introduced into the *Escherichia coli* CJ236 strain, which is a dut, ung strain and lacks the enzyme uracil N-glycosylase which normally removes uracil from DNA. This results in incorporation of uridine in the DNA. Then single-stranded (SS)-DNA containing uridine from phage M13 -W21 was used as template for site-directed mutagenesis to prepare the mutant M13-WW1. The oligodeoxynucleotide m120, 5'-GCAGCCTCCACCAGGCGCCCATCGGTC-3', (SEQUENCE ID NO. 28) was used for site-directed mutagenesis. Oligonucleotide m120 contains a phosphokinase recognition site RRPS and also a NarI recognition site. Oligonucleotide m120 was annealed to uridine-containing SS-DNA of M13-WW21, followed by the in vitro synthesis of the complementary strand. Afterwards, the resultant double-stranded (DS) DNA was transformed into *E. coli* DH5F' strain with a functional uracil N-glycosylase to remove the parental strand. The desired mutant was characterized by NarI restriction endonuclease digestion and DNA sequencing. Thus we obtained the construct M13-WW1. Then RF-DNA of M13-WW1 was digested with HindIII and BstEII restriction endonucleases, and the resultant 410 bp fragment was inserted into the vector pCC49 that was digested with the same endonucleases to yield plasmid pWW1. The vector pWW1 expresses the MAb-WW1 with amino acid substitutions K120R and G121R in the MAb-CC49 heavy chain.

To construct plasmid pWW2, the vector pCC49 was digested with HindIII and NaeI restriction endonucleases to isolate a 1424 bp fragment. The fragment was isolated by agarose gel electrophoresis, then purified. The replicative form (RF) DNA of phage M13mp19 was first digested with XbaI restriction endonuclease, then blunt-ended by Klenow fragment of DNA polymerase. Afterwards, this DNA was further digested with HindIII restriction endonuclease, and the large DNA fragment was isolated. The 1424 bp fragment was then inserted into the XbaI blunt-ended and HindIII site of the M13mp19 DNA to yield phage M13-W22. Then site-directed mutagenesis was performed as described. Briefly, pM13-W22 was introduced into the *E. coli* CJ236 strain, which is a dut, ung strain and lacks the enzyme uracil N-glycosylase which normally removes uracil from DNA. This results in incorporation of uridine in the DNA. Then single-stranded (SS)-DNA containing uridine from phage M13-W22 was used as template for site-directed mutagenesis to prepare the mutant M13-WW2. The oligodeoxynucleotide m221rev, 5'-GGGCATGTGTGACGTCTGTCA-CAAGATTTG-3', (SEQUENCE ID NO. 29) was used for site-directed mutagenesis. Oligonucleotide m221rev contains a phosphokinase recognition site RRHT and also a AatII recognition site. Oligonucleotide m221rev was annealed to uridine-containing SS-DNA of M13-WW22, followed by the in vitro synthesis of the complementary strand. Afterwards, the resultant double-stranded (DS) DNA was transformed into *E. coli* DH5F' strain with a functional uracil N-glycosylase to remove the parental strand. The desired mutant was characterized by AatII restriction endonuclease digestion and DNA sequencing. Thus the construct M13-WW2 was obtained. Then RF-DNA of M13-WW2 was digested with SacII restriction endonuclease, and the resultant 410 bp fragment was inserted into the vector pCC49 that was digested with the same endonuclease to yield plasmid pWW2. The vector pWW2 expresses the MAb-WW2 with amino acid substitutions K221 R and T222R in the MAb-CC49 heavy chain.

To construct plasmid pWW3, the vector pCC49 was digested with HindIII and SnaBI restriction endonucleases to isolate a 708 bp fragment. The fragment was isolated by agarose gel electrophoresis, then purified. The replicative form (RF) DNA of phage M13mp19 was first digested with XbaI restriction endonuclease, then blunt-ended by Klenow fragment of DNA polymerase. Afterwards, this DNA was further digested with HindIII restriction endonuclease, and the large DNA fragment was isolated. The 708 bp fragment was then inserted into the XbaI blunt-ended and HindIII site of the M13mp19 DNA to yield phage M13-W23. Then site-directed mutagenesis was performed as described. Briefly, pM13-W23 was introduced into the *E. coli* CJ236 strain, which is a dut, ung strain and lacks the enzyme uracil N-glycosylase which normally removes uracil from DNA. This results in incorporation of uridine in the DNA. Then single-stranded (SS)-DNA containing uridine from phage M13-W23 was used as template for site-directed mutagenesis to prepare the mutant M13-WW3. The oligodeoxynucleotide m18rev, 5'-CCTGGGGCTTCGCGAAG-GATTTCCTGCAAGG-3', (SEQUENCE ID NO. 30) was used for site-directed mutagenesis. Oligonucleotide m18rev contains a phosphokinase recognition site RRIS and also a NruI recognition site. Oligonucleotide m18rev was annealed to uridine-containing SS-DNA of M13-WW23, followed by the in vitro synthesis of the complementary strand. Afterwards, the resultant double-stranded (DS) DNA was transformed into *E. coli* DH5F' strain with a functional uracil N-glycosylase to remove the parental strand. The desired mutant was characterized by NruI restriction endonuclease digestion and DNA sequencing. Thus the construct M13-WW3 was obtained. Then RF-DNA of M13-WW3 was digested with XhoI and HindIII restriction endonucleases, and the resultant 420 bp fragment was first inserted into the intermediate vector pCC49t-BglII-BstEII that was digested with the same endonucleases to yield plasmid pCC49t-WW3. Then pCC49t-WW3 was digested with XbaI, and HindIII restriction endonucleases, and the resultant 2983 bp fragment was isolated. The vector pCC49 was digested with the same endonucleases and large fragment of 6440 bp was isolated. The 2983 bp fragment was ligated to this 6440 bp of the vector fragment to yield plasmid pWW3. The vector pWW3 expresses the MAb-WW3 with amino acid substitutions V18R and K19R in the MAb-CC49 heavy chain.

To construct plasmid pWW4, the vector pCC49 was digested with XbaI and BamHI restriction endonucleases to isolate a 415 bp fragment. The fragment was isolated by agarose gel electrophoresis, then purified. The replicative form (RF) DNA of phage M13mp18 was digested with XbaI and BamHI restriction endonucleases and the large DNA fragment isolated. The 415 bp fragment was then inserted into the XbaI and BamHI site of the M13mp18 DNA to yield phage M13-W24. Then site-directed mutagenesis was performed as described. Briefly, pM13-W24 was introduced into the E. coli CJ236 strain, which is a dut, ung strain and lacks the enzyme uracil N-glycosylase which normally removes uracil from DNA. This results in incorporation of uridine in the DNA. Then single-stranded (SS)-DNA containing uridine from phage M13-W24 was used as template for site-directed mutagenesis to prepare the mutant M13-WW4. The oligodeoxynucleotide mL 17-2, 5'-GTGTCAGT-TGGCCGGAGGGTTACTTTGAGC-3', (SEQUENCE ID NO. 31) was used for site-directed mutagenesis. Oligonucleotide mL17-2 contains a phosphokinase recognition site RRVT and also a EaeI recognition site. Oligonucleotide mL17-2 was annealed to uridine-containing SS-DNA of M13-WW24, followed by the in vitro synthesis of the complementary strand. Afterwards, the resultant double-stranded (DS) DNA was transformed into E. Coli DH5F' strain with a functional uracil N-glycosylase to remove the parental strand. The desired mutant was characterized by EaeI restriction endonuclease digestion and DNA sequencing. Thus, the construct M13-WW4 was obtained. Then RF-DNA of M13-WW4 was digested with XbaI and BamHI restriction endonucleases, and the resultant 410 bp fragment was inserted into vector pCC49 that was digested with the same endonucleases to yield plasmid pWW4. The vector pWW4 expresses the MAb-WW4 with amino acid substitutions E17R and K18R in the MAb-CC49 heavy chain.

6. Expression of Mutant MAbs

Electroporation was used to introduce the plasmid pWW1-pWW4 into mouse myeloma NSO cells. First, $2\times10^7$ cells in 450 µl of ice cold PBS was mixed with 12 µg of purified plasmid in an electroporation cuvette. The cells were incubated on ice for 10 min. The electroporator was adjusted to the following settings: 0.24 KV and 950 µF. After electroporation of cells for 30 msec (time constant), the cells were allowed to recover on ice for 10 min, then were transferred from the cuvette into 30 ml of medium containing DMEM, 10% fetal bovine serum and 1% glutamine, and then were dispensed into 96-well plates with 100 µl in each well. After 48 hours, selection medium containing DMEM, 10% fetal bovine serum, 1% glutamine, and 0.15 µM of methotrexate replaced the medium. Subsequently, selection medium was used every 3–4 days to replace the medium until stable transformants were obtained. The expression of the mutant polypeptide in the cell culture supernatants was determined by ELISA. Clones with the highest expression of mutant polypeptides were selected, grown in flasks and the supernatants were collected from these clones.

7. Purification of Mutant MAbs

The cell culture supernatant containing the mutant MAb was purified as described with some minor modifications. Briefly, a 1 ml polypeptide A column was equilibrated with three column volumes of Buffer A (3 M NaCl, 1 M glycine, pH 8.8). Solid NaCl was added to the cell culture supernatant to a concentration of 3 M. Then the pH of the cell supernatant was adjusted to pH 8.0 with 1 M glycine (pH 8.8). Supernatants (about 300 ml) were centrifuged at 7268×g for 10 min. Then after passage through 0.2 µm filter units, the supernatants were loaded onto the polypeptide A column at a flow rate of 1 ml/min. The columns were washed with Buffer A for five column volumes. Afterwards, the columns were eluted with two column volumes of Buffer B (0.2 M glycine•HCl, pH 2.5). Eluates were neutralized with 1 ml of Buffer C (0.1 M boric acid, 25 mM borax and 75 mM of NaCl). The purified MAb was dialyzed against 1000 volumes of PBS overnight at 4° C. The polypeptide concentration of IgG was determined by ELISA, and the purity of IgG was checked by SDS polyacrylamide gel electrophoresis. The purified MAb was stored in a liquid nitrogen freezer until use.

8. Phosphorylation of Mutant MAbs

The mutant MAb was labeled with [$\gamma$-$^{32}$P]ATP and the cAMP-dependent polypeptide kinase as described previously. Approximately 10 µg of MAb was incubated at 30° C. for 60 min with 0.5 mCi of [$\gamma$-$^{32}$P]ATP and 15 units of the catalytic subunit of cAMP-dependent polypeptide kinase from bovine heart muscle (6 mg/ml DTT) in 25 µl of 20 mM Tris•HCl, pH 7.4, 100 mM NaCl, and 12 mM $MgCl_2$, then cooled on ice to stop the reaction. After addition of 300 µl containing 5 mg/ml bovine serum albumin in 10 mM sodium pyrophosphate, pH 6.7, at 4° C., the 0.325 ml reaction mixture was dialyzed against 10 mM sodium pyrophosphate, pH 6.7, overnight at 4° C. Dialysis buffer was changed twice. Incorporation of radioactivity into the monoclonal antibodies was measured with a liquid scintillation spectrometer after precipitation of the polypeptide with trichloroacetic acid. To remove the labile $^{32}$P, the final product in 0.325 ml was adjusted to pH 7.4 with 1 M Tris base, then incubated at 37 C overnight.

9. Determination of Stability of Mutant [$^{32}$P]MAbs in Sera

The stability of $^{32}$P-labeled mutant MAb, was determined as described previously with minor modification. Briefly, each reaction contained 0.25 ml of a solution of bovine serum albumin (5 mg/ml in PBS), 62.5 µl of 1 M Tris•HCl, pH 7.4, and 10 µl of the [$^{32}$P]MAb ($2.4\times10^6$ cpm) for a total volume of 322.5 µl and incubated at 37° C. Portions of 20 µl were taken in duplicate over a 24-hour period to determine the stability of [$^{32}$P]phosphate attached to the MAb by TCA precipitation.

II. Results

1. Model of MAb-chCC49

The 3-D model of MAb-chCC49 was built by using the crystal structure of MAb231 as template as described under "Materials and Methods". The modeled MAb-chCC49 showed overall structural similarity to the template molecule MAb231. Again, the asymmetrical T shape and the extended hinge region were seen in the MAb-chCC49 model, which was consistent with its overall sequence similarities to MAb231. However, when either MAb-chCC49 was superimposed over MAb231, the structural differences in the overall molecules were noticeable, especially in the CDR regions of the two MAbs. This results from the sequence differences of two molecules in this region.

2. Choosing the Sites

After generating the model of MAb-chCC49, the next step was to choose the sites on MAb-chCC49 where an optimal phosphorylation site could be created. The criteria used were as follows. Since the consensus sequence for cAMP-dependent polypeptide kinase is Arg-Arg-X-Ser/Thr, the sites with maximum number of these four residues were investigated and chosen so that minimal modification of the original MAb structure would occur. Secondly, the sites in the complementarity-determining regions (CDR) were avoided. The CDR region is the portion of the MAb variable domain which binds to antigen, so any modification of these sites might change the binding affinity or specificity of the MAb. By following these criteria, twelve sites were located, nine on the heavy chain and three on the light chain. The further evaluation of these sites led to pinpointing four sites on the MAb, three on the heavy chain and one on the light chain.

The first site chosen to incorporate a phosphorylation site started at amino acid residue 120 on the heavy chain CH1 region. The mutations which needed to be introduced here were K120R and G121R. Together with P122 and S123, these four amino acid residues formed the pattern RRXS which is recognizable by cAMP-dependent polypeptide kinase. This mutant was called WW1. The second site started at amino acid residue 221 on the hinge region of the heavy chain. The mutations required were K221R and T222R. Together with H223 and T225, these four amino acid residues would be a phosphorylation site as well. This mutant was called WW2. The third site was V18R, K18R, I20, and S21, which was on the variable region of the heavy chain. The fourth site was on the variable region of the light chain. The site would have the pattern E17R, K18R, V19, and T20 after the mutation.

3. Models of Mutant MAbs

The modeled mutant MAbs all showed the asymmetrical T shape and extended hinge region as noted above for MAb231. A close look at the site where the cAMP-dependent phosphorylation site was introduced revealed that almost all the amino acid residues which are essential to the phosphorylation were exposed on the surface, suggesting that this site would be readily accessible for phosphorylation. Not surprisingly, when MAb-chCC49 and mutant MAbs were superimposed, they exhibited identical structures in most of the regions except for the area where the phosphorylation site was introduced in the mutant MAbs. No structural differences were noticeable in the CDR regions of both MAb-chCC49 and mutant MAbs, which suggested that after introduction of a phosphorylation site in the hinge region, the binding ability of the mutant MAbs would not be changed significantly.

According to the modeling data obtained so far, it is hypothesized that the low energy and hydrogen bond formation potential of the phoephorylated polypeptiodes might contribute to the defined regions of stability of the phosphate groups attached to the polypeptides. Accordingly, it is proposed that the lower the energy and the more the potential to form hydrogen bond(s) with surrounding amino acids residues, the more stable the phosphate group is attached on the poypeptides. According to this hypothesis, it is predicted that the stability of the phosphorylated mutant Mabs would be: [$^{32}$P]MAb-WW2=[$^{32}$P]MAb-WW3>[$^{32}$P]MAb-WW4>[$^{32}$P]MAb-WW1.

4. Systematic Search and Models of Mutant [$^{32}$P]MAbs

After phosphate groups were attached to Ser or Thr residues on the PKA sites of each mutant MAb, the first systematic conformational search (Table 1) was done to determine the conformation of the phosphate groups. Search results revealed that for MAb-WW1, a phosphate group attached to Ser 21 had about thirteen allowed conformations. However the energies of these conformations were above $1.1 \times 10^5$ kcal/mol, much higher than those of other mutant MAbs whose energies were around 3400 kcal/mol(Table 1). The conformation with the lowest energy was chosen, and the second systematic search for the other phosphate attached to the Mab was performed. This time, only one conformation was given, although the energy, $7.7 \times 10^4$ kcal/mol, was a bit lower than those from the first search, it was still much higher than those of other mutant MAbs. This conformation of MAb-WW1 was chosen to do further energy minimization.

For MAb-WW2, similar results were obtained after two systematic searches. Sixty one conformations were revealed, much more than the same index for other mutant MAbs in Table 1, suggesting the easy accessibility of the PKA recognition site in this MAb. The energy ranged from 3904–3906 kcal/mol. Interestingly, several conformations from both searches showed that the phosphate group had the potential to form a hydrogen bond with either the SH group of Cys 225, or the NH group of Thr 224. Therefore after first systematic search, conformations with the lowest energy were chosen, whose phosphate group can form a hydrogen bond with SH group on Cys 225, to do the second systematic search. Results were similar to those obtained on the first search. The conformation with the lowest energy from the second systematic search was chosen to do further energy minimization.

For MAb-WW3, after the first systematic search, nine conformations were obtained, the energy ranged from 4127–4129 kcal/mol. Again, the hydrogen bond formation potential was observed (Table 1). Among these conformations, the one with the lowest energy (4127 kcal/mol) was chosen, whose phosphate group can form a hydrogen bond with hydroxyl group on the side chain of Tyr 80, to do the second conformational search. Results were similar to those obtained on the first search. The conformation with the lowest energy from the second systematic search was chosen to do further energy minimization.

For MAb-WW4, the results got from two systematic searches were very similar. Only two conformations were obtained from each search. However, different from MAb-WW1, which after phosphates were attached had few allowed conformations with high energy, the energy for phosphorylated MAb-WW4, 3778 kcal/mol, was quite low. No hydrogen bond formation was observed between the phosphate on MAb-WW4 and any surrounding amino acid residues. Again, the conformation with the lowest energy from the second systematic search was chosen to do further energy minimization.

According to the modeling data we obtained so far, it is hypothesized that low energy and hydrogen bond formation potential of the phosphorylated polypeptides might contribute to the stabilities of the phosphate groups attached to the polypeptides. It is proposed that the lower the energy and the stronger the potential to form hydrogen bond(s) with surrounding amino acid residues, the more stable the phosphate group is attached on the polypeptides. According to this hypothesis, it is predicted that the stability of the phosphorylated mutant MAbs would be as such: [$^{32}$P]MAb-WW2=[$^{32}$P]MAb-WW3>[$^{32}$P]MAb-WW4>[$^{32}$P]MAb-WW1.

5. Expression and Purification of Mutant MAbs

Stable transfection of mouse myeloma NS0 cells with expression vector pMAb-WW1-pMAb-WW4 was performed as described under "Materials and Methods". The concentration of IgG produced by the clones with highest expression was about 30 µg/ml as determined by a sandwich ELISA. The mutant MAb secreted in the supernatant was purified and concentrated as described under "Materials and Methods". The final concentration of purified MAb was determined by ELISA.

6. Characterization of Mutant MAbs and Mutant [$^{32}$P]MAbs

The purified MAbs were analyzed by SDS polyacrylamide gel electrophoresis. In the presence of mercaptoethanol, two bands, one of 50 kDa and the other of 25 kDa were seen on the Coomassie brilliant-blue stained gel. These corresponded to the heavy chain and the light chain of the MAb, respectively. The mutant MAb was phosphorylated by cAMP-dependent polypeptide kinase with [γ-$^{32}$P]ATP to a specific radioactivity of 500 Ci/mmol. After reduction with 2-mercaptoethanol, the phosphorylated mutant MAb migrated as a single band at 50 kDa shown by autoradiography, corresponding to the position of the heavy chain of the MAb on a Coomassie blue stained gel. The result was consistent with the fact that the phosphorylation site was on the heavy chain of the mutant MAbs.

7. Stability Assays

Stability assays of these mutant MAbs were carried out in the buffer (5 mg/ml BSA in PBS). The percentages of $^{32}P$ radioactivity remaining on the MAb at different time points were determined by comparing it with that of the initial values of the [$^{32}P$]MAb. After 24 hr incubation in buffer, about 93%, 99%, 98%, and 97% of the phosphate remained stably attached to MAb-WW1, MAb-WW2, MAb-WW3, and MAb-WW4. This confirmed our prediction that the stabilities of the phosphates to hydrolysis was [$^{32}P$]MAb-WW2=[$^{32}P$]MAb-WW3>[$^{32}P$]MAb-WW4>[$^{32}P$]MAb-WW1. That is, the lower the energy and the more the potential to form hydrogen bonds, the more stable the attached $^{32}P$ was on the Mab due to the protective environment surrounding the phosphate.

III. Discussion

Although $^{32}P$ has been considered as an ideal radioisotope in radio-immunotherapy for many years, its utilization was limited for two reasons. Firstly, there were no easy labeling procedure applicable to all polypeptides. This problem was solved when a labeling procedure which proved to be simple, efficient and applicable to virtually any polypeptide was developed.

The second problem is that the attached $^{32}P$ was not stable when the labeled polypeptide was incubated in buffer. Several methods were suggested to improve the stabilities of the phosphorylatable MAbs. However, no satisfactory results were reported by these attempts. In this report, the problem was tackled from a different angle. First, instead of randomly choosing a site, molecular modeling was used to locate sites where PKA recognition sites could be introduced. By following the criteria described in "Results", three sites on the heavy chain and one site on the light chain were chosed. Then, a protocol was devekoped to build the models of the mutant MAbs. Since the phosphate group is a quite big group, structural distortion may result from its attachment to Ser/Thr residues of the MAb. To verify this possibility, phosphate groups were introduced to the Ser/Thr residues at the PKA recognition sites of the MAb after the models of the mutant Mabs were built. In addition, conformational searches were done to see which conformation the MAb would take after the attachment of the phosphate group. The results showed that, in this case, phosphate groups would not change the structures of the mutant MAbs significantly. There were two interesting phenomena. First, after addition of the phosphate group, the energy within the whole molecule became very high for some of the constructs (MAb-WW1), while for other constructs the energy was quite low (MAb-WW2, MAb-WW3, MAb-WW4). Second, the phosphates on some constructs had the potential to form hydrogen bonds with adjacent amino acid residues (MAb-WW2, MAb-WW3), while those on other constructs did not (MAb-WW1, MAb-WW4). Since both of these two factors (the energy and potential of hydrogen bond formation) can affect the interactions of the molecules, it is hypothesized that the energy and potential of hydrogen bond formation can reflect the stability of the [$^{32}P$]MAb. That is, the lower the energy and the stronger potential to form hydrogen bonds, the more stable the attached $^{32}P$ was on the MAb. According to this hypothesis, it is predicted the stabilities of the mutant MAbs, that is: [$^{32}P$]MAb-WW2=[$^{32}P$]MAb-WW3>[$^{32}P$]MAb-WW4>[$^{32}P$]MAb-WW1. This prediction was confirmed by stability assays of mutant [$^{32}P$]MAbs in BSA. Although the correctness of the hypothesis is still subject to additional testing, the study showed a new way to analysis the biochemical property of the polypeptides by using molecular modeling tools.

It is noteworthy that before we modeled MAb-chCC49, questions arose as to which structure could be used as template. Although the structures of intact MAbs have been a subject of great interest for many years, due to the intrinsic mobility and segmental flexibility of antibodies, it is extremely difficult to get the crystal structure of an intact antibody. So far crystal structures of only two intact MAbs have been solved. One is MAb231, a mouse IgG2a MAb against canine lymphoma cells. While the other is MAb61.1.3, a murine IgG1 MAb against phenobarbital. Since one site on which mutations were inroduced was in the hinge region of the MAb, it was decided to use the crystal structure of the intact MAb as template. Evaluation of the crystal structures of these two intact MAbs revealed the relative position of the Fab, hinge and Fc regions. In addition, both showed an overall asymmetry, which might manifest a considerable degree of intrinsic mobility and segmental flexibility of the antibodies. Other structural features of the two MAbs though, were quite different. The IgG1 has a distorted yet compact Y shape, whereas IgG2a has a more extended T shape. This difference may well reflect differences in their hinge regions. The hinge of IgG2a which has 23 amino acids is longer than that of IgG1 by six amino acids, three in the upper hinge region and three in the lower hinge region. The overall sequence comparisons performed with the Bestfit Program in the GCG package (Wisconsin Package Version 10, Genetics Computer Group (GCG), Madison, Wis.) indicated that IgG1 shares a little more sequence homology with MAb-chCC49 than does IgG2a. The results demonstrated that the light chain sequences of MAb61.1.3 (IgG1) and MAb-chCC49 share 65% identity and 72% similarity, whereas that of MAb231 (IgG2a) and MAb-chCC49 share 63% identity and 70% similarity; and that the heavy chain sequences of IgG1 and MAb-chCC49 show 64% identity and 74% similarity, whereas IgG2a and MAb-chCC49 show 60% identity and 68% similarity. However, when sequences of the hinge regions were used to do the comparison, it was found that the hinge of MAb-chCC49 resembles more that of MAb231 in terms of both length and amino acid sequence than that of MAb61.1.3. Like MAb231, MAb-chCC49 also has a long hinge, only one amino acid less than that of MAb231, suggesting that it might take on a similar extended structure as MAb231. MAb231 and MAb-chCC49 also share substantial sequence identity (about 90%), in both core and lower hinge regions. On the other hand, MAb-chCC49 and MAb61.1.3 do not resemble each other in this region. Compared to MAb-chCC49, MAb61.1.3 has a much shorter hinge. Sequence alignment also showed that they have very low homology in this region. Since our mutant MAb would have a phosphorylation site in the hinge region, it was decided to continue to use MAb231 as our template to model the whole molecule of MAb-chCC49.

This work also showed that molecular modeling can save time and also make precise predictions for the structures of the desired polypeptides. For instance, according to the two criteria we mentioned under the "Results", more than ten sites in the whole Ab of MAb-chCC49 were found. Evaluation of models of these putative mutant Abs suggested that not all these sites were good for site-directed mutagenesis. Some models of the putative mutant Abs showed that after mutation, the side chains of the mutated amino acids would severely interfere those of residues in the neighborhood, especially the residues in the CDR regions, as in the case of mutations in the variable region of MAb. Some other models showed that after mutation, the phosphorylation site would be buried deeply inside of the MAb as it could happen if the mutation was introduced in the Fc portion of the mutant Ab. This would pose a problem for phosphorylation as it was suggested that it is better to have an exposed phosphorylation site to get good phosphorylation. Those mutants, models of which did not show the problems of the above kinds, were eventually chosen for the further work.

The teachings of U.S. Pat. No. 5,986,061 are hereby incorporated by reference herein in their entirety.

The polypeptides modified in accordance with the invention by the presence of one or more phosphorylated groups—or analogs thereof, i.e. sulfur—have numerous applications and uses in the biological, medical, biomedical (including therapeutic and diagnostic), and other sciences.

It is contemplated that polypeptides modified by the methods disclosed in the instant invention can have additional specific uses. A few illustrations of such uses are described below. However, it is understood that these specific described uses are not intended to limit the scope of the invention.

Pharmacokinetics of Polypeptides

It is often useful to follow the fate of injected polypeptides in animals and patients. It is shown below that the phosphorus attached to some of these polypeptides is relatively stable in mouse serum; thus the pharmacokinetics of polypeptides can be conveniently studied. The instant invention provides a method to generate more stably attached phosphate groups using computer modeling, thus, polypeptides phosphorylated that way are especially well-suited for such applications.

For uses of the phosphorylated polypeptides or analogs of the invention where the polypeptide is expected to be in contact with human or animal serum, it is necessary that the polypeptide derivative be stable in human or animal serum. The derivative polypeptide should be stable in the serum of the species in which the pharmacokinetic studies (or application) are to be carried out, or in a serum equivalent, i.e., from the biological point of view, to the serum of the species on which the work is to be performed.

For instance, in the work described above, the phosphate linked to MAb-WW5 is much more stable than that of MAb-chCC49K1 in mouse serum at 37° C. After 24 hours at 37° C., approximately 99% and 92% of the phosphate groups were still attached to MAb-WW5 and MAb-chCC49K1, respectively. Thus, for applications where the stability of the phosphorylated derivative is critical, a serum-stable derivative generated using the instant invention will be used.

The applications described herein are not limited to polypeptides phosphorylated at the serine residue; it has been described above how kinases phosphorylate other amino acids such as threonine or tyrosine. Thus, polypeptides modified at these amino acids are within the contemplation of the invention. Because of the configuration of such derivatized labeled polypeptides, it is not to be excluded that their stability in serum may be improved if the corresponding serine-phosphorylated derivative is not adequately serum-stable.

General Diagnostic Reagents

Additional specific applications of the modified polypeptides of the invention are noteworthy. As referred to herein, virtually all polypeptides can be engineered to introduce single or multiple phosphorylation (or analog) sites. Such polypeptides can be used for a wide variety of scientific purposes: to study the fate of these polypeptides in animals or humans; to study their stabilities; or for use as any laboratory reagent where a radioactive polypeptide is useful.

For example, molecular weight standards are commonly used for polyacrylamide gel electrophoresis. Polypeptides with phosphorylation sites would make convenient autoradiographic markers such as molecular weight markers, isolectric focusing markers or other markers. For such applications the serum stability is generally not critical, nor is the retention of the biological activity of the polypeptide, e.g., Ag binding. Thus, for certain uses or applications it is not essential that a phosphorylatable polypeptide in accordance with the invention have biological activity.

Anticancer Therapeutic "Bomb"

A particularly noteworthy and interesting application made possible by the invention is what has been called here in the vernacular, a therapeutic or more specifically an antitumor "therapeutic radiation bomb". Such a biologically-active composition uses biotin coupled to a tumor-specific monoclonal antibody (MAb) (or to Fab or Fab' fragments if more appropriate), and a multiple "modified" streptavidin bound to each MAb-bound biotin, each streptavidin being modified in that it has multiple phosphorylated groups. Since streptavidin is itself a tetramer, multiple radioactive groups are thus provided. These multiple radioactive groups expose the tumor with radiation which is greatly amplified and hence more readily detectable and would produce greater tumor destruction. In the case where it is highly phosphorylatable it is much more easily detectable. Thus, each one of the biotins which is bound to each tumor-specific MAb binds tightly to the multiple streptavidin molecules which in turn contain multiple labeled phosphorus atoms, or their equivalent isotopes.

It is evident that depending on the therapeutic or diagnostic objectives, all streptavidins may be radioactive-phosphorus labeled or partially or totally radioactive-thiophosphorus labeled, or labeled with different phosphorus or sulfur isotopes, which have different decay modes or levels of radiation energy. Such isotopes are discussed below.

Because antibody molecules are themselves multichain molecules, many sites can be introduced into the antibodies or Fab fragments directly by the procedures of this invention.

Hormones, Cytokines, Lymphokines, Growth Factors

Hormones labeled with radioactive phosphorus or sulfur are another class of biological materials within the scope of this invention. For instance, phosphorylated (e.g., $^{33}P$, $^{32}P$) hormones can be bound to specific cell types differentially over other tissues. Cancerous tissues containing increased number of receptors for such hormones can be treated with appropriately phosphorylated hormones which will then specifically bind to these cells; thus therapy will be significantly improved.

Further, labeled hormones are commonly used for receptor studies to examine their binding to cell surface receptors, to soluble receptors or other reagents and materials.

Typical of the labeled hormones ($^{33}P$, $^{32}P$) contemplated by the invention are growth hormone, insulin, FSH; LH, and others. It is evident such hormones genetically constructed lend themselves to the introduction of one or more putative phosphorylatable or thiophosphorylatable groups.

As noted above for hormones, the same considerations apply to cytokines, lymphokines, growth factors (i.e., IL-1, IL-2, IL-3, TNF-alpha, TNF-beta, the various CSF molecules, erythropoietin EGF, NGF and others) and any polypeptides with cell and/or tissue specificity to one degree or another.

Antibodies

Streptavidin labeled by means of phosphorylation may be used directly to enhance immunoassays as a substitute for unlabeled streptavidin or enzyme-linked unlabeled streptavidin. The invention also contemplates introducing phosphorus or analog labels into genetically engineered antibodies, more particularly MAbs, or in the Fab or Fab' fragment. Such MAbs are useful for diagnostic and therapeutic purposes. The phosphorylated MAbs can be made to target specific tumor-associated antigens or a variety of tumors, like breast and colon cancer cells, malignant melanoma cells, ovarian carcinoma cells, and other malignant tumors.

Further Therapeutic Uses

Other uses contemplated in accordance with the invention are as follows: Monoclonal or appropriate cocktails of antibodies and/or antibody fragments (such as the Fab or Fab' fragments) are fruitful molecules in which in accordance with the invention phosphorylation or other labellable sites can be introduced. The use of $^{32}P$ in therapy has been demonstrated for polycythemia vera and other malignancies. Thus, it is clear that the high energy beta. particle is effective as an anticellular agent. The attachment of $^{32}P$ through the introduction of phosphorylation site(s) in MAbs or their appropriate fragments (Fab and Fab') would also be effective for the therapy of tumors to which these monoclonal antibodies are specific. A large number of monoclonal antibodies have been developed to tumor-associated antigens from breast, colon, ovarian, and other adenocarcinomas, malignant melanoma, and many other tumors. Thus, MAbs directed to the tumor associated antigens of these tumors are expected to be highly effective when labeled with $^{32}P$. The labelling can be increased by use of cassettes of phosphorylation sites or directly by introduction of multiple phosphorylation sites into the intact polypeptide or the appropriate fragments through genetic engineering. By "cassette" is meant a multifunctional moiety. A distinct advantage of the instant invention is that multiple labeled phosphorylation sites, when introduced in accordance with the instant invention in MAbs, will not reduce the binding specificity and/or affinity of the modified MAbs for the specific epitope targeted.

The invention also has implications for the preparation of therapeutic agents to which patients are likely to develop an adverse antigenic response. Thus, the monoclonal antibodies can be engineered successively in accordance with the invention with different phosphorylation sites. When introduced into patients who have become sensitive to or who are producing antibodies to the injected antibody because of the phosphorylation site, then by changing to a different phosphorylation site, the antigenic character of the polypeptide can be modified. Thus, it may be possible to use such antibodies in multiple successive therapeutic regimens in patients who are reacting with the antibody of the previous type. For this purpose a series of antibodies with a variety of phosphorylation sites can be developed. Each series would be designed to have a different epitopic structure and be used sequentially. Alternatively a cocktail of such different antibodies can be used initially so that any one is present at a fraction of the total. This would minimize antibody formation to any one of the new sites. Due to the relative easiness of designing potential phosphorylation sites using the instant invention, such effort can be greatly simplified within a short period of time.

Various Isotopes

In accordance with the invention, as discussed above, phosphorylated derivatives should be serum-stable for certain applications. Various isotopes can be employed that are more effective than others for a specific therapeutic purpose. For example, $^{33}P$ may be substituted for $^{32}P$ in the phosphorylation reaction. It is less likely that $^{35}S$ with a half-life of about 89 days would be normally as useful as an anticellular reagent because it is a low energy beta emitter. Nevertheless, conceivably there may be specific uses for $^{35}S$ labeled MAbs in therapy and/or diagnosis.

Table I below shows various isotopes (and other pertinent particulars) which are especially useful for introduction into polypeptides in accordance with the invention.

TABLE I

Isotopes for Labellable Groups

| Isotope | Half-Life | Type of Decay | Energy of Radiation |
|---------|-----------|---------------|---------------------|
| $^{32}P$ | 14.2 days | beta | 1.707 MeV |
| $^{32}P$ | 24.4 days | beta | 0.25 MeV |
| $^{35}S$ | 87.0 days | alpha | 0.167 MeV |
| $^{38}S$ | 2.87 hours | alpha | 1.1 MeV |

Accordingly, the invention provides tailored-designed polypeptides for specific biological purposes.

An important implication of this invention is the greater safety of the labeled MAbs due to lower energy emission levels and the nature of the radio emission. Specifically, MAbs labeled with 32P or 33P have significantly lower energy emission levels than conventional radio-labels for polypeptide such as $^{125}I$; moreover, the decay emission of the phosphorus and sulfur isotopes (32P, $^{33}P$, $^{35}S$ and $^{38}S$) is beta or alpha particles, as compared to gamma rays of $^{125}I$ as are common in existing labelling protocols.

The safety feature of the beta-labeled polypeptides, e.g., MAbs or streptavidins in accordance with the invention, is very significant for diagnostic and therapeutic uses of the invention. Beta emitters penetrate the tumor but are not emitted as readily as gamma ray emitters from the patient to surrounding medical staff and non-medical attending individuals.

By selecting $^{35}S$ (which has a half-life of 87 days) and the $^{35}S$ phosphate ATP analog to $^{32}P$ one can significantly increase the effective radioactive life of the therapeutic agent.

Thus, the polypeptides labeled in accordance with the invention have a spectrum of meaningful advantageous properties heretofore not readily available.

The invention is not limited to the use of unstable isotopes. In the future it may be advantageous to label a polypeptide with a stable isotope that would be suitable for detection by NMR, nuclear activation, or future developed procedures. Nor is it necessary that the label be a "radio" label providing it is an identifiable label.

Radioimmunoassays with Labeled Antigens

In accordance with the invention the phosphorylated polypeptides can be generally used as the radio-labeled component. These radioimmunoassays can be used with polyclonal as well as with monoclonal antibodies. If the introduction of a new phosphorylation site into a polypeptide changes the antigenic structure of the polypeptide in the area of the phosphorylation site, or even at distant linear positions of the polypeptide, and alters the antigenic behavior, the polypeptide in accordance with the invention, can be modified to introduce a phosphorylation site at a different position so that the antigenic behavior will remain stable and for the polypeptide to bind with the polyclonal or monoclonal antibody of interest. Again, the instant invention employing computer modeling will greatly speed up the whole process. Furthermore, because of its high energy, $^{32}P$ secondary Bremsstrahlung radiation can be used for imaging.

Thus, the invention provides considerable versatility regarding the position where the label can be introduced. Generally the phosphorus (or other radio-label) introduced will not disrupt the antigen-antibody binding in accordance with the instant invention.

Sandwich Radioimmunoassays

In sandwich radioimmunoassays with monoclonal antibodies, the introduction of phosphorylation sites into an antibody in accordance with the invention is a sensitive method to follow the binding of the second antibody. Thus, the sensitivity of such sandwich radioimmunoassays can be increased substantially. Particularly, when multiple phosphorylation sites are introduced in accordance with the invention into the polypeptide directly or by the addition of a fusion phosphorylation cassette, the sensitivity of such assays will be increased many-fold. Again, the instant invention has the unique advantage of simultaneously modeling several introduced phosphate groups and predict their potential effects on the overall stability and conformation of the phosphorylated polypeptide.

Another advantage of the invention is to be noted. Because the phosphorylation reaction is gentle, unlike the iodination or other chemical modifications necessary to radio-label polypeptides with iodine or other reagents, monoclonal antibodies that are inactivated by the chemical or iodination procedures are not likely to be inactivated by the phosphorylation procedure. Thus, the process of the invention allows for the phosphorylation of polypeptides normally too sensitive for labelling with iodine. The introduction of a phosphate analog with $^{35}S$ provides a radio-labeled polypeptide derivative with a long half-life (1.5 times longer than $^{125}I$ and 6 times longer than $^{32}P$). Thus, when MAbs are labeled with $^{35}S$, they will have a substantially longer shelf-life compared to the $^{32}P$ or $^{125}I$ radio-labeled derivatives.

As discussed above, the invention allows for the selection of the most appropriate labelling isotope, as compared to $^{125}I$, for instance.

Imaging

Generally for imaging of tumors or tissues in an animal or a patient, a high energy gamma emitter is generally preferable to a relatively low energy beta emitter, which by and large would be absorbed by the tissues. However, in certain imaging studies in animals or in patients, MAbs to which $^{32}P$, $^{33}P$ or $^{35}S$ are attached through introduced phosphorylation sites in accordance with the invention may be useful.

For example, it can be seen that MAbs labeled with $^{32}P$, $^{33}P$ or $^{35}S$ could be useful in in vivo studies in which biopsy specimens are to be examined. The spread of a tumor during surgery could be followed by utilizing a radioisotope detector probe to follow the local spread of the tumor and guide the extent of the surgery. In addition, tissue specimens which are fixed or frozen can be taken to which these polypeptides will remain bound (that is, antibodies to the tumor-associated antigens or other ligands). Thus, autoradiographs of tissue sections can provide information about the extent of tumor spread and the extent of binding of specific monoclonal antibodies to tumor-associated antigens can be thoroughly evaluated. Furthermore, as an in vitro reagent with cells or tissue slices, such labeled antibodies would be highly sensitive reagents to detect tumor-associated antigens or other antigens by the usual types of assays employed.

Anti-antibodies

There are many known uses for anti-antibodies such as anti-mouse, anti-human, anti-sheep, and anti-goat antibodies, etc. or monoclonal antibodies as single entities or as a cocktail. Such antibodies can be engineered in accordance with the invention to introduce single or multiple phosphorylation sites and, accordingly labeled with a variety of isotopes as described above. These provide general reagents where anti-antibodies are necessary, particularly in radioimmunoassays, autoradiography, or any other reactions in which anti-antibodies are useful.

Rapid Purification of Phosphorylated Polypeptides

The invention has also applications in separating and purifying polypeptides. Polypeptides which are phosphorylated can be separated from those which are not; polypeptides which are more phosphorylated than others can be separated.

For instance, where polypeptides can be phosphorylated, it is common for only a percentage of the molecules to be phosphorylated. The total phosphorylation, of course, can be enhanced by the introduction of multiple phosphorylation sites in the polypeptide in accordance with the invention so that few molecules escape phosphorylation. To be able to separate the phosphorylated from the non-phosphorylated polypeptides is especially useful for molecules with a single phosphorylation site where there may be phosphorylated and non-phosphorylated molecules in the population. In this manner, the effectiveness of any phosphorylated derivatives is increased. Separation of phosphorylated from non-phosphorylated molecules can be accomplished by developing polyclonal or monoclonal antibodies to the phosphorylation sites with and/or without derivatized phosphate groups. Such polyclonal and monoclonal antibodies are expected to have considerable value in purifying the polypeptides and have been described.

Dephosphorylation of Polypeptides

Considerable emphasis has been placed herein on aspects of phosphorylation. It is a consequence of the phosphorylation (with phosphate or thiophosphate groups) that the removal of the label is also facilitated in that dephosphorylation is a milder procedure which tends to be less disruptive of the polypeptide molecule than procedures in the prior art for removal of $^{125}I$ from polypeptides. Thus, in cases where it is useful to remove the radioisotope, this can be achieved relatively easily and gently by an enzyme reaction. A variety of phosphatases can be used for this purpose. Most phosphatases have comparatively low specificity although a few have very high specificity such as those acting on sugar phosphates and the enzyme that dephosphorylates glycogen synthetase b and phosphorylase b. Furthermore, specific dephosphorylation of phosphorylated polypeptides can be achieved by reversal of the reaction of polypeptide-serine and -tyrosine kinases. If it is necessary to determine whether in fact the phosphate addition causes a change in the activity of the polypeptide, rather than aging, denaturation, or other manipulations, the phosphate can be removed and the activity of the polypeptide again determined. In such a manner, a definitive understanding of the effect of phosphorylation on the activity of the polypeptide can be assessed. This may be useful in determining the activities of various phosphorylated interferons.

The concept of "dephosphorylation" has an interesting application which is essentially the "converse" of that taught herein. Wherever a site in a polypeptide in the native state is naturally phosphorylatable the removal of that site would be particularly desirable when it is known that the naturally phosphorylatable polypeptide causes some undesired results. An illustration would be polypeptides associated with oncogenic viruses such as Rous sarcoma virus (RSV) and cellular oncogenes.

Phosphorylation Cassettes

The invention also contemplates an alternative method for labelling polypeptides without inserting the coding sequence for the phosphorylation site (or cassette) into the nucleotide coding sequence of the polypeptide, and yet still use the invention. This procedure would be particularly useful for large polypeptides like immunoglobulins for use in various assays. Such alternative method calls for a polypeptide which is phosphorylated to be chemically linked to the large polypeptide. The linking would be by any bifunctional reagent or an activated derivative (like N-hydroxy-succinimide), as is known in the art.

This technique could use a polypeptide with multiple phosphorylation sites in tandem or "cassette" that can be introduced within or at either end of a polypeptide. The DNA coding for the tandem phosphorylation sites would be flanked by restriction sites for easy cleaving and insertion into the DNA containing the coding sequence for the polypeptide to be linked to the larger polypeptide. Such a phosphorylation cassette could be expressed as a small polypeptide then phosphorylated and then chemically linked to the larger polypeptide.

Phosphorylatable Human or Animal Donor Genes

Further, it is within the contemplation of the invention to provide DNA sequences engineered into appropriate vectors or cell lines or even into animals by transgenic techniques. Thus cells or animals could produce phosphory-latable (and/or phosphorylated) polypeptides such as immunoglobulins after phsphorylation sites are introduced into the polypeptides by the methods of this invention. Phosphorylatable chimeric antibodies with a mouse variable region and human constant region could be developed. The human antibodies used as the donor molecule would be engineered to contain single or multiple phosphorylation sites. By analogy, this could be applied to polypeptides other than immunoglobulins.

Other Applications

There are other applications for the labeled polypeptides of the invention. In general virtually any polypeptide that contains a label (radio-label, fluorescent-label, chemical-label, enzyme-label, etc.) can alternatively be labeled with phosphate by the introduction of phosphorylation site(s) in accordance with the invention. The purification of such polypeptides can be followed in a sensitive assay by simply measuring the ability to accept a phosphate group rather than to follow enzyme activity. Such polypeptides engineered in accordance with the invention, therefore, can be purified easily and themselves be used as a tracer to follow the purification of other polypeptides to which they are similar. For example, it is likely that a polypeptide with a single phosphorylation site engineered with very little modification of the polypeptide structure itself would be purified similarly to the unmodified polypeptide.

In practice, by having a stock of phosphorylatable polypeptides or series of markers, the labeled derivatives can be prepared conveniently by the simple phosphorylation reaction when desired. Thus, the polypeptides of the invention which are phosphorylatable provide a useful inventory of the corresponding labeled polypeptides.

Pharmaceutical and Biologically Active Compositions

The modified polypeptides of the invention can be formulated according to known methods to prepare pharmaceutically useful compositions. For instance, the MAb hereof is combined in a mixture with a pharmaceutically acceptable carrier vehicle. Suitable vehicles and their formulation are described in Remington's Pharmaceutical Sciences by E. W. Martin, which is hereby incorporated herein by reference in its entirety. Such compositions will contain an effective amount of the MAb or other polypeptides hereof together with a suitable amount of vehicle in order to prepare pharmaceutically acceptable compositions suitable for effective administration to the host. The host may or may not be a mammal. The carrier may be liquid, solid, or gaseous. Of course, therapeutic applications for humans and veterinary applications are intended for the biologically active compositions of the invention. The biologically active composition of the invention is to be administered in a biologically or therapeutically effective amount which can be readily determined by one skilled in the art. Generally it is the smallest amount for which a desired response will be obtained to an amount which is excessive for practical or other purposes.

The biologically active compositions of the invention can also include any other biologically active substance which does not adversely affect the desired activity, particularly the activity or use of the modified polypeptide of the invention.

It is understood that the modified polypeptides of the invention can be obtained by chemical and/or enzymatic synthesis rather than by recombinant DNA technology.

While reference has been made to particular preferred embodiments and to several uses and applications made possible by the invention, it will be understood that the present invention is not to be construed as limited to such, but rather to the lawful scope of the appended claims and subject matter covered by the doctrine of equivalents.

TABLE 1

Systematic search result of mutant MAbs

| | | | First round systematic search | | | Second round systematic search | |
|---|---|---|---|---|---|---|---|
| | | Bonds searched (Cα-Cβ, Cβ-Oγ) | Chain no. | No. of allowed conformations | H-bonding with surrounding amino acids | Energy (kcal/mol) | Bonds searched in addition to Cα-Cβ, Cβ-Oγ | No. of allowed conformations |
| CC49K1 | S449 | 1 | 18 | no | 6574–6576 | S449 (Cϕ, Cψ) | 655 |
| | S455 | 1 | 43 | no | 6574–6577 | S455 (Cϕ, Cψ) | 186 |
| | S449 | 2 | 54 | yes | 3951–3953 | S449 (Cϕ, Cψ) | 496 |
| | S455 | 2 | 15 | no | 3952–3954 | A454, S455, M456 (Cϕ, Cψ) | 2298 |
| CC49CKI | S450 | 1 | 40 | yes | 3841–3843 | S450 (Cϕ, Cψ) | 47 |
| | S457 | 1 | 28 | no | 3841–3844 | S457 (Cϕ, Cψ) | 618 |
| | S450 | 2 | 6 | yes | 3841–3842 | D449, S450 (Cϕ, Cψ) | 312 |

TABLE 1-continued

Systematic search result of mutant MAbs

| | | First round systematic search | | | | Second round systematic search | |
|---|---|---|---|---|---|---|---|
| | Bonds searched (Cα-Cβ, Cβ-Oγ) | Chain no. | No. of allowed conformations | H-bonding with surrounding amino acids | Energy (kcal/mol) | Bonds searched in addition to Cα-Cβ, Cβ-Oγ | No. of allowed conformations |
| | S457 | 2 | 30 | yes | 3847–3849 | S457 (Cφ, Cψ) | 1189 |
| CC49CK II | S436 | 1 | 56 | yes | 3811–3813 | — | — |
| | S436 | 2 | 48 | no | 3816–3817 | — | — |
| CC49Tyr | Y455 | 1 | 60 | no | 3900–3902 | — | — |
| | Y455 | 2 | 213 | yes | 3899–3904 | — | — |
| CC49-6P | S449 | 1 | 11 | yes | 4366–4368 | S449 (Cφ, Cψ) | 125 |
| | S455 | 1 | 13 | yes | 4375–4377 | S455 (Cφ, Cψ) | 85 |
| | S464 | 1 | 15 | yes | 4382–4385 | A463, S464, L465 (Cφ, Cψ) | 679 |
| | S470 | 1 | 50 | no | 4392–4396 | — | — |
| | S479 | 1 | 20 | yes | 4395–4398 | — | — |
| | S485 | 1 | 49 | no | 4400–4404 | — | — |
| | S449 | 2 | 58 | yes | 4406–4408 | — | — |
| | S455 | 2 | 15 | yes | 4411–4413 | A454, S455, M456 (Cφ, Cψ) | 8389 |
| | S464 | 2 | 0 | — | — | A463, S464, L465 (Cφ, Cψ) | 325606 |
| | S470 | 2 | 0 | — | — | R468, A469, S470, M471, K472 (Cφ, Cψ) | $5 \times 10^5$ |
| | S479 | 2 | 0 | — | — | A478, S479, L480 (Cφ, Cψ) | 263 |
| | S485 | 2 | 23 | yes | 4420–4423 | A484, S485, M486 (Cφ, Cψ) | 21508 |
| MAb-WW 1 | S123 | 1 | 13 | no | $1.1 \times 10^5$ | — | — |
| | S123 | 2 | 1 | no | 77055 | — | — |
| MAb-WW 2 | T224 | 1 | 21 | yes | 3939–3942 | — | — |
| | T224 | 2 | 13 | yes | 3908–3940 | — | — |
| MAb-WW 3 | S21 | 1 | 9 | yes | 4127–4130 | — | — |
| | S21 | 2 | 22 | yes | 3840–3842 | — | — |
| MAb-WW 4 | T20 | 1 | 2 | no | 3778–3779 | — | — |
| | T20 | 2 | 2 | no | 3776–3777 | — | — |
| MAb-WW 5 | S224 | 1 | 61 | yes | 3905–3907 | — | — |
| | S224 | 2 | 57 | yes | 3905–3907 | — | — |

TABLE 1-continued

Systematic search result of mutant MAbs

| | | | First round systematic search | | | Second round systematic search | |
|---|---|---|---|---|---|---|---|
| | Bonds searched (Cα-Cβ, Cβ-Oγ) | Chain no. | No. of allowed conformations | H-bonding with surrounding amino acids | Energy (kcal/mol) | Bonds searched in addition to Cα-Cβ, Cβ-Oγ | No. of allowed conformations |
| MAb-WW 6 | S224 | 1 | 65 | yes | 3215–3217 | — | — |
| | S224 | 2 | 54 | yes | 3224–3226 | — | — |
| MAb-WW 7 | S224 | 1 | 64 | yes | 4518–4520 | — | — |
| | S224 | 2 | 56 | yes | 9805–9808 | — | — |
| MAb-WW 8 | S224 | 1 | 62 | yes | 3820–3823 | — | — |
| | S224 | 2 | 39 | yes | 3824–3827 | — | — |

Systematic conformational searches along Cα-Cβ and Cβ-Cγ of the Ser/Thr of the PKA recognition site were performed so that allowed conformations could be obtained for each phosphorylated mutant MAb. In the column "bonds searched," the amino acid residues on which the systematic search was performed are shown. Corresponding to the figures, the column designated "chain number" refers to the left model as chain 1 and the model on the right of each figure as chain 2. The column "H-bonding with surrounding amino acids" shows whether the attached phosphate to each mutant MAb has potential to form one or more hydrogen bonds with the surrounding amino acids. In the energy column, the first number represents the conformation with the lowest energy and the second number represents the conformation with the highest energy, all calculated without energy minimization. Additional details are given under "Materials and Methods."

TABLE 2

Determination of immunoreactivities of [$^{32}$P]MAbs

| | Plate Assay | | Bead Assay | |
|---|---|---|---|---|
| | BSM | PSM | BSM | PSM |
| Bound [$^{32}$P]MAb-chCC49-6P | 66% | <1% | 95% | 4% |
| Bound [$^{32}$P]MAb-WW5 | 68% | <1% | 94% | 4% |
| Bound [$^{32}$P]MAb-WW6 | 68% | <1% | 95% | 3% |
| Bound [$^{32}$P]MAb-WW7 | 68% | <1% | 95% | 2% |

Immunoreactivities of [$^{32}$P]MAbs were measured by direct binding assays. The assays were carried out either by plate assay with BSM or PSM coated on the plates, or by bead assays with BSM or PSM bound to the beads. The percentages of [$^{32}$P]MAbs bound to the plates or beads were determined as described in details in "Materials and Methods." The assay carried out with excess antigen BSM bound to the beads is more reliable than the plate assay where BSM was not in sufficient excess.

TABLE 3

Stability of [$^{32}$P]MAb-chCC49-6P in serum

| Serum or Buffer | 1 Hour | 4 Hours | 8 Hours | 12 Hours | 24 Hours | 36 Hours |
|---|---|---|---|---|---|---|
| Human | 100 | 100 | 99 | 96 | 95 | 93 |
| Mouse | 97 | 96 | 96 | 95 | 93 | 91 |
| Fetal Bovine | 99 | 97 | 97 | 96 | 95 | 92 |
| Buffer | 98 | 97 | 96 | 96 | 96 | 93 |

The percentage of $^{32}$P retained on the [$^{32}$P]MAb-chCC49K1 in sera or buffer at various times at 37° C. was determined by TCA precipitation (Pestka, 1972). For determination of stability, $1.3 \times 10^6$ cpm was added to each reaction mixture as described under "Materials and Methods." Portions of 20 μl were taken in duplicate at the times shown for TCA precipitation. The values in the table are the average of duplicate determinations. Additional details are given under "Materials and Methods."

TABLE 4

Stability of [$^{32}$P]MAb-WW5 in serum over 5 days

| Serum or Buffer | Human | Mouse | Fetal Bovine | Buffer |
|---|---|---|---|---|
| 1 Hour | 100 | 100 | 100 | 100 |
| 4 Hours | 99.9 | 100 | 99.9 | 99.4 |
| 8 Hours | 99.7 | 99.6 | 99.8 | 100 |
| 12 Hours | 99.7 | 99.5 | 99.7 | 99.5 |
| 24 Hours (1 Day) | 99.0 | 99.6 | 99.5 | 99.2 |
| 2 Days | 98.3 | 100 | 98.3 | 99.4 |
| 3 Days | 97.4 | 100 | 97.6 | 99.4 |
| 4 Days | 96.7 | 100 | 96.8 | 99.1 |
| 5 Days | 96.1 | 98.4 | 95.5 | 99.3 |

The percentage of $^{32}$P retained on the [$^{32}$P]MAb-WW5 was determined as described in the legend to Table 3.

TABLE 5

Stability of [$^{32}$P]MAb-WW5, -WW6 and -WW7 in buffer over 21 days

| MAbs Days | [$^{32}$P]MAb-WW5 | [$^{32}$P]MAb-WW6 | [$^{32}$P]MAb-WW7 |
|---|---|---|---|
| 1 Day | 99 | 100 | 100 |
| 2 Days | 98 | 100 | 99 |
| 3 Days | 98 | 99 | 99 |
| 4 Days | 97 | 99 | 99 |
| 5 Days | 97 | 99 | 99 |
| 6 Days | 97 | 98 | 98 |
| 9 Days | 96 | 97 | 98 |
| 12 Days | 96 | 96 | 97 |
| 14 Days | 95 | 96 | 96 |
| 16 Days | 94 | 95 | 96 |
| 18 Days | 94 | 95 | 95 |
| 21 Days | 93 | 94 | 94 |

The percentage of $^{32}$P retained on the [$^{32}$P]MAbs was determined as described in the legend to Table 3.

TABLE 6

Stability of [$^{32}$P]MAb-WW6 in serum over 5 days

| Serum or Buffer | Human | Mouse | Fetal Bovine | Buffer |
|---|---|---|---|---|
| 1 Hour | 99.7 | 99.9 | 99.9 | 100 |
| 4 Hours | 99.5 | 99.9 | 99.7 | 100 |
| 8 Hours | 99.7 | 99.6 | 99.4 | 100 |
| 12 Hours | 99.7 | 99.5 | 99.2 | 99.9 |
| 24 Hours (1 Day) | 99.5 | 99.6 | 99.2 | 99.5 |
| 2 Days | 98.2 | 99.2 | 98.4 | 99.4 |
| 3 Days | 98.0 | 98.9 | 96.6 | 99.4 |
| 4 Days | 96.6 | 98.3 | 96.0 | 99.1 |
| 5 Days | 96.0 | 97.6 | 96.0 | 99.0 |

The percentage of $^{32}$P retained on the [$^{32}$P]MAb-WW6 was determined as described in the legend to Table 3.

TABLE 7

Stability of [$^{32}$P]MAb-WW7 in serum over 5 days

| Serum or Buffer | Human | Mouse | Fetal Bovine | Buffer |
|---|---|---|---|---|
| 1 Hour | 100 | 100.0 | 100 | 100 |
| 4 Hours | 99.8 | 99.7 | 99.8 | 100 |
| 8 Hours | 99.8 | 99.5 | 99.5 | 100 |
| 12 Hours | 99.7 | 99.5 | 99.3 | 100 |
| 24 Hours (1 Day) | 99.5 | 99.4 | 99.3 | 99.6 |
| 2 Days | 97.9 | 99.2 | 98.7 | 99.4 |
| 3 Days | 97.1 | 97.7 | 97.9 | 99.2 |
| 4 Days | 96.4 | 96.3 | 97.4 | 98.9 |
| 5 Days | 95.9 | 96.1 | 96.1 | 98.8 |

The percentage of $^{32}$P retained on the [$^{32}$P]MAb-WW7 was determined as described in the legend to Table 3.

TABLE 8

Summary of potential cAMP-dependent protein kinase recognition sites on MAb-chCC49

| Potential sites | Starting amino acid | Site | Characteristics | Buried or exposed | Mutant to be made | Change in CDR | Interference with other region |
|---|---|---|---|---|---|---|---|
| 1 | 18 | VKIS | $V_H$ region | exposed | R*R*IS | not significantly | |
| 2 | 74 | KSSS | $V_H$ region | exposed | R*R*SS | | |
| 3 | 120 | KGPS | $C_{H1}$ region | exposed | R*R*PS | no | |
| 4 | 221 | KTHT | heavy chain, hinge region | exposed | R*R*HT | no | |
| 5 | 300 | RVVS | $C_{H2}$ region | buried | RR*VS | no | |
| 6 | 320 | CKVS | $C_{H2}$ region | buried | R*R*VS | no | severe sterical forbidden is reported for R320 |
| 7 | 333 | KTIS | $C_{H2}$ region | exposed | R*R*IS | no | |
| 8 | 390 | YKTT | $C_{H3}$ region | buried | R*R*TT | no | |
| 9 | 407 | SKLT | $C_{H3}$ region | buried | R*R*LT | no | severe sterical forbidden is reported for R407 |
| 10 | 17 | EKVT | $V_L$ region | exposed | R*R*VT | no | |
| 11 | 59 | ARES | $V_L$ region | exposed | R*RES | yes | |
| 12 | 114 | RKDP | $C_{L1}$ region | exposed | RR*DS* | no | |

TABLE 9

Biodistribution of [$^{32}$P]MAb-WW5, [$^{32}$P]MAb-CC49K1, [$^{131}$I]MAb-CC49 and [$^{125}$I]MAb-CC49. [$^{32}$P]MAb-WW5, [$^{32}$P]MAb-CC49K1, [$^{131}$I] MAb-CC49 and [$^{125}$I]MAb-CC49 were injected into athymic mice bearing human colon carcinoma xenografts (LS-174T). The mice were sacrificed at the indicated times (5/group) and the percentage of injected dose per gram (% ID/g) of the tumor and various normal tissues were determined.

| MAb | Tissue | Time post-i.v. injection (h) | | | |
|---|---|---|---|---|---|
| | | 24 | 48 | 72 | 168 |
| [$^{32}$P]MAb-WW5 | Blood | 7.50 | 2.54 | 2.70 | 2.52 |
| | Tumor | 22.26 | 13.90 | 18.20 | 17.83 |
| | Liver | 11.27 | 5.04 | 4.59 | 2.94 |
| | Spleen | 11.10 | 5.92 | 5.49 | 3.42 |
| | Kidney | 3.77 | 3.09 | 3.14 | 2.31 |
| | Lung | 4.17 | 2.68 | 2.86 | 1.91 |
| | Tail | 3.37 | 2.08 | 1.94 | 1.96 |
| | Carcass | 3.03 | 2.19 | 2.13 | 1.76 |
| [$^{32}$P]MAb-CC49K1 | Blood | 1.08 | 0.62 | 0.4 | 0.19 |
| | Tumor | 5.31 | 4.16 | 2.71 | 1.58 |
| | Liver | 5.35 | 3.66 | 2.79 | 1.27 |
| | Spleen | 6.53 | 4.75 | 3.66 | 1.63 |
| | Kidney | 3.50 | 2.78 | 2.29 | 1.35 |
| | Lung | 2.85 | 2.42 | 1.54 | 1.03 |
| | Tail | 2.01 | 1.94 | 1.88 | 1.82 |
| | Carcass | 2.18 | 1.91 | 1.65 | 1.28 |
| [$^{131}$I]MAb-CC49 | Blood | 2.63 | 2.19 | 1.5 | 0.22 |
| | Tumor | 7.73 | 9.14 | 12.40 | 7.98 |
| | Liver | 5.97 | 2.69 | 1.56 | 0.21 |
| | Spleen | 13.53 | 3.81 | 2.99 | 2.15 |
| | Kidney | 1.26 | 0.89 | 0.60 | 0.60 |
| | Lung | 1.65 | 1.14 | 0.76 | 0.14 |
| | Tail | 2.85 | 1.62 | 0.64 | 0.29 |
| | Carcass | 0.82 | 0.56 | 0.39 | 0.07 |
| [$^{125}$I]MAb-CC49 | Blood | 3.80 | 3.37 | 2.78 | 0.96 |
| | Tumor | 8.15 | 9.62 | 12.44 | 9.29 |
| | Liver | 7.31 | 3.56 | 2.10 | 0.39 |
| | Spleen | 16.87 | 4.59 | 3.61 | 2.67 |
| | Kidney | 1.81 | 1.36 | 0.95 | 1.00 |
| | Lung | 2.48 | 1.84 | 1.36 | 0.49 |
| | Tail | 4.34 | 2.29 | 0.96 | 0.55 |
| | Carcass | 0.91 | 0.69 | 0.55 | 0.19 |

What is claimed is:

1. A phosphorylatable antibody or antigen binding fragment thereof, engineered to include at least one heterologous kinase recognition site located in the hinge region and which does not reduce the ability of the antibody or antigen binding fragment to bind antigen, such that an added phosphate group of a phosphorylated form of the antibody or antigen binding fragment is protected from hydrolysis by intramolecular interactions with other amino acid residues so that at least 80% of all the phosphate groups of the phosphorylated form remain attached in vitro after incubation for 5 days at 37° C. in either (i) human, mouse or fetal serum, or (ii) phosphate buffered saline with 5 mg/ml bovine serum albumin.

2. The phosphorylatable antibody of claim 1, wherein at least 95% of all the phosphate groups remain attached in vitro after incubation for 5 days at 37° C. in either (i) human, mouse or fetal serum, or (ii) phosphate buffered saline with 5 mg/ml bovine serum albumin.

3. The phosphorylatable antibody of claim 2, wherein at least 99% of all the phosphate groups remain attached in vitro after incubation for 5 days at 37° C. in either (i) human, mouse or fetal serum, or (ii) phosphate buffered saline with 5 mg/ml bovine serum albumin.

4. The phosphorylatable antibody of claim 1, wherein the kinase recognition site is a recognition site for kinase which phosphorylates a serine, threonine or tyrosine residue.

5. The phosphorylatable antibody of claim 1, wherein the kinase recognition site is a recognition site for a cyclic AMP dependent kinase, a cyclic GMP dependent kinase, or a cyclic nucleotide independent kinase.

6. The phosphorylatable antibody of claim 1, wherein the kinase recognition site is a recognition site for casein kinase I, casein kinase II, Src tyrosine kinase, mitogen-activated S6 kinase or rhodopsin kinase.

7. The phosphorylatable antibody of claim 1, wherein the antibody is a monoclonal antibody.

8. The phosphorylatable antibody of claim 1, wherein the antibody is a humanized antibody, or chimeric antibody.

* * * * *